(12) United States Patent
Gzara et al.

(10) Patent No.: US 10,209,389 B2
(45) Date of Patent: Feb. 19, 2019

(54) IN-SITU CHARACTERIZATION OF FORMATION CONSTITUENTS

(71) Applicant: Schlumberger Technology Corporation, Sugar Land, TX (US)

(72) Inventors: Kais B. M. Gzara, Tunis, TN (US); Vikas Jain, Sugar Land, TX (US)

(73) Assignee: SCHLUMBERGER TECHNOLOGY CORPORATION, Sugar Land, TX (US)

(*) Notice: Subject to any disclaimer, the term of this patent is extended or adjusted under 35 U.S.C. 154(b) by 1155 days.

(21) Appl. No.: 14/369,634

(22) PCT Filed: Dec. 21, 2012

(86) PCT No.: PCT/US2012/071336
§ 371 (c)(1),
(2) Date: Jun. 27, 2014

(87) PCT Pub. No.: WO2013/101752
PCT Pub. Date: Jul. 4, 2013

(65) Prior Publication Data
US 2015/0015250 A1    Jan. 15, 2015

Related U.S. Application Data

(60) Provisional application No. 61/581,224, filed on Dec. 29, 2011.

(51) Int. Cl.
*G01V 3/00* (2006.01)
*G01V 3/32* (2006.01)
(Continued)

(52) U.S. Cl.
CPC .............. *G01V 3/32* (2013.01); *G01N 24/08* (2013.01); *G01V 3/34* (2013.01)

(58) Field of Classification Search
CPC ........................................................ G01V 3/32
(Continued)

(56) References Cited

U.S. PATENT DOCUMENTS 4,899,112 A   2/1990  Clark et al.
6,661,226 B1  12/2003 Hou et al.
(Continued)

FOREIGN PATENT DOCUMENTS

CA   2397385 A1   2/2001
EP   0544585 B1   3/1996
(Continued)

OTHER PUBLICATIONS

Decision to Grant issued in related RU application 2014131266 dated Sep. 11, 2015, 10 pages.
(Continued)

*Primary Examiner* — Louis Arana

(57) ABSTRACT

A well-logging method for a geological formation having a borehole therein may include collecting a plurality of nuclear magnetic resonance (NMR) snapshots from the borehole indicative of changes in the geological formation and defining NMR data. The method may further include identifying a plurality of fluids within the geological formation based upon the NMR data, determining respective NMR signatures for the identified fluids based upon the NMR data, determining apparent volumes for the identified fluids based upon the NMR signatures, and determining adjusted volumes for the identified fluids based upon the apparent volumes.

23 Claims, 40 Drawing Sheets

(51) Int. Cl.
*G01V 3/34* (2006.01)
*G01N 24/08* (2006.01)

(58) Field of Classification Search
USPC .................................................. 324/303, 306
See application file for complete search history.

(56) References Cited

U.S. PATENT DOCUMENTS

| | | | |
|---|---|---|---|
| 6,859,033 | B2 | 2/2005 | Speier |
| 6,866,306 | B2 | 3/2005 | Boyle et al. |
| 7,075,297 | B2 | 7/2006 | Freedman |
| 8,005,618 | B2 | 8/2011 | Gzara |
| 9,581,723 | B2 * | 2/2017 | Hurley .................... G01V 11/00 |
| 9,759,832 | B1 * | 9/2017 | Freedman ................ G01V 3/32 |
| 2004/0169511 | A1 | 9/2004 | Minh et al. |
| 2009/0167302 | A1 | 7/2009 | Edwards et al. |
| 2009/0177403 | A1 | 7/2009 | Gzara |
| 2010/0264914 | A1 | 10/2010 | Minh |
| 2010/0283459 | A1 | 11/2010 | Kruspe et al. |
| 2011/0068788 | A1 | 3/2011 | Minh |
| 2014/0114576 | A1 | 4/2014 | Jain et al. |

FOREIGN PATENT DOCUMENTS

| | | |
|---|---|---|
| GB | 2409726 A | 7/2005 |
| RU | 2367981 C2 | 11/2006 |
| RU | 2318224 C2 | 2/2008 |
| RU | 2361247 C1 | 7/2009 |
| RU | 2393509 C2 | 6/2010 |
| WO | 0026696 A1 | 5/2000 |
| WO | 2005036208 A2 | 4/2005 |
| WO | 2009143424 A2 | 11/2009 |

OTHER PUBLICATIONS

European Search Report issued in related EP application 12862152.1 dated Nov. 19, 2015, 4 pages.
Office Action issued in related EP application 12862152.1 dated Dec. 2, 2015, 5 pages.
International Search Report for International Application No. PCT/US2012/071336 dated Apr. 16, 2013.
Written Opinion issued in International Patent application PCT/US2012/071336 dated Apr. 16, 2013, 4 pages.
International Preliminary Report on Patentability issued in International Patent application PCT/US2012/071336 dated Jul. 1, 2014, 5 pages.
Examination Report issued in related EP application 12862152.1 dated Jun. 7, 2017, 4 pages.
Examination Report issued in related EP application 12862152.1 dated Dec. 20, 2017, 4 pages.
Office Action 98751 issued in Mexican Patent Application MX/a/2014/008056 dated Dec. 13, 2016, 4 pages.
Office Action 61282 issued in Mexican Patent Application MX/a/2014/008056 dated Aug. 30, 2017, 5 pages.
Examination Report issued in related EP application 12862152.1 dated Aug. 3, 2018, 4 pages.

* cited by examiner (Ana) 6.75in ADN Neutron Density Overlay
Rhofluid = 1.0 (CP-24-1998)

(Ana) 6.75in ADN Neutron Density Overlay
Rhofluid = 1.0 (CP-24-1998)

(Ana) 6.75in ADN Neutron Density Overlay
Rhofluid = 1.0 (CP-24-1998)

(Ana) 6.75in ADN Neutron Density Overlay
Rhofluid = 1.0 (CP-24-1998)

IN-SITU CHARACTERIZATION OF FORMATION CONSTITUENTS

BACKGROUND

Well logging instruments (or "tools") are used in wellbores (boreholes) to make, for example, formation evaluation measurements to infer petrophysical properties of the formations surrounding the borehole and the fluids and minerals contained therein. Such well logging instruments may include electromagnetic instruments, nuclear instruments, acoustic instruments, and nuclear magnetic resonance (NMR) instruments, for example.

Well logging instruments may be moved through a wellbore on an armored electrical cable ("wireline") after the wellbore had been drilled. Such wireline tools are still used extensively. However, the desire for information while drilling the wellbore gave rise to measurement-while-drilling ("MWD") and logging-while-drilling ("LWD") instruments, which are generally housed in special customized drill collars forming part of a string of tools called the bottom hole assembly (BHA), used to drill, steer, and log the wellbore. By collecting and processing such information during the drilling process, the wellbore operator can make informed real-time decisions pertaining to the drilling operation, to optimize wellbore trajectory or placement and drilling performance, and/or to acquire log measurements right "behind" the drillbit, in freshly drilled formations prior to borehole and/or formation alteration as a result of the drilling process, and/or for logging "insurance" or "assurance" purposes in boreholes difficult to log using wireline techniques, as the case may be.

MWD instruments may provide drilling parameter information such as drilling mechanics (e.g. axial force applied to a drillbit attached at the bottom of the drill string, also called "weight-on-bit", torque applied to the drill string, also called "downhole torque", and downhole fluid pressures either inside or outside the drillstring, sometimes converted into "equivalent fluid density" such as "ECD" and "ESD"), drilling mechanics (e.g. downhole BHA rotations per minute, also called "collar rpm", drill string shock & vibration, and downhole flowrates, using so called "turbine rpm"), wellbore directional surveys (e.g. wellbore geodetic or geomagnetic direction, and wellbore inclination from vertical), and other information like wellbore temperature. LWD instruments may provide formation evaluation measurements such as formation electrical resistivity or conductivity, complex dielectric permittivity, natural gamma-ray, bulk density and photoelectric factor, thermal or epithermal neutron porosity, thermal neutron capture cross-section (called "SIGMA"), a variety of neutron induced gamma-ray spectra ("inelastic", or "capture", or "activation" gamma-ray spectra), sonic transit times or velocities, and NMR relaxation time or diffusion constant distributions. MWD and LWD instruments often have components similar in function to those provided in wireline tools (e.g. transmitting and receiving antennas), but MWD and LWD tools are conventionally constructed to operate in the harsh and hostile downhole drilling environment. The terms MWD and LWD are often used interchangeably, and the use of either term in this disclosure will be understood to include both the collection of formation and wellbore information, as well as data on movement, position, and geometry of the drilling assembly.

Well logging instruments may be used to determine formation volumetrics, that is, to quantify the volumetric fraction, which may be expressed as a percentage, of each constituent present in a given sample of formation being evaluated (these constituents which may be thought of as the "elementary building blocks" of the formation, are also called "end-members"). Formation volumetrics may include the identification of the constituents present, and the assigning of unique responses or "signatures" for each or any of such constituents with-respect-to the different log measurements considered (the signatures of these end-members, are also called "end-points"). Together with a corresponding "earth model", and the considered measurements "mixing-laws", the logging instruments' measurements may then be converted into elemental volumetric fractions of one or more constituents. The term "earth model" refers to the geometrical or spatial layout and disposition of various constituents with respect to one another, and the term "mixing-laws" refers to how particular log measurement readings behave or change, with the changing percentages of the constituents present (when the change follows a linear relationship, the mixing-laws are said to be linear).

SUMMARY

This summary is provided to introduce a selection of concepts that are further described below in the detailed description. This summary is not intended to identify key or essential features of the claimed subject matter, nor is it intended to be used as an aid in limiting the scope of the claimed subject matter.

A well-logging method for a geological formation having a borehole therein may include collecting a plurality of nuclear magnetic resonance (NMR) snapshots from the borehole indicative of changes in the geological formation and defining NMR data. The method may further include identifying a plurality of fluids within the geological formation based upon the NMR data, determining respective NMR signatures for the identified fluids based upon the NMR data, determining apparent volumes for the identified fluids based upon the NMR signatures, and determining adjusted volumes for the identified fluids based upon the apparent volumes.

A related well-logging system may include a well-logging tool to collect a plurality of nuclear magnetic resonance (NMR) snapshots from a borehole in the geological formation indicative of changes in the geological formation and defining NMR data. A processor may also be included to identify a plurality of fluids within the geological formation based upon the NMR data, determine respective NMR signatures for the identified fluids based upon the NMR data, determine apparent volumes for the identified fluids based upon the NMR signatures, and determine adjusted volumes for the identified fluids based upon the apparent volumes.

A non-transitory computer-readable medium is also provided. The computer-readable medium may have computer-executable instructions for causing a computer to identify a plurality of fluids within a geological formation based upon a plurality of nuclear magnetic resonance (NMR) snapshots from a borehole within the geological formation indicative of changes in the geological formation and defining NMR data, determine respective NMR signatures for the identified fluids based upon the NMR data, determine apparent volumes for the identified fluids based upon the NMR signatures, and determine adjusted volumes for the identified fluids based upon the apparent volumes.

used for the case of true normalization, in accordance with an example embodiment.

Figure 2:
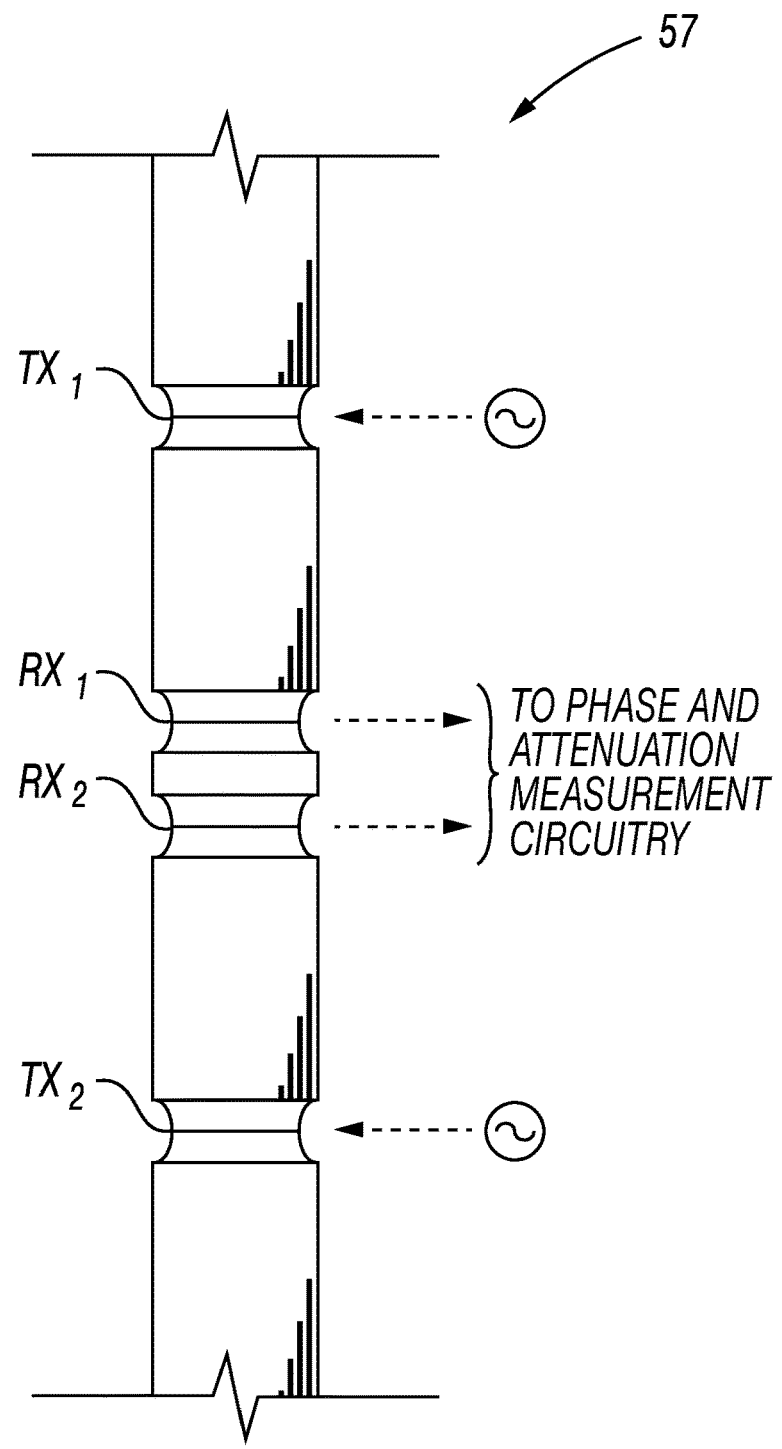
FIG. 2 is a diagram of an example electromagnetic well logging instrument or tool which may be used with the system of FIG. 1.
Figure 2A:
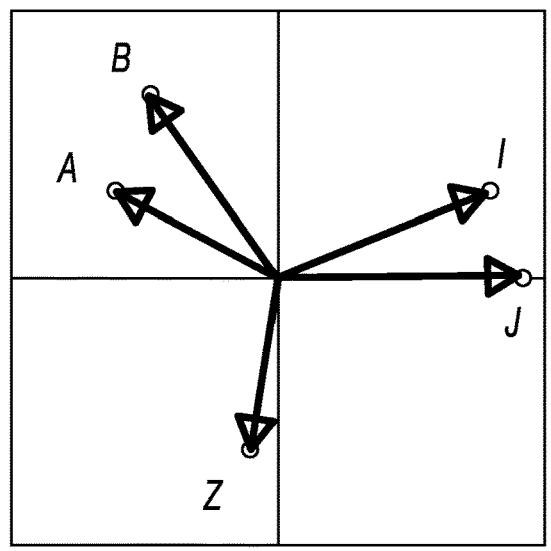
FIG. 2A is a plot of example conventional overlays displaying individual well log instrument responses (the "vectors") of each constituent in a formation, in accordance with this disclosure.
Figure 16A:
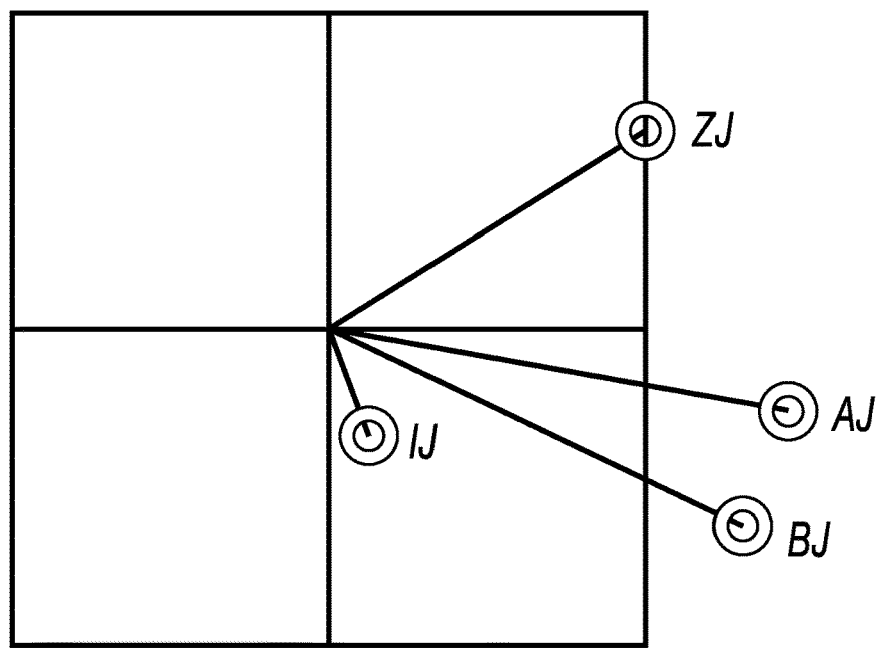
FIG. 16A is a diagram which displays the vectors $$\frac{\Delta_{ij}(\vec{M})}{\Delta_{ij}(V_J)}$$
Figure 16B:
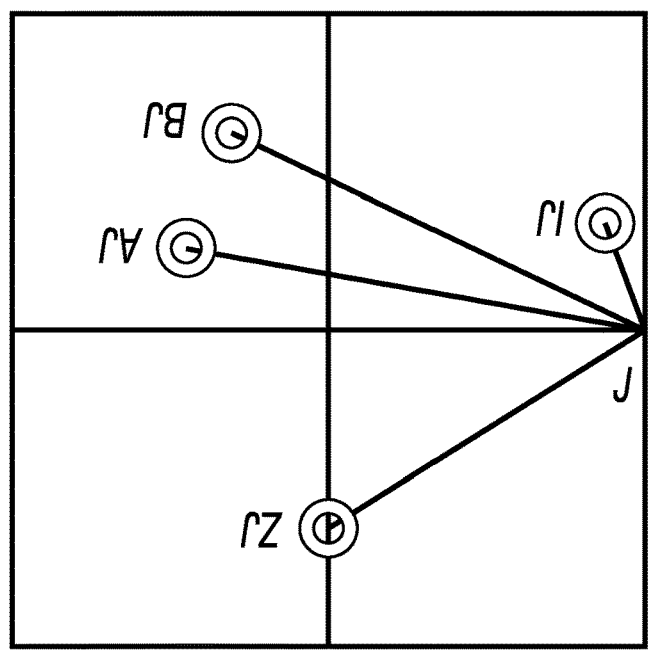

FIG. 16B is a diagram which displays the relationship(s)

$$\vec{M}_I = \vec{M}_J - \frac{\Delta_{ij}(\vec{M})}{\Delta_{ij}(V_J)}$$

versus FIG. 2A used for the case of true normalization.

Figure 16C:
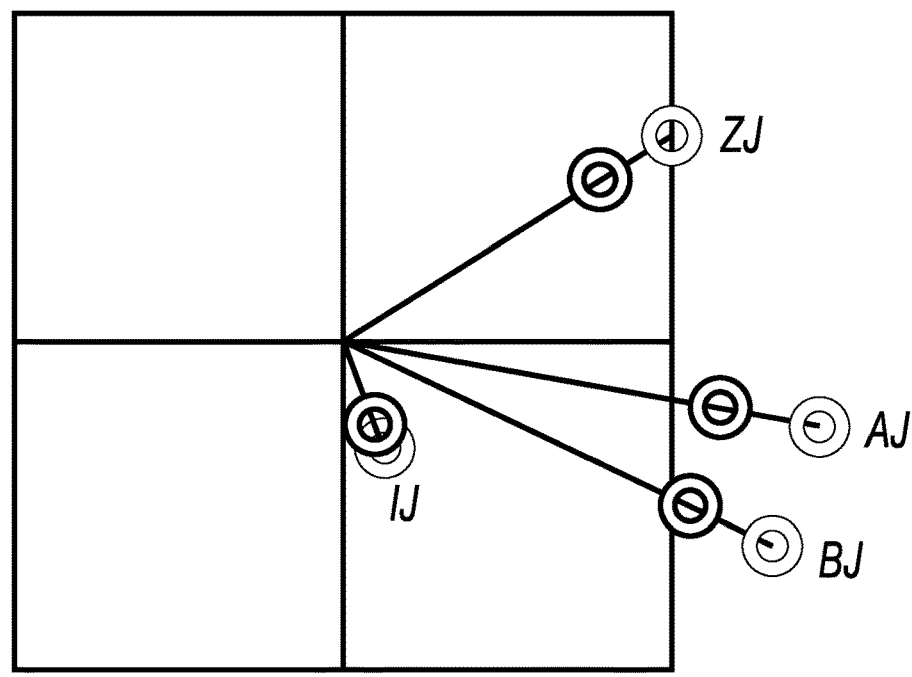

FIG. 16C is a diagram which displays the vectors $$\frac{\Delta_{ij}(\tilde{M})}{\Delta_{ij}(V_J)^{apparent}},$$

used for the case of apparent normalization.

Figure 16D:
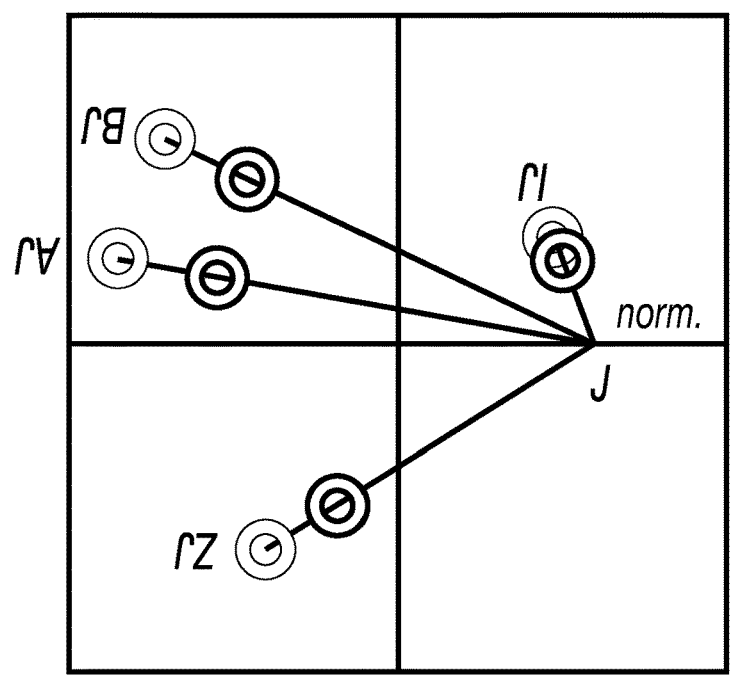

FIG. 16D is a diagram which displays the relationship(s)

$$\tilde{M}_J^{norm.} - \frac{\Delta_{ij}(\tilde{M})}{\Delta_{ij}(V_J)^{apparent}}$$

versus FIG. 2A, used for the case of apparent normalization.

Figure 17A:
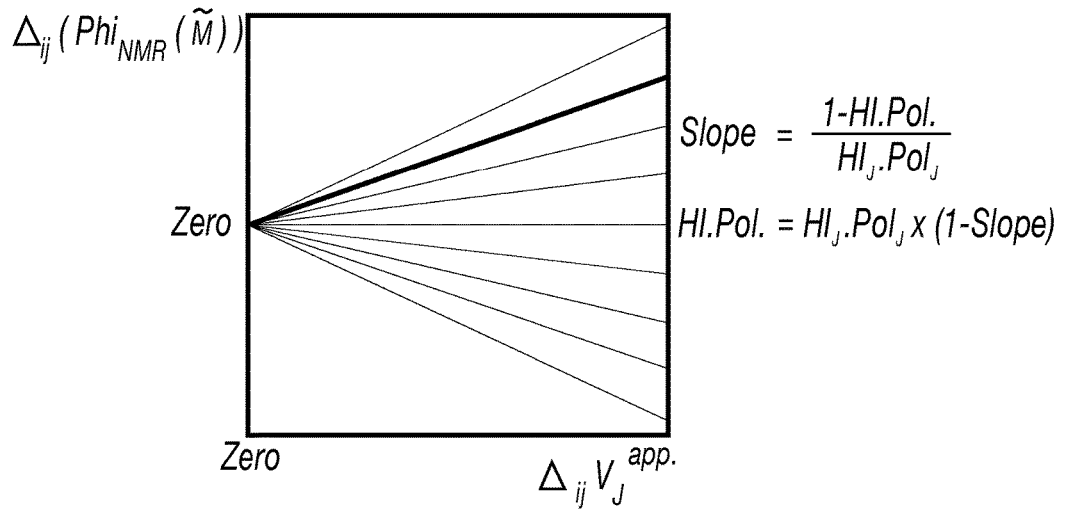

FIG. 17A is a diagram which illustrates a new family of cross-plots, with $\Delta_{ij}(V_J)^{apparent}$ as the "X axis" and $\Delta_{ij}$ (Phi($\tilde{M}$)) as the "Y axis".

Figure 17B:
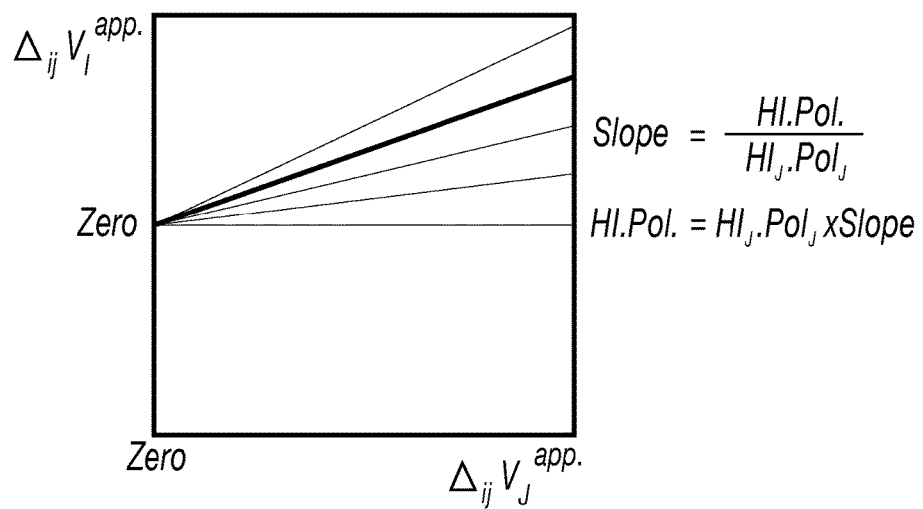

FIG. 17B is a diagram which illustrates a cross-plot with $\Delta_{ij}(V_J)^{apparent}$ as the "X axis" and $\Delta_{ij}(V_J)^{apparent}$ as the "Y axis", in which case the various slopes would read $$\frac{HI_I \cdot Pol_I}{HI_J \cdot Pol_J}.$$

Figure 18:
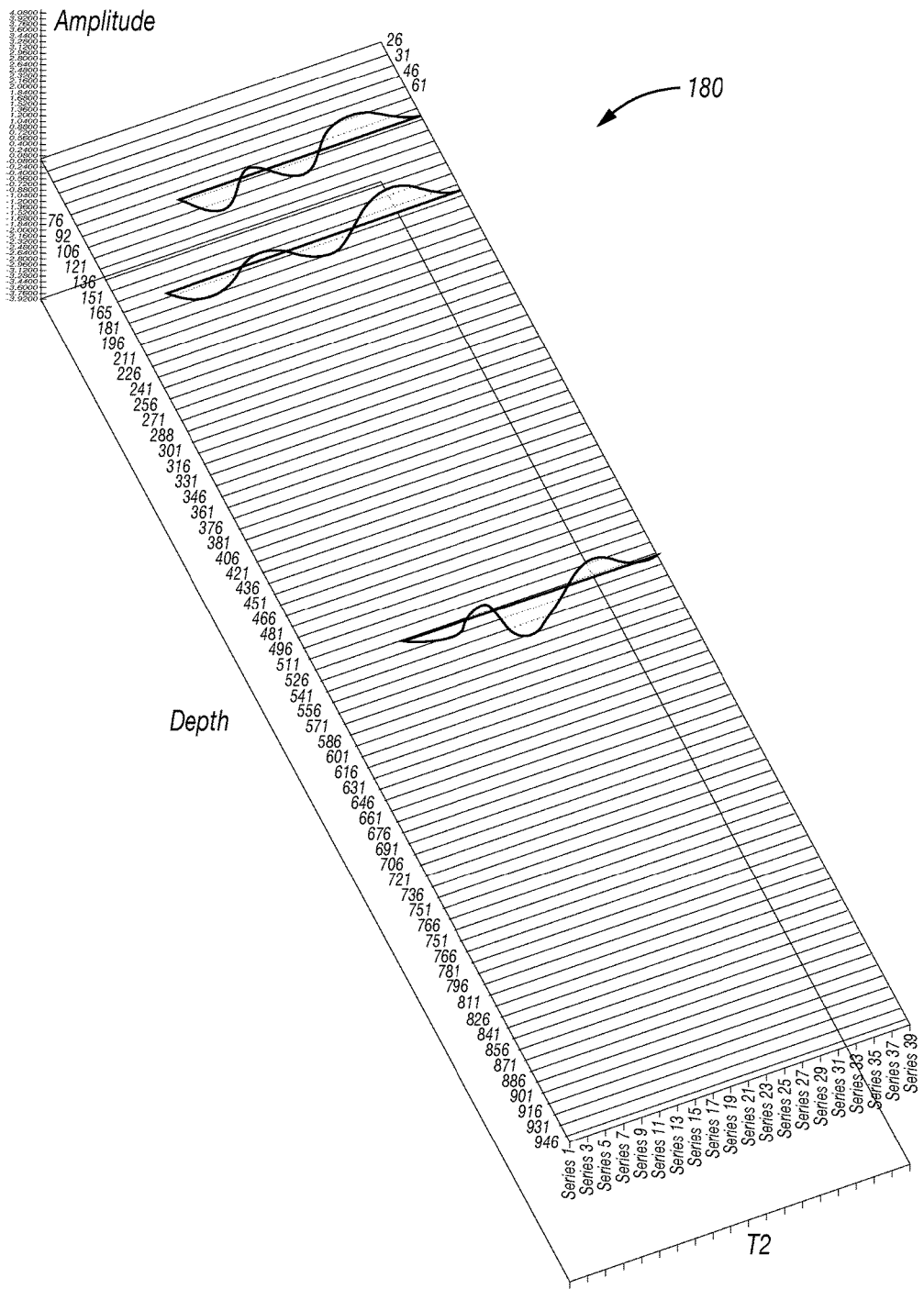

FIG. 18 is a plot illustrating pseudo-normalization results in which the norm is taken to be $\|\tilde{u}\| = FF_{T2\ cutoff\ 90\ msec}^{wipe}$, and where those data points with norm above a preset noise threshold $\|\Delta_{ij}(\tilde{M})\| \gg 75\% \|\Delta_{ij}(\tilde{M})\|_{Max}$ are displayed, in accordance with an example embodiment.

Figure 19:
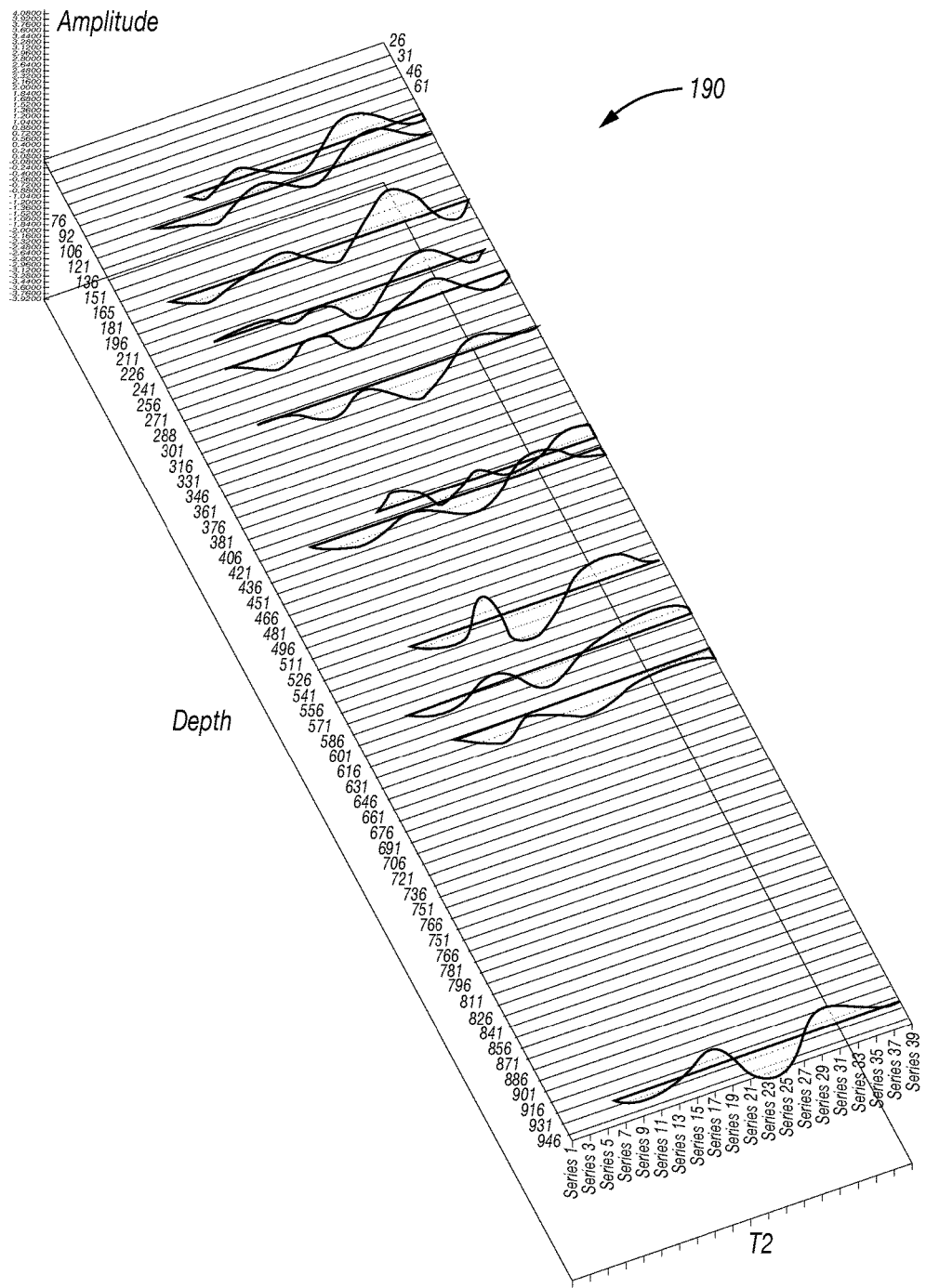

FIG. 19 is a plot illustrating pseudo-normalization results, where the norm is taken to be $\|\tilde{u}\| = FF_{T2\ cutoff\ 90\ msec}^{wipe}$, and where those data points with norm above a preset noise threshold $\|\Delta_{ij}(\tilde{M})\| \gg 63\% \|\Delta_{ij}(\tilde{M})\|_{Max}$ are displayed, in accordance with an example embodiment.

Figure 20:
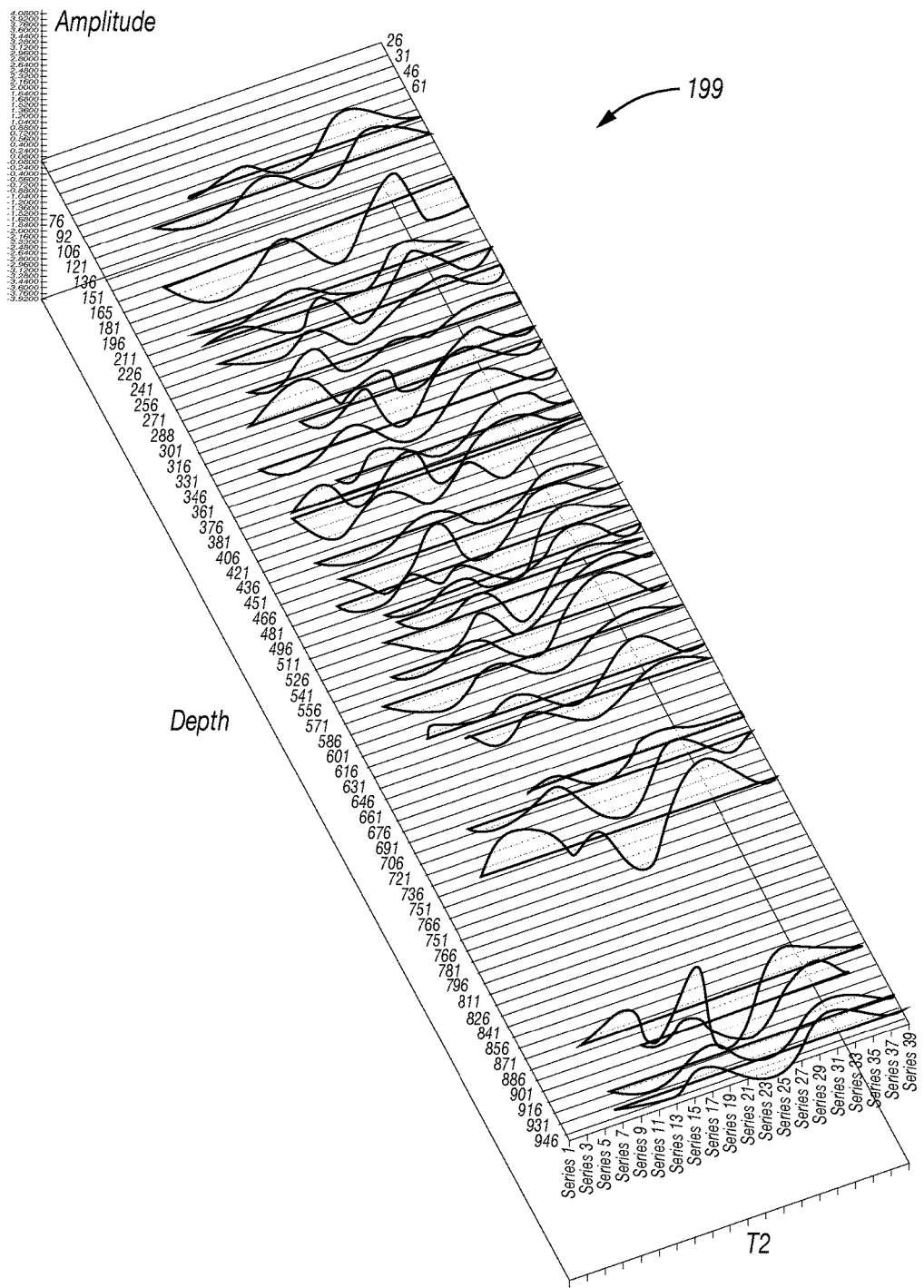

FIG. 20 is a plot illustrating pseudo-normalization results, where the norm is taken to be $\|\tilde{u}\| = FF_{T2\ cutoff\ 90\ msec}^{wipe}$, and where those data points with norm above a preset noise threshold $\|\Delta_{ij}(\tilde{M})\| \gg 50\% \|\Delta_{ij}(\tilde{M})\|_{Max}$ are displayed, in accordance with an example embodiment.

Figure 21:
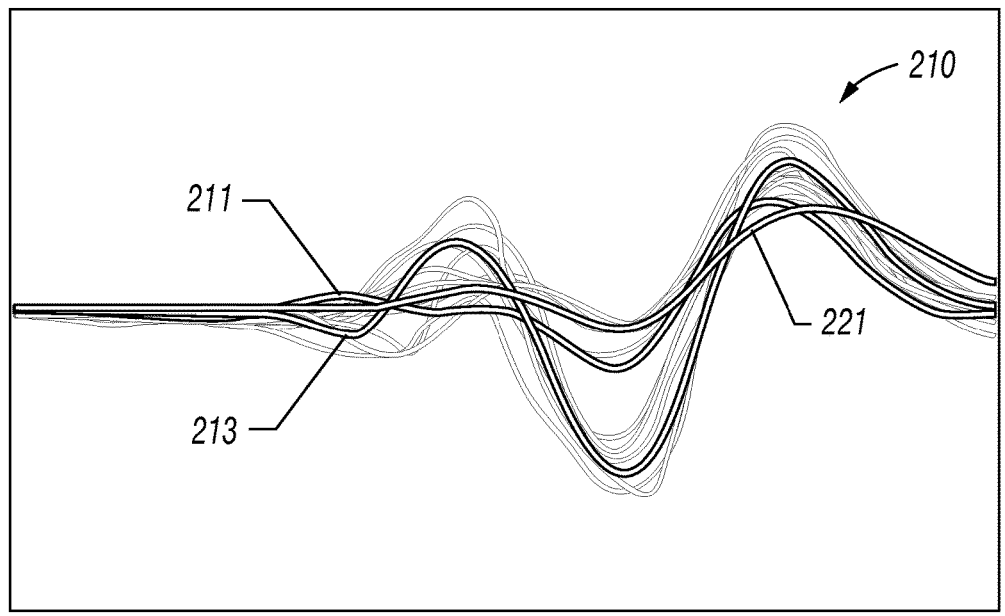

FIG. 21 is a plot showing clusters of true normalized (in contradistinction to pseudo-normalized) patterns corresponding to different x-constituent pair exchanges, where $FF_{T2\ cutoff\ 90\ msec}^{wipe}$ was equated with the volume of drilling OBM filtrate participating in the x-constituent pair exchanges, in accordance with an example embodiment.

Figure 22:
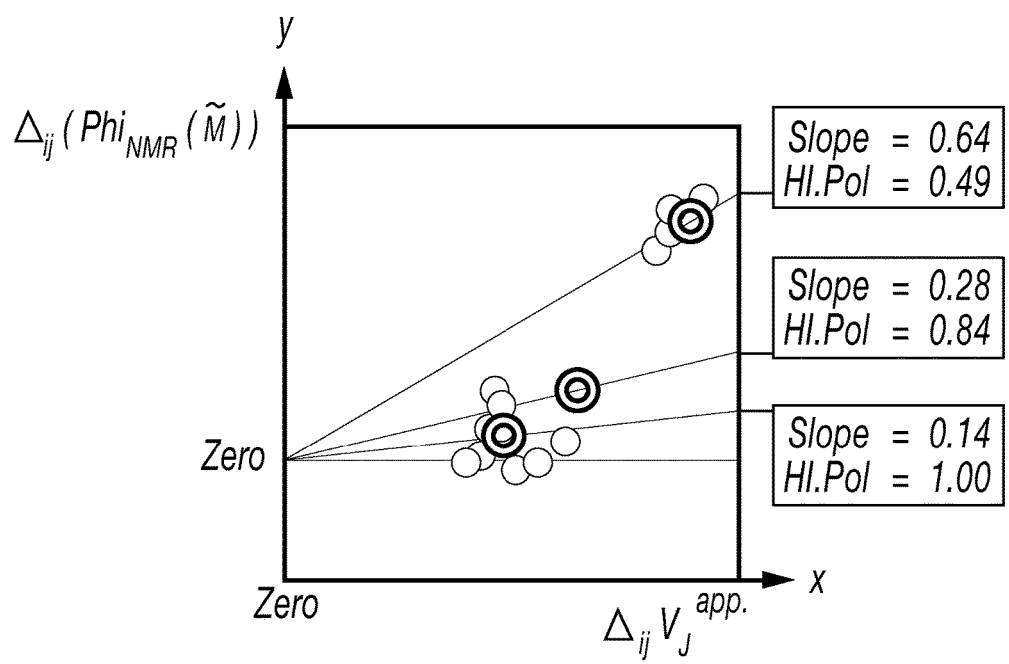

FIG. 22 is a graph illustrating how the combined effects of hydrogen index and polarization factor are identified and then adjusted, in accordance with an example embodiment.

Figure 23:
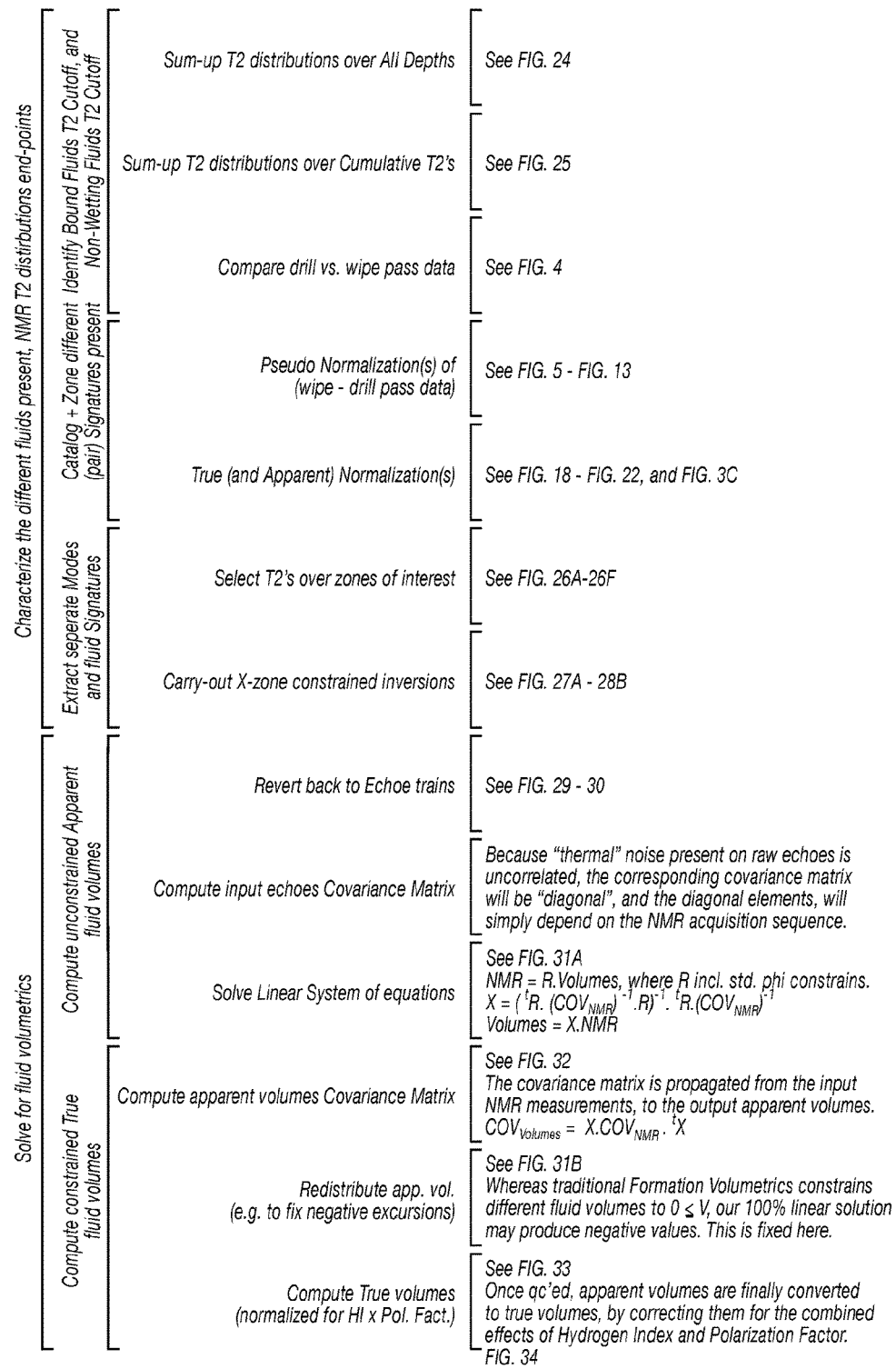

FIG. 23 is a flow chart for an example fluid volumetrics method in accordance with an example embodiment.

Figure 24:
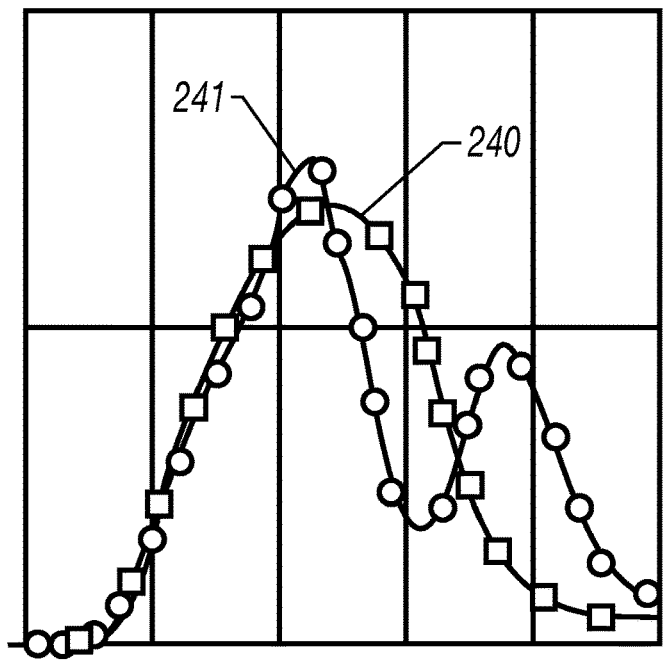
Figure 25:
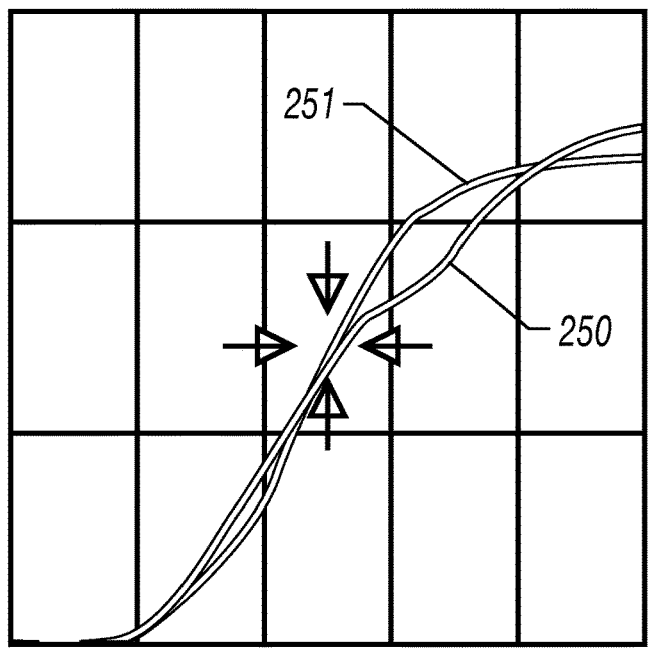
Figure 26A:
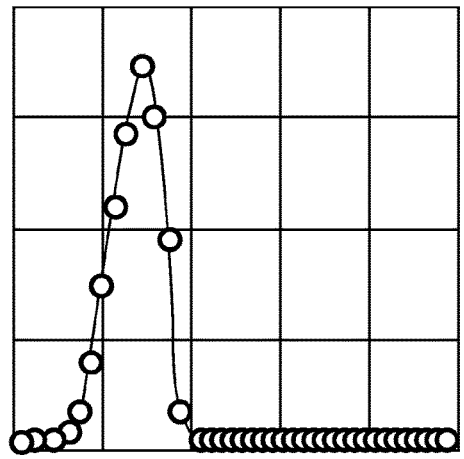
Figure 26B:
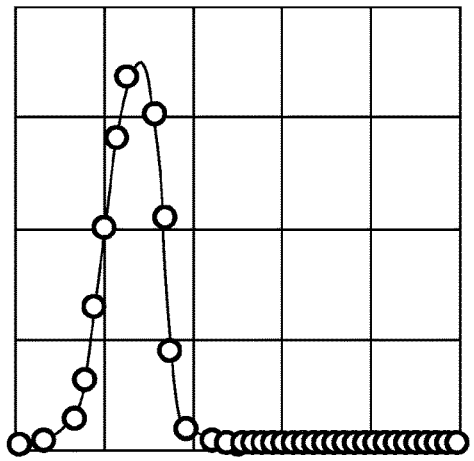
Figure 26C:
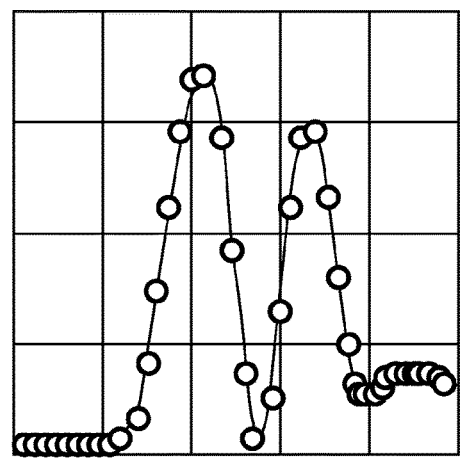
Figure 26D:
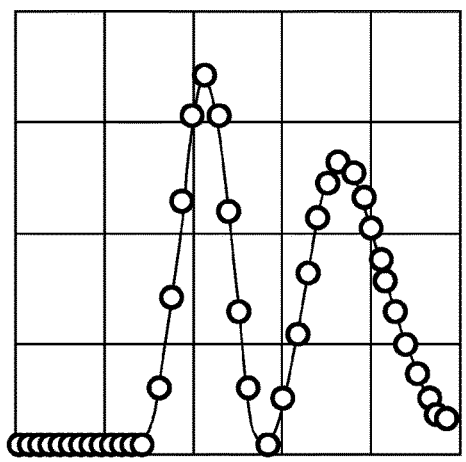
Figure 26E:
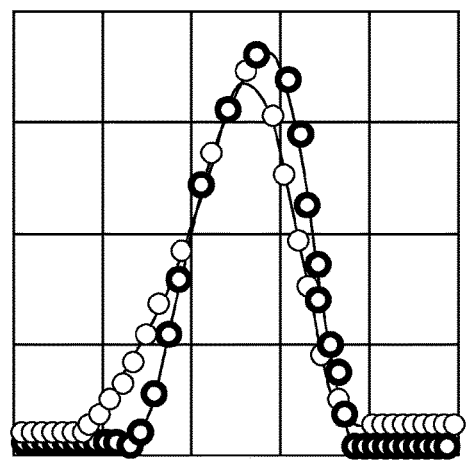
Figure 26F:
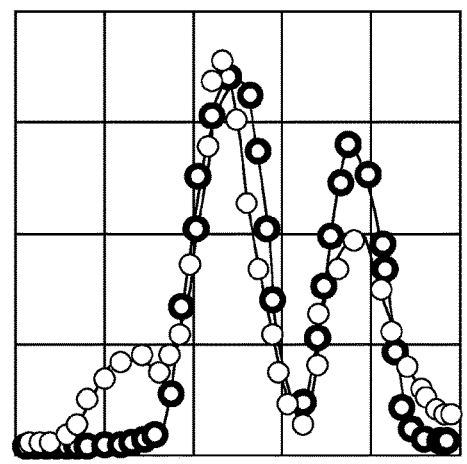
Figure 27A:
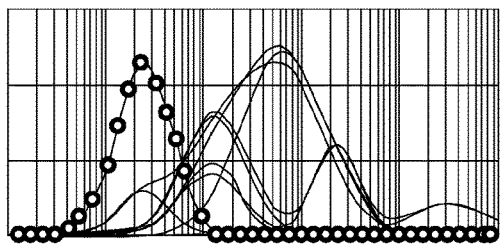
Figure 27B:
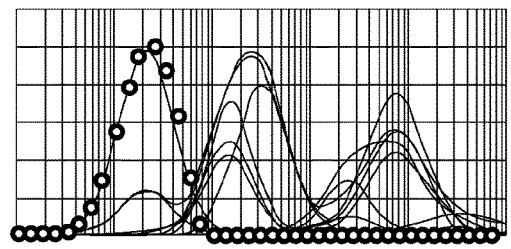
Figure 27C:
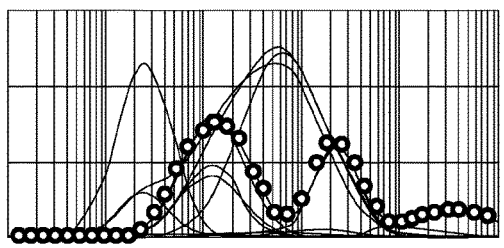
Figure 27D:
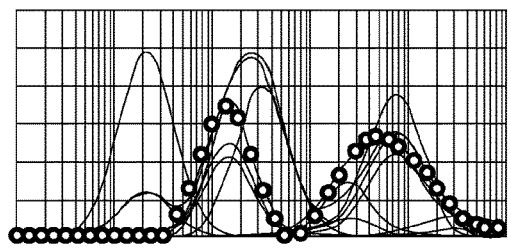
Figure 27E:
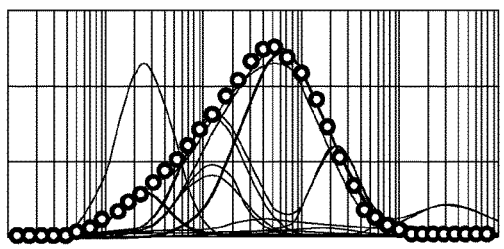
Figure 27F:
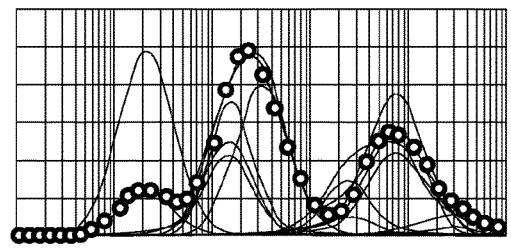
Figure 27G:
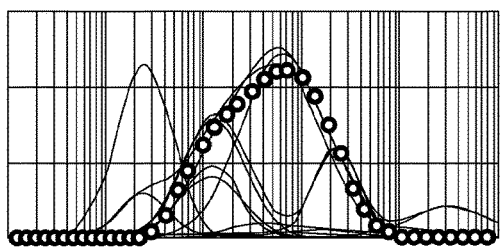
Figure 27H:
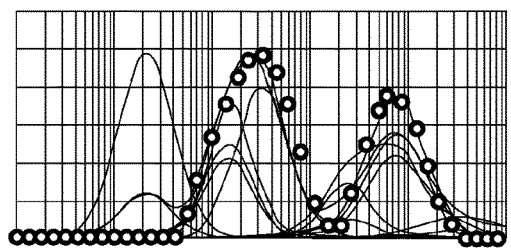

FIGS. 24 and 25 are graphs showing a $T_2$ distribution integration over depth, followed by integration over "cumulative" $T_2$'s, respectively, in accordance with an example embodiment.

FIGS. 26A through 26F are graphs showing $T_2$ distributions selected over zones of interest, and from different passes (drill & wipe pass) for a cross-zone constrained mode extraction, in accordance with an example embodiment.

Figure 28A:
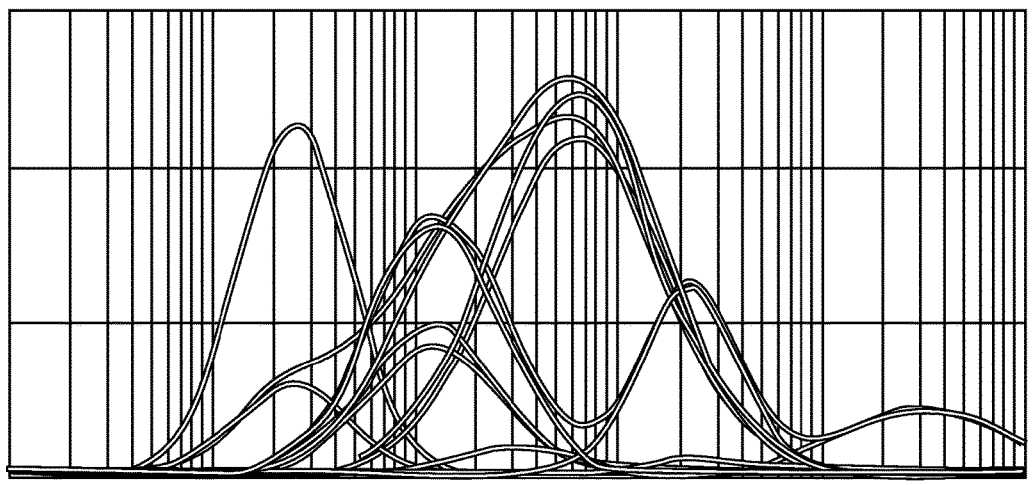
Figure 28B:
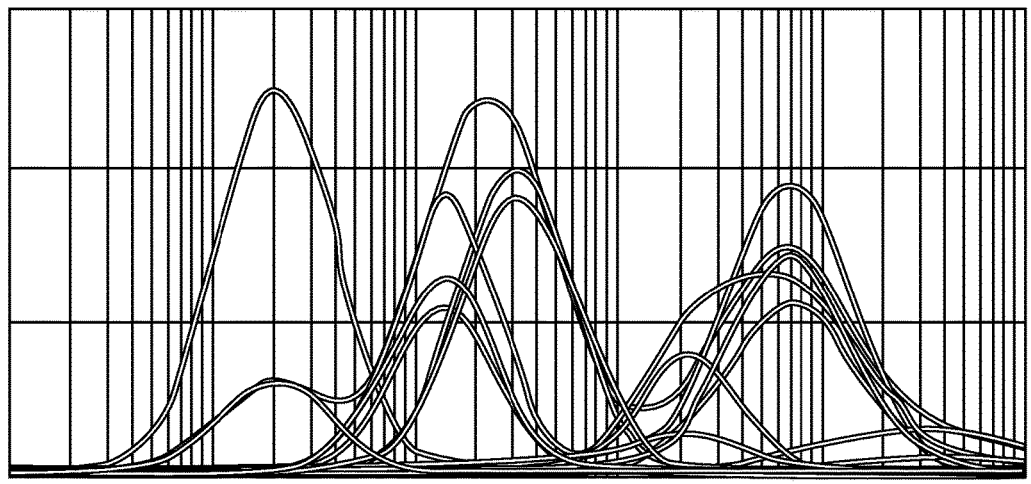

FIGS. 27A through 27H are plots illustrating fit results from different zones and passes (drill & wipe pass) displayed together, including the underlying extracted Gaussian modes shown in the graphs of FIGS. 28A and 28B.

Figure 29:
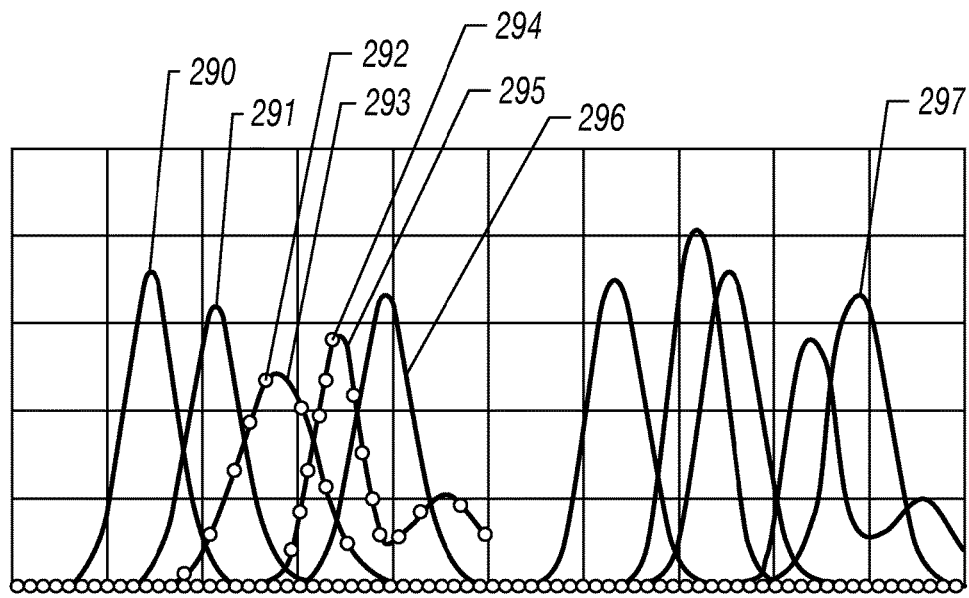
Figure 30:
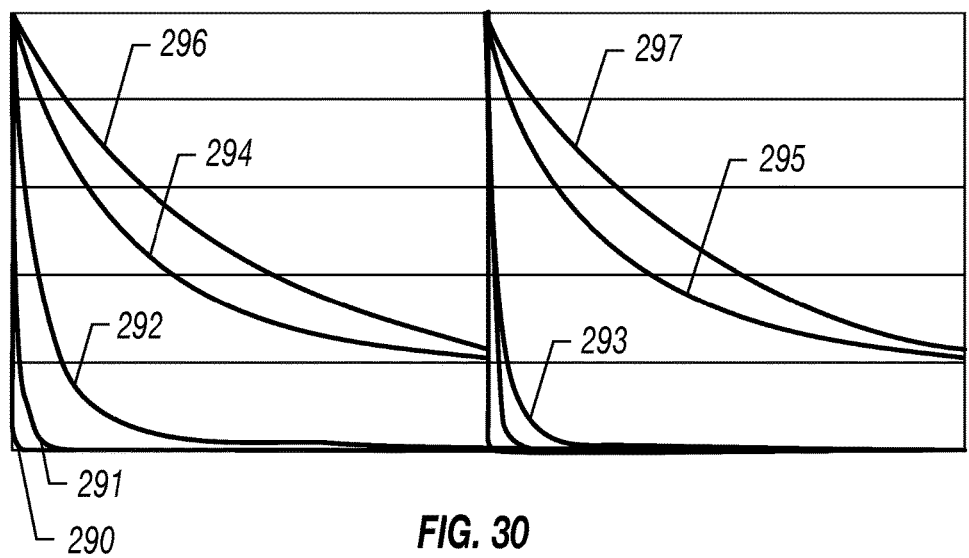

FIGS. 29 and 30 graphs summarizing different fluid constituents' NMR "concatenated" apparent signatures, normalized to one (i.e. 100 p.u.), in accordance with an example embodiment.

Figure 31A:
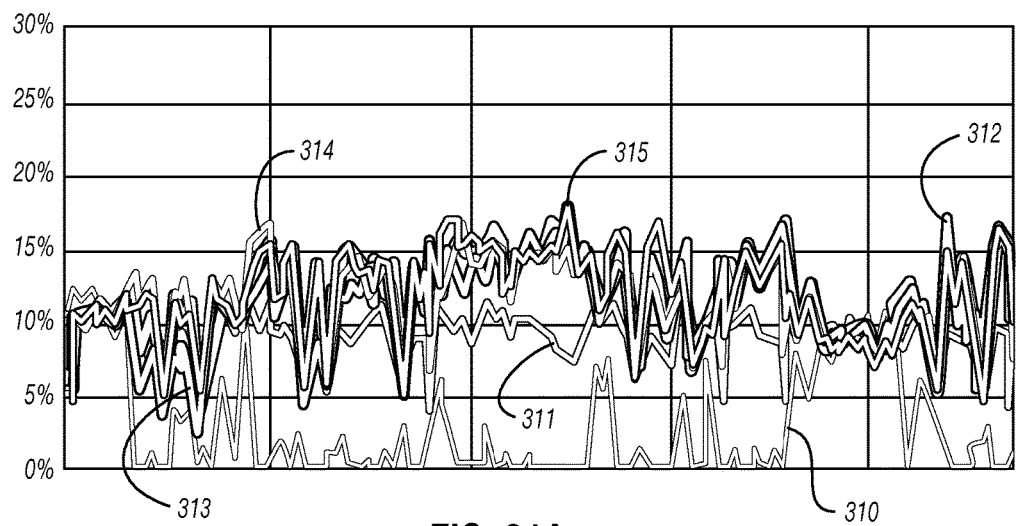

FIG. 31A is a graph showing a fluid elemental volumetric analysis solving for "apparent" fluid volumes, in accordance with an example embodiment.

Figure 31B:
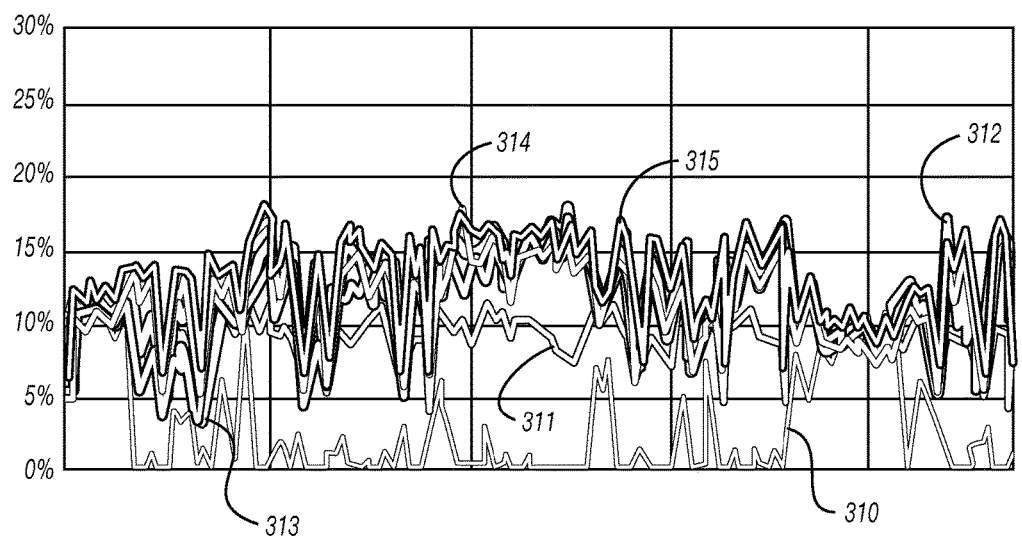
Figure 32:
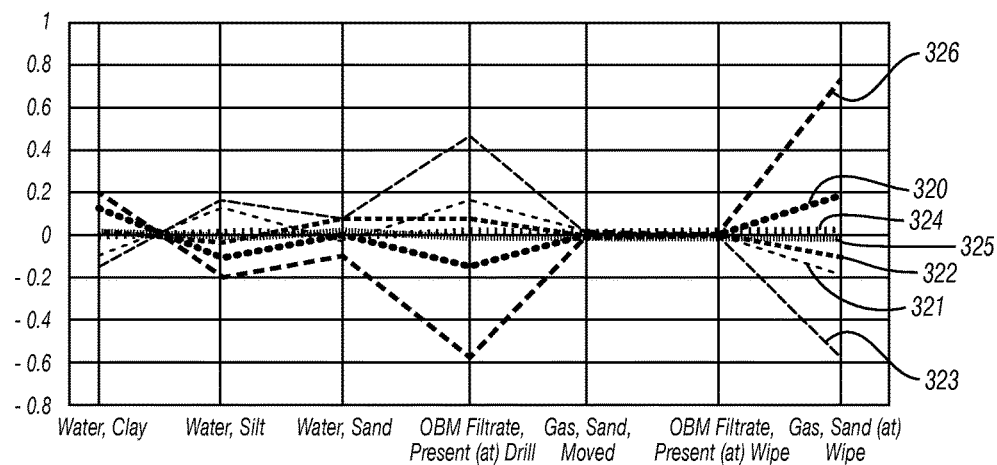

FIG. 31B is a graph showing a fluid elemental volumetric analysis solving for "adjusted" apparent fluid volumes, after redistributing negative values, using the covariance matrix from FIG. 32.

FIG. 32 is a visual representation of the covariance matrix of the computed "apparent" volumes, in accordance with an example embodiment.

Figure 33:
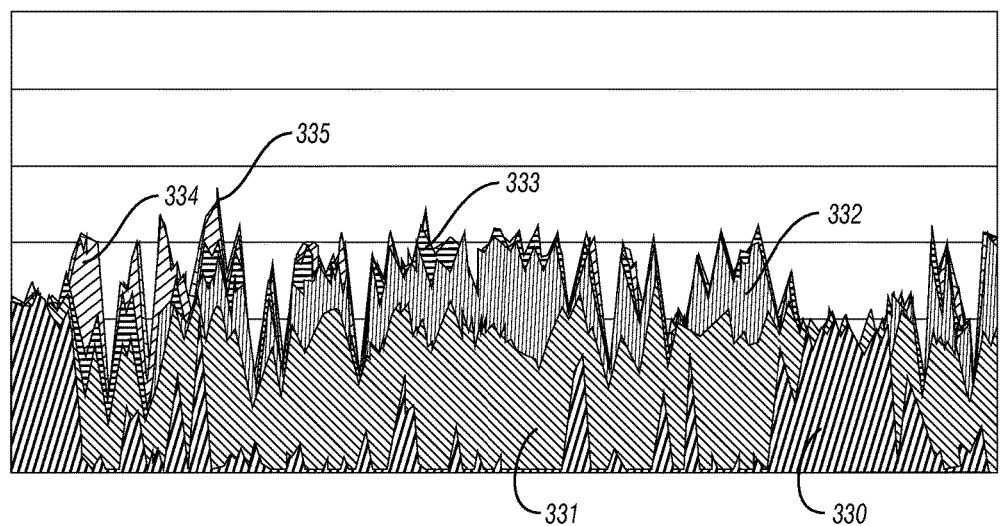

FIG. 33 is a plot showing an example final fluid volumetric analysis, solving for "true" fluid volumes, after correcting the adjusted apparent fluid volumes for the corresponding combined effects of hydrogen index and (HI) polarization factor.

Figure 34:
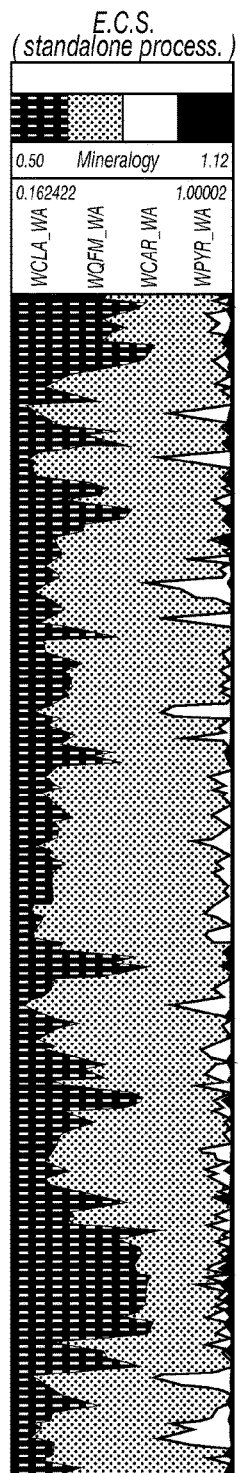
Figure 34:
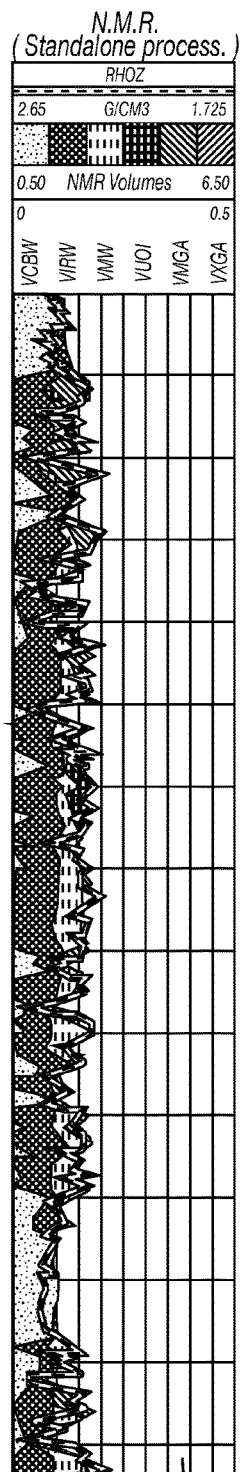
Figure 34:
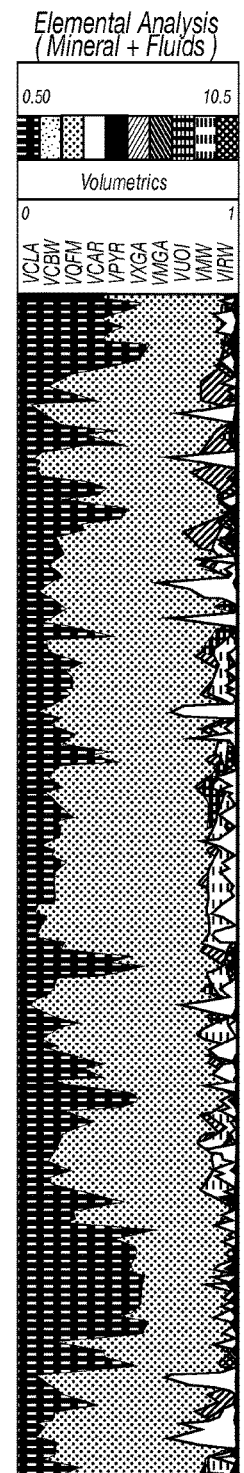
Figure 35:
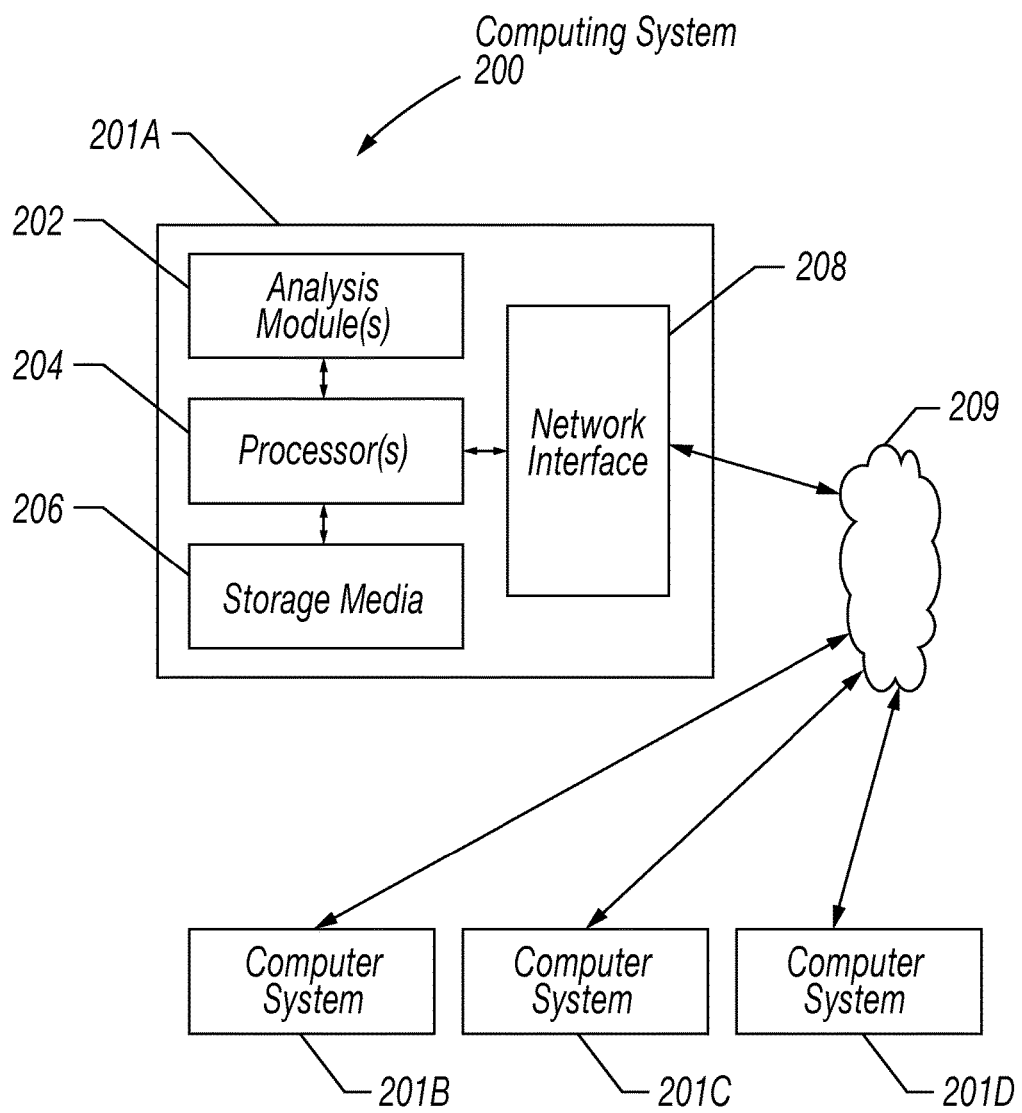

FIG. 34 are plots summarizing the merging of the final fluid volumetric analysis, and rock mineralogy results from elemental thermal neutron capture spectroscopy data, into an integrated volumetric elemental analysis that accounts for the fluid and matrix constituents present, in accordance with an example embodiment FIG. 35 is a schematic diagram of an example computer system which may be used to implement various operations described herein.

Figure 1:
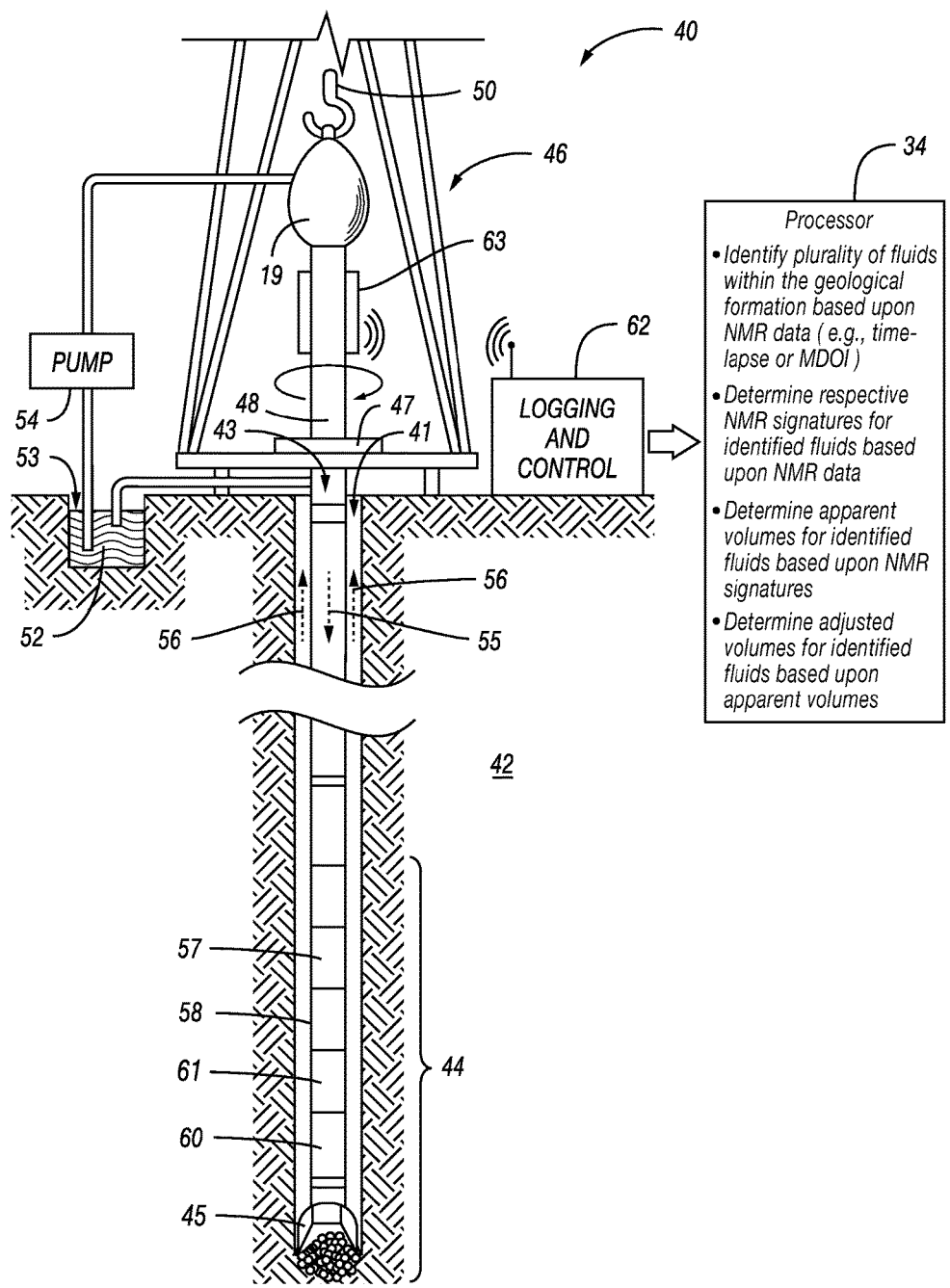
FIG. 1 is a schematic diagram illustrating a well-logging system in accordance with an example embodiment.
Figure 36:
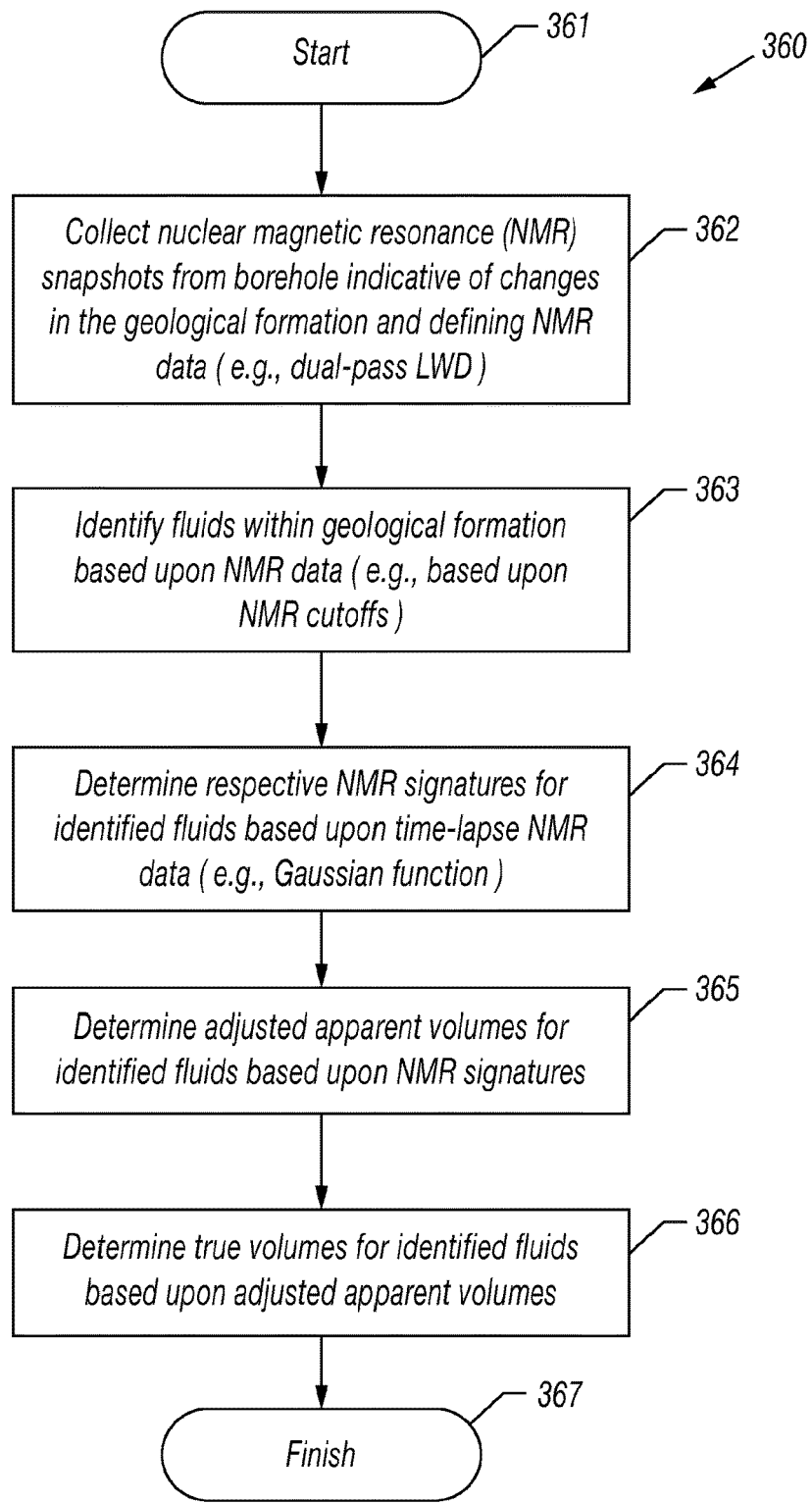

FIG. 36 is a flow diagram illustrating example method aspects associated with the system of FIG. 1.

DETAILED DESCRIPTION

The present description is made with reference to the accompanying drawings, in which example embodiments are shown. However, many different embodiments may be used, and thus the description should not be construed as limited to the embodiments set forth herein. Rather, these embodiments are provided so that this disclosure will be thorough and complete. Like numbers refer to like elements throughout.

Generally speaking, a well-logging method is set forth herein for a geological formation having a borehole therein, which may include collecting nuclear magnetic resonance (NMR) snapshots, such as time-lapse or multi-depth-of-investigation (MDOI) NMR snapshots, indicative of changes in the geological formation. The method may further include taking the difference between different data acquired at different times or from different depths—of investigation (DOI's), and identifying a plurality of fluids within the geological formation—including such fluids' combined "hydrogen index" (HI) and "polarization factor" signature—based upon the collected NMR data, which may include pseudo- or true "normalization" techniques, and statistical analysis techniques using multi-dimensional histograms (e.g. NMR distributions histograms), or neural network (NN) classification schemes, or factor analysis or principal component analysis (PCA) to identify cross-constituent substitution signatures, and which may include determining NMR distribution "cutoffs" in-situ. The method may further include determining respective NMR "apparent", "true", and "effective concatenated" NMR signatures for the identified fluids based upon the time-lapse or MDOI NMR data—$T_2$ distributions for example—and using curve fitting techniques (constrained or not), or factor analysis or PCA (constrained or not), or computing the intersection of two or more lines joined at the same point in two- or more dimensional space, determining apparent volumes for the identified fluids based upon the $T_2$ signatures and using concatenated NMR data or the corresponding "raw echoes", determining adjusted apparent volumes for the identified fluids based upon the apparent volumes and using the covariance of the apparent volumes, and determining true volumes for the identified fluids based upon the adjusted apparent volumes and the identified fluids "hydrogen index" (HI) and "polarization factor". The method may further include identifying an NMR porosity space, which may be represented by a set of factors which may also be presented as a distribution with the same number of components as the NMR T2 distributions concerned, based upon the collected NMR data and at least one of the identified non-wetting fluids T2 signatures or wetting fluids effective T2 signatures (e.g., group signatures), determining a snapshot-independent apparent NMR porosity (independent of fluid type) based upon the identified NMR porosity space and the collected NMR data, collecting well-logging data indicative of the geological formation mineralogy (such as Thermal Neutron Capture Spectroscopy or Mud Logging data) and determining a shapshot-independent true NMR porosity corrected for the matrix mineralogy, based upon the computed snapshot-independent apparent NMR porosity.

A related well-logging system and non-transitory computer-readable medium are also provided. As used herein, the expression "NMR data" used throughout this summary, is meant in a generic fashion, to accommodate the breadth of NMR sequences possible. Furthermore, present-day NMR data using "CPMG sequences" ("Carr Purcell Meiboom Gill" sequences) conventionally include "raw echoes", which may then be converted into "window sums", which in turn may then be converted as the case may be into one-dimensional "longitudinal relaxation time" distributions (so called "T1" distributions), or one-dimensional "transverse relaxation time" (so called "T2" distributions), or one-dimensional "diffusion constant distributions", or a multi-dimensional combination thereof (in this case the expression "distribution" may be interchanged with the expression "map"), which may in turn be used to compute NMR "porosity bins". These are linearly related to each other, and the expression "NMR data" will therefore be understood to encompass raw echoes, window sums, distributions or maps, and porosity bins, for example.

FIG. 1 illustrates a well site system 40 in which various embodiments may be implemented. In the illustrated example, the well site is a land-based site, but the techniques described herein may also be used with a water, swamp or offshore-based well site as well. In this example system, a borehole 41 is formed in a subsurface or geological formation 42 by rotary drilling, for example. Some embodiments may also use directional drilling, as will be described below.

A drill string 43 is suspended within the borehole 41 and has a bottom hole assembly (BHA) 44 which illustratively includes a drill bit 45 at its lower end. The system 40 further illustratively includes a platform and derrick assembly 46 positioned over the borehole 41. The assembly 46 illustratively includes a rotary table 47, kelly 48, hook 50 and rotary swivel 51. The drill string 43 may be rotated by the rotary table 47 which engages the kelly 48 at the upper end of the drill string. The drill string 43 is illustratively suspended from the hook 50, which is attached to a traveling block (not shown), through the kelly 48 and the rotary swivel 51 which permits rotation of the drill string relative to the hook. A top drive system (not shown) may also be used to rotate and axially move the drill string 43, for example.

In the present example, the system 40 may further include drilling fluid or mud 52 stored in a pit 53 formed at the well site (or a tank) for such purpose. A pump 54 delivers the drilling fluid 52 to the interior of the drill string 43 via a port in the swivel 51, causing the drilling fluid to flow downwardly through the drill string as indicated by the directional arrow 55. The drilling fluid exits the drill string 43 via ports or nozzles (not shown) in the drill bit 45, and then circulates upwardly through an annular space ("annulus") between the outside of the drill string and the wall of the borehole, as indicated by the directional arrows 56. The drilling fluid lubricates the drill bit 45 and carries formation cuttings up to the surface as it is cleaned and returned to the pit 53 for recirculation.

The BHA 44 of the illustrated embodiment may include a logging-while-drilling (LWD) module 57, a measuring-while-drilling (MWD) module 58, a rotary steerable directional drilling system or motor 60, and the drill bit 45.

The LWD module 57 may be housed in a special type of drill collar, as is known in the art, and may include one or more types of well logging instruments. It will also be understood that optional LWD and/or MWD modules 61 may also be used in some embodiments. (References, throughout, to a module at the position of 57 may mean a module at the position of 61 as well). The LWD module 57 may include capabilities for measuring, processing, and storing information, as well as for communicating the information with the surface equipment, e.g. to a logging and control unit 62, which may include a computer and/or other processors for decoding information transmitted from the MWD and LWD modules 57, 58 and recording and calculating parameters therefrom. The information provided by the MWD and LWD modules 57, 58 may be provided to a processor 34 (which may be off site, or in some embodiments may be on-site as part of the logging and control unit 62, etc.) for determining volumetric information regarding constituents within the geological formation 42, as will be discussed further below.

In the present embodiment, the LWD module 57 may include electromagnetic or nuclear or acoustic devices, and a nuclear magnetic resonance (NMR) measurement device similar in configuration to those sold under the trademark proVISION™ or MR Scanner™, which are trademarks of Schlumberger Technology Corporation, Sugar Land, Tex., U.S.A. Signals may be communicated from the drill string 43 to the logging and control unit 62 using a pressure transducer 63 with wired or wireless coupling to the logging and control unit, or by any other form of signal communication known in the art applicable to communication of signals from a wellbore disposed instrument to a surface unit, e.g. "wired" drill pipe (WDP). See, for example, U.S. Pat. No. 6,866,306 issued to Boyle et al. and incorporated herein in its entirety by reference.

The MWD module 58 may also be housed in a special type of drill collar, as is known in the art, and may include one or more devices for measuring characteristics of the drilling environment and parameters, such as drilling mechanics measurements, drilling dynamics measurements, and other downhole conditions. The MWD tool may further include an apparatus (not shown) for generating electrical power to the downhole system. This may include a mud turbine generator powered by the flow of the drilling fluid, it being understood that other power and/or battery systems may be employed. The MWD module 58 may include one or more of the following types of measuring devices: a weight-on-bit measuring device, a torque measuring device, a shock & vibration measuring device, a pressure and/or temperature measuring device, a rotations-per-minute (rpm) measuring device, a mud flowrate measuring device, and a direction and/or inclination measuring device for example.

An example LWD propagation-type resistivity tool 57 is shown in FIG. 2. In the illustrated example, upper and lower transmitting antennas, $TX_1$ and $TX_2$, have upper and lower receiving antennas, $RX_1$ and $RX_2$, therebetween. The antennas are formed in recesses in a modified drill collar and mounted in MC or insulating material. The phase shift of the electromagnetic wave between the receivers provides an indication of formation resistivity at a relatively shallow depth of investigation (and called "phase-shift resistivity" PSR), and the attenuation of the electromagnetic wave between the receivers provides an indication of formation resistivity at a relatively deep depth of investigation (and called "attenuation resistivity" ATR). U.S. Pat. No. 4,899,112 issued to Clark et al., and incorporated herein in its entirety by reference, may be referred to for further details of the foregoing example instrument. In operation, attenuation-representative signals and phase-representative signals are coupled to a processor, an output of which may be coupled to a telemetry circuit.

Some other electromagnetic (EM) logging tools use one or more tilted or transverse antennas, with or without axial antennas. Those antennas may be transmitters or receivers. A tilted antenna is one whose dipole moment is neither parallel nor perpendicular to the longitudinal axis of the tool. A transverse antenna is one whose dipole moment is perpendicular to the longitudinal axis of the tool, and an axial antenna is one whose dipole moment is parallel to the longitudinal axis of the tool. A triaxial antenna is one in which three antennas (i.e. antenna coils) are arranged to be mutually orthogonal. Often one antenna (coil) is axial and the other two are transverse. Two antennas are said to have equal angles if their dipole moment vectors intersect the tool's longitudinal axis at the same angle. For example, two tilted antennas have the same tilt angle if their dipole moment vectors, having their tails conceptually fixed to a point on the tool's longitudinal axis, lie on the surface of a right circular cone centered on the tool's longitudinal axis and having its vertex at that reference point. Transverse antennas have equal angles of ninety degrees, and that is true regardless of their azimuthal orientations relative to the tool.

A system and method to identify and optionally calibrate at least some of a formation constituents' well logging instrument responses ("signatures") from the measurements alone, are described herein. Rather than attempting to identify the signatures (also called "end-points")) of the individual constituents (also called "end-members")—e.g. the fluids and minerals making-up the underground formation, one may attempt to identify patterns resulting from cross-constituent ("x-constituent") substitution. When the substitution occurs in pairs (i.e. when one constituent "I" replaces another constituent "J"), other things remaining equal, the procedure amounts to "benchmarking" one constituent against the other. If one of the constituent's instrument responses are fully characterized, the instrument responses of the other constituent can be inferred.

Consonant measurements (i.e. either "truly" consonant or "effectively" consonant) may be exploited. Truly consonant measurements are defined as those measurements with similar depth-of-investigation (DOI), and hence equally affected by "mud-filtrate invasion" for example ("mud-filtrate invasion" refers to the movement and penetration of drilling fluids into the pore spaces of the formation, with such pore space network acting like a filter that leaves out the solids present in the composition of the drilling fluids, and the invading filtrate displacing native formation fluids). Thermal Neutron Capture Cross-Section (also called "SIGMA"), Neutron-Gamma Density (also called "NGD"), and Thermal Neutron Porosity (such "TNPH" or "BPHI") measurements from the EcoScope™ tool from Schlumberger Technology Corporation, may be considered truly consonant measurements. Effectively consonant measurements are defined as those measurements with different DOI's, and yet equally affected by mud-filtrate invasion for example, by way of processing "focusing" means, such as "invasion correction techniques, or they may arise because the well logging measurements were made in the same type of formation, even though the actual DOI's may be different. For example, such is the case when the measurements are affected very little by invasion and reading overwhelmingly in the "virgin zone" (the zone undisturbed by mud-filtrate invasion), or are affected very much by invasion and reading overwhelmingly in the "flushed zone" (the zone spoiled by mud-filtrate invasion). The formation present at a particular depth may be measured and log measurements datasets collected twice or more at different times or at different DOI's (each such log measurements dataset collected will be referred to collectively in the following as a "snapshot") when changes in formation composition are expected to occur, for example because of mud-filtrate invasion. To characterize such change(s) that may have taken place, measurements from the same snapshot may be consonant, however measurements from across different snapshots do not have to be consonant with one another. Measurements may be simultaneously truly consonant and effectively consonant, when they have both similar DOI, and they are also representative of the flushed zone or the virgin zone. Because NMR data in its various forms (i.e. whether raw echoes, or window sums, or distributions, or porosity bins are concerned) may be regarded to include many "components" each of which may be considered as a separate and distinct measurement, NMR type data constitutes the ideal truly consonant measurements dataset. Additionally, when "gradient-type" NMR devices are considered (such as the proVISION™ or MR Scanner™ tools quoted earlier), the NMR "resonant volume" will be a thin cylindrical shell surrounding the tool, which may be either virtually "blind to" (i.e. "unaffected by") mud-filtrate invasion with shallow invasion remaining under the NMR measurement DOI, or totally affected by mud-filtrate invasion with deeper invasion exceeding the NMR measurement DOI, and the NMR data in this case may be considered both truly and effectively consonant.

It may be observed, upon first impression, as if the problem would grow more complex by proceeding to identify patterns resulting from x-constituent substitution, and as compared to the number of constituents present, but that is not the case. For example, for "Z" constituents present, there would be "Z×(Z−1)" x-constituent pair exchanges possible which is much larger than "Z" ("Z×(Z−1)" ordered pairs or half as many disordered pairs), but, in nature and in practice, a very small number of such x-constituent pair exchanges will be relevant to the case at hand. As a result of fluid migration and substitution over a geological time scale, and because different fluids "relative permeability" in a reservoir increases with the "saturation" of the corresponding fluid, presently existing native fluids distribution inside underground formations are such that, at any one depth within such formations, one of the native formation fluids in place is predominantly movable the others having already been displaced over geologic time after sediment deposition and burial, and hydrocarbon maturation and migration. In addition, any intrusive fluid disturbing or modifying the original reservoir fluid "balance" (i.e. the geological time-scale equilibrium fluid distribution) may be known since it may be either injected from the surface or produced to the surface.

On the other hand, it is generally difficult to directly isolate the signature of individual fluid constituents because they may not be present on their own, or they may not be available in a sufficient amount in the volume of formation measured by the logging instruments, despite the reservoir balance discussed above. This is generally the case for "overbalance" drilling operations (i.e. wherein the hydrostatic pressure of the drilling fluid exceeds the native formation fluids pressure), and this problem is exacerbated in conventional wireline logging. Should "underbalance" drilling be considered instead (wherein the hydrostatic pressure of the drilling fluid is less than the native formation fluids pressure), or should the well log measurements considered be suitable for existing invasion correction techniques (such as per the method described in U.S. Pat. No. 8,005,618 B2 entitled "Logging While Drilling System", and issued to Kais Gzara, which is hereby incorporated herein in its entirety by reference), then the situation would be different, and one prevalent fluid constituent would contribute the most to the logging instruments measurements. However, even in such situation, the lack of information on the precise quantity of that fluid constituent present would represent an impediment to deriving the well log response characteristics of that fluid. Furthermore, when studying the patterns resulting from x-constituent substitution, the other unchanged constituents remaining in place, may have their contribution to the logging instruments measurements cancel out, which reduces the complexity that would otherwise result from trying to solve for a plurality of constituents at the same time. And in case of x-constituent substitution in pairs, the pattern resulting from x-constituent substitution is simply related to the log measurements signature of the displaced constituent subtracted from the log measurements signature of the displacing constituent.

A particular situation arises when the log measurements signature of a specific constituent, is not well-defined (or not "single-valued"), but rather changes with time or DOI, even as the x-constituent substitution occurs in pairs. This is, for example, the case with NMR measurements, whereby the signature of the "wetting" fluid will generally depend on the "saturation" (fractional volume of the pore space occupied by the particular fluid) of that particular fluid constituent. For example, when one such fluid fills the pores of a well-sorted sandstone formation, the NMR log measurements—T2 distributions for example—will respond in one manner (i.e. a single peak response, located in the "free-fluid" part of the T2 distribution). However, should another "non-wetting" and "non-miscible" fluid be present in or invade the pore spaces, displacing and leaving behind a thin film residue of the original wetting fluid that coats and lines the surface of the sandstone grains, then the NMR log measurements will respond differently to the residual fluid (i.e. a single peak response may be present, located at the edge of the "bound-fluid" part of the T2 distribution). The reverse is also true.

This NMR "exception" can be viewed and processed in at least two ways. It may be viewed as an x-constituent substitution in which the substitution occurs in triplets, whereby the wetting fluid originally filling the pores of the formation is replaced by the intrusive non-wetting, non-miscible fluid, plus the residual wetting fluid, treated as a separate constituent. In this case, the three constituents have a well-defined single-peak NMR log response that substantially does not change. The NMR exception may also be considered as an x-constituent substitution in which the substitution occurs in pairs, whereby the wetting fluid originally filling the pores of the formation is hypothetically subdivided into free and bound fluids, such that the free fluid is replaced by the intrusive non-wetting, non-miscible fluid, and the bound fluid remains in place. In this case, however, the bound fluid constituent cannot be assigned a well-defined single-peak NMR log response. However, when one of the NMR snapshots, includes the bound fluid constituent alone, excluding any free wetting fluid, the observed x-constituent substitution pattern may become well-defined, despite the change in wetting fluid signature in between the separate snapshots, as will be demonstrated further down in the present description.

Another possible reason the NMR log response of a specific fluid constituent may change between the different well log measurements is the onset of "restricted diffusion", when the saturation of such specific fluid drops below a certain threshold. The reverse is also true. Whether or not diffusion effects result in special processing procedures may depend on the specifications of the NMR logging instrument and the measurement type considered. Diffusion effects are may be a factor when gas is one of the constituents present in the formation, however the NMR log response of gas happens also to be relatively small in amplitude as compared to that of liquids, due to a combination of low hydrogen index (HI) and low polarization factor (Pol), which may mask the diffusion effects foreseen in gas-bearing formations.

Yet another reason the NMR log response of a particular constituent may change between the different snapshots, is related to the data acquisition and the data processing itself. Those operations may translate into differences in the NMR log response of many of the constituents from one NMR snapshot to the next, even as no changes in the constituents may have actually occurred. Those differences would generally manifest themselves as residual, low-amplitude, coherent "ripples" or "waves" (peaks and troughs) when NMR T2 distributions for example from the different NMR snapshots taken are subtracted from each other. The changes from one snapshot to the next, will generally be directed to the broadening or contraction of the corresponding "mode(s) width(s)" on NMR distributions, producing either relatively small or controlled-behavior shifts in the location of the "mode(s) peak(s)" on a case-by-case basis. There is an expected correlation between such "sibling modes" from different snapshots, and therefore one may circumvent the effect of changes resulting from log data acquisition and processing. The approach depends on whether one views the data in NMR relaxation time distribution space or NMR spin echo amplitude space, each of which presents its own advantages. Observing NMR data in spin echo amplitude space allows one to investigate the effects associated with data processing parameters in general, or different "regularization" parameters in particular. Observing the NMR data in relaxation time distribution space assists in controlled-behavior (if not fully predictable) modeling.

Changes in data acquisition parameters, types of well logging instruments, and environmental conditions should be avoided as much as possible, or otherwise accounted for. If changes are unavoidable, one should acquire a new "base log" as soon as practicable, whereby the idea is to measure the formation twice with substantially no or minimal changes in the formation constituents expected therebetween, under two different sets of conditions, to record changes in well log instrument responses due to changes in conditions alone. Again, observing the NMR data in relaxation time or diffusion constant distribution space, and statistical analysis techniques in general or factor analysis or PCA in particular, may also be used to assist in "sibling mode" identification and/or controlled-behavior (if not fully predictable) modeling.

Figure 1A:
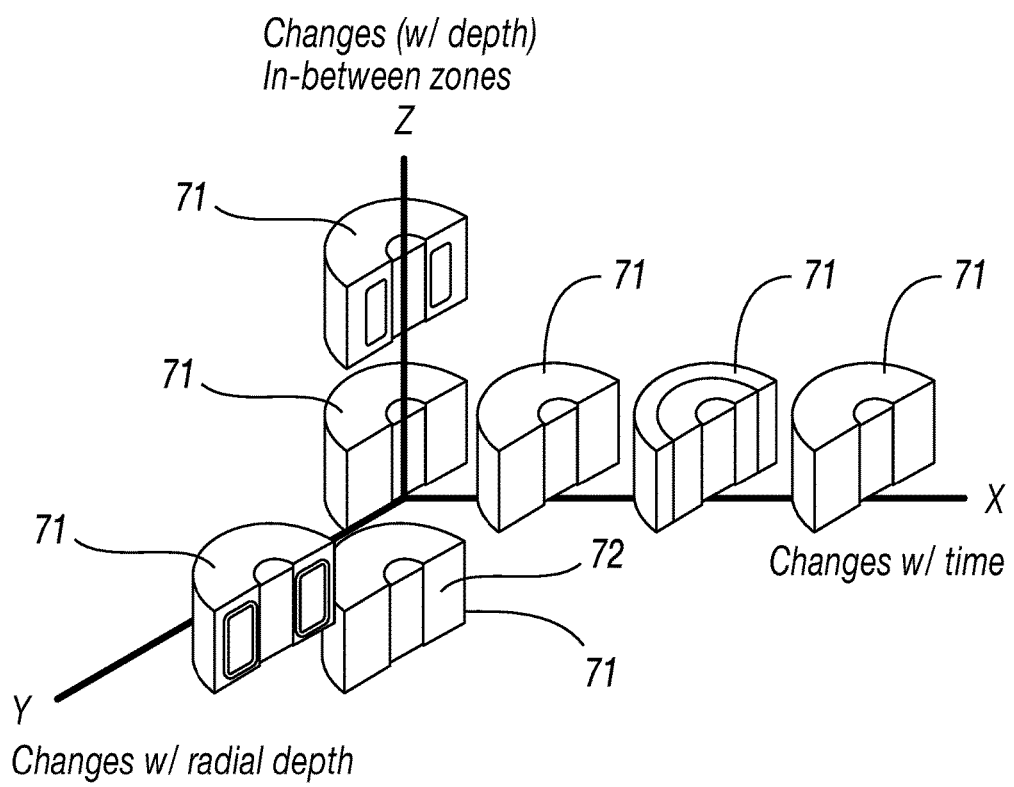
FIG. 1A is a diagram of possible origins and causes of observed changes in between different "snapshots" (e.g. at different times or at different depths-of-investigation's or at different depths), in accordance with this disclosure.

The method and system disclosed herein apply to a wide range of situations, depending on the many possible origins of the observed changes in the formation composition between the different snapshots. Indeed, the observed changes may be the result of displaced fluids, displaced formation fine-grained solid particles, mud fines invasion, pore fluid phase changes (such as those initiated by pressure or temperature changes), chemical reactions, dissolution or precipitation (e.g. asphaltene precipitation, scale deposition, salt dissolution, acid stimulation) of solid components, or changes in compaction or pressure or stress regimes, and the time scale for the observed changes may vary depending on the situation considered. Possible origins and causes of observed changes in between different snapshots are indicated in FIG. 1A. The system and method may address changes with time (i.e. when the same volume of formation is measured at different times, where the first time may be referred to as a "base log") shown on the "X axis", changes with radial depth (i.e. when deeper-and-deeper volumes of the same formation are measured at just one time, which may exploit different sets of consonant measurements for each of the deeper-and-deeper volumes measured) shown on the "Y axis", and changes with wellbore depth (when one "same" constituent is present and takes part in the foreseen x-constituent pair substitutions) as shown on the "Z axis". The semi-cylindrical regions 71 in FIG. 1A represent a section of underground formation surrounding the wellbore, in which the composition of the formation may be different across a single radial axisymmetric boundary with-respect-to the wellbore, and wherein a measurement volume or zone of investigation within the formation is indicated by a rectangle 72. This may result for example when a wellbore fluid (e.g. drilling mud filtrate) penetrates the formation and displaces native formation fluids to different extents depending on various wellbore fluid and formation characteristics and parameters such as composition, viscosity, pressure, porosity, saturation, and permeability. The composition of the formation may undergo a step change at such radial axisymmetric boundary, or the change may be gradual. The composition of the formation may also change across multiple radial axisymmetric boundaries (not just a single one) with-respect-to the wellbore, depending on changes in the wellbore fluid, or depending on various fluids relative permeability effects, or depending on the origin of the observed changes (e.g. chemical reactions). Other combinations of scenarios such as changes with time and changes with radial depth may also be included. In addition, the disciplines of production logging and drilling optimization, as compared to formation evaluation, concern themselves, respectively, with the contents of the wellbore during production or injection, and with the contents of the wellbore during drilling, in contradistinction to the constituents of the formation. The system and method described herein may apply to the field of production logging and/or drilling optimization (e.g. hole cleaning and "kick" detection).

Changes with time may be induced, for example, by injection, production, or thermo-mechanical "setting". Injection-induced changes may occur over a small time scale or a large time scale. Examples of small time scale injection-induced changes include invasion dynamics (e.g. "drill" pass vs. "wipe" or repeat pass log data acquisition, in case of conventional overbalance drilling), reservoir stimulation techniques or solvent injection (such as coupled invasion with chemical reaction dynamics), and "log-inject-log" techniques (i.e. multiple invasion cycles with fit-for-purpose invading fluids). An example of a large time scale change is the reservoir monitoring of injector wells. Similarly, production-induced changes may occur over a small time scale or a large time scale. Examples of small time scale production-induced changes include underbalance drilling and pressure-induced changes (such as gas expansion, "condensate banking", gas coming-out of solution, gas coning, water coning, and "thief zones"). An example of a large time scale change is the reservoir monitoring of producer wells. Thermo-mechanical "setting" induced changes include small time-scale temperature-induced changes (such as thawing and melting of ice or hydrates) and large time-scale temperature-induced changes (such as changes in heavy oil properties using thermal recovery techniques). Thermo-mechanical "setting" induced changes may also include large time-scale stress-induced changes.

Similar examples may be cited for changes with radial depth. The case of changes in wellbore depth is somewhat counter-intuitive, and is generally applicable when a specific "exact same" constituent is in fact present at many different wellbore depths, and the other constituents are present "one at a time" at different wellbore depths (i.e. excluding the situations where two or more other constituents are present simultaneously). In this case, the measurements made at any one depth may be simply benchmarked against a hypothetical situation in which that one same constituent occupies the entire volume of formation alone. Even when the particular nature of that same constituent is just known approximately, the fact the measurements are made in the presence of the same constituent is sufficient to use the present method. In practice, in case the exact same constituent present at different depths along the wellbore is a rock mineral, then such same rock mineral composition may be asserted or differentiated, based on well log data that responds primarily to the rock minerals alone. Examples of such log data includes, but is not limited to, elemental thermal neutron capture spectroscopy and natural gamma-ray spectroscopy data. The rock mineral composition may also be differentiated based on surface observations such as, but not limited to, core data and mud logging data (particularly the analysis of drill cuttings). In practice also, in case the same constituent present at different depths along the wellbore is a fluid, then such same fluid type may also be differentiated based on well log measurement data that responds primarily to the fluids, such as formation fluid testing instrument data. The fluid type may also be differentiated, for example, based on surface observations from an analysis of produced fluids or mud logging data and the analysis of mud returns. This fluid type may also be ascertained simply because it is being injected from surface, such as drilling mud filtrate in the case of conventional overbalance drilling.

If the same rock mineral composition (i.e. rock "mineralogy") can be positively asserted, changes in log measurements may be used to identify and distinguish different fluids from each other. Moreover, changes in fluid type, including notable variations in porosity (fractional volume of pore space in a formation), may also be used to assign a unique signature for the above-mentioned rock mineral composition with-respect-to the different log measurements considered. If, on the other hand, the same fluid type can be positively asserted, changes in log measurements may be used to identify and distinguish different rock mineral compositions from each other. Moreover, changes in rock mineralogy, including notable variations in porosity, may also be used to assign a unique signature for the above-mentioned fluid type with-respect-to the different log measurements considered.

To identify and classify the changes that have taken place, in the present example the vector notation $\vec{M}$ may be introduced, which coordinates correspond to the different consonant log measurements considered $m_1 \, m_2 \, \ldots \, m_\alpha \, m_\beta \, \ldots \, m_n$ (from "1" to "n"), and snapshots may be referred to using similar vector notation as $\vec{M}^1 \, \vec{M}^2 \ldots \vec{M}^I \, \vec{M}^n$ (from "1" to "N"), whereas the different formation constituents' unique signatures with-respect-to the different log measurements considered may be referred to using similar vector notation as $\vec{M}_A \, \vec{M}_B \ldots \vec{M}_I \, \vec{M}_J \ldots \vec{M}_Z$ (from "A" to "Z"). Furthermore, $\vec{M}$ may represent $\vec{M}$ itself, or any linear transformation thereof. Where the volume and log measurements signatures of some constituents are known a priori, the notation $\vec{M}$ may also include such transformations that remove from $\vec{M}$ these known constituents' contributions, to produce a less complex $\vec{M}$ vector that depends on the remaining unknown constituents.

The foregoing vectors may also be displayed as curves over "n" data points, taking on the series of values $m_1 \, m_2 \ldots m_\alpha \, m_\beta \ldots m_n$, in which case the vector notation may be dropped and substituted with the respective curve notations $\tilde{M}$, and $\tilde{M}^1 \, \tilde{M}^2 \, \ldots \, \tilde{M}^I \, \tilde{M}^J \, \ldots \, \tilde{M}^N$, and $\tilde{M}_A \, \tilde{M}_B \ldots \tilde{M}_I \, \tilde{M}_J \ldots \tilde{M}_Z$. The foregoing represents an example of how NMR multi-component data may be displayed, and the term "distribution(s)" has been used herein with reference to the associated (corresponding) curves. In the present description, the consonant log measurements considered $m_1 \, m_2 \ldots m_\alpha \, m_\beta \ldots m_n$, may also be unit-less or dimensionless by "normalizing" the measurements to the quantum of noise inherently present in each type of measurement. This is helpful to remain above the noise level intrinsic to various measurements and to avoid confusing noise with true information. This is also useful when displaying the above-discussed vectors or functions on a "neutral" or "user-independent" scale. Note that aforementioned measurement normalization is different from other normalizations introduced later in the present description, such as signature "pseudo-normalization" and signature "true normalization" (including two separate sorts of "true" normalization, using an "apparent" or a "true" drilling mud-filtrate volume in accordance with an example embodiment).

FIG. 2A shows conventional overlays, displaying the individual log responses of each constituent (the "vector" signatures $\vec{M}_A \, \vec{M}_B \ldots \vec{M}_I \, \vec{M}_J \ldots \vec{M}_Z$), and although FIG. 2A is displayed in a two-dimensional plane (i.e. the surface of the page on which it is printed), it is intended as an overlay in an n-dimensional space, to accommodate the "n" log measurements considered $m_1\ m_2\ \ldots\ m_\alpha m_\beta\ \ldots\ m_n$. These overlays are used to cross-plot data points $\vec{M}^1\ \vec{M}^2\ \ldots\ \vec{M}^i\ \vec{M}^j\ \ldots\ \vec{M}^N$ corresponding to each of the snapshots, and which are in fact a linear mixture of the various constituents endpoints $\vec{M}_A\ \vec{M}_B\ \ldots\ \vec{M}_I\ \vec{M}_J\ \ldots\ \vec{M}_Z$ weighed by the percentage volume of the respective constituent as present in the volume investigated by the respective snapshot. The (grey) lines joining different vectors correspond to the direction parallel to the corresponding x-constituent pair exchange (x-constituent substitution), e.g. the lines terminating in A, B, I, J and Z. This is further detailed in FIG. 2B.

Assuming measurements with linear mixing laws, changes in $\vec{M}$ can then be expressed as a linear combination of vectors $(\vec{M}_J-\vec{M}_I)$ as follows:

$$\begin{cases} \vec{M}^j = \sum_I V_I^j \cdot \vec{M}_I \\ \vec{M}^i = \sum_I V_I^i \cdot \vec{M}_I \end{cases}$$

$$\Delta_{ij}(\vec{M}) = \vec{M}^j - \vec{M}^i$$
$$= \sum_I \Delta_{ij}(V_I) \cdot \vec{M}_I$$
$$= \sum_{All\{I,J\}pairs} \left\{ \frac{(V_J^j - V_J^i) - (V_I^j - V_I^i)}{Z} \right\} \cdot (\vec{M}_J - \vec{M}_I)$$

with foreknowledge that the above expression is not unique, as the vectors $(\vec{M}_J-\vec{M}_I)$ are interdependent. The introduced notation "$\Delta_{ij}(\vec{M})$" for example, refers to the difference in log measurements "$\vec{M}$" between the corresponding snapshots no. "j" and no. "i" (i.e. the difference between "$\vec{M}^j$" and "$\vec{M}^i$"), the introduced notation $V_J^j$ for example, refers to the percentage volume of constituent "J", present in the volume of formation investigated by the corresponding snapshot no. "j", and the introduced notation $\Delta_{ij}(V_I)$ for example, refers to the difference in percentage volume of constituent "I", present respectively in the volume of formation investigated by the corresponding snapshots no. "j" and no. "i".

In the case of a constituent "I" and "J" single pair exchange, the expression below follows:

$$\Delta_{ij}(\vec{M})=\Delta_{ij}(V_J)\cdot(\vec{M}_J-\vec{M}_I)=\Delta_{ij}(V_I)\cdot(\vec{M}_I-\vec{M}_J).$$

Figure 2B:
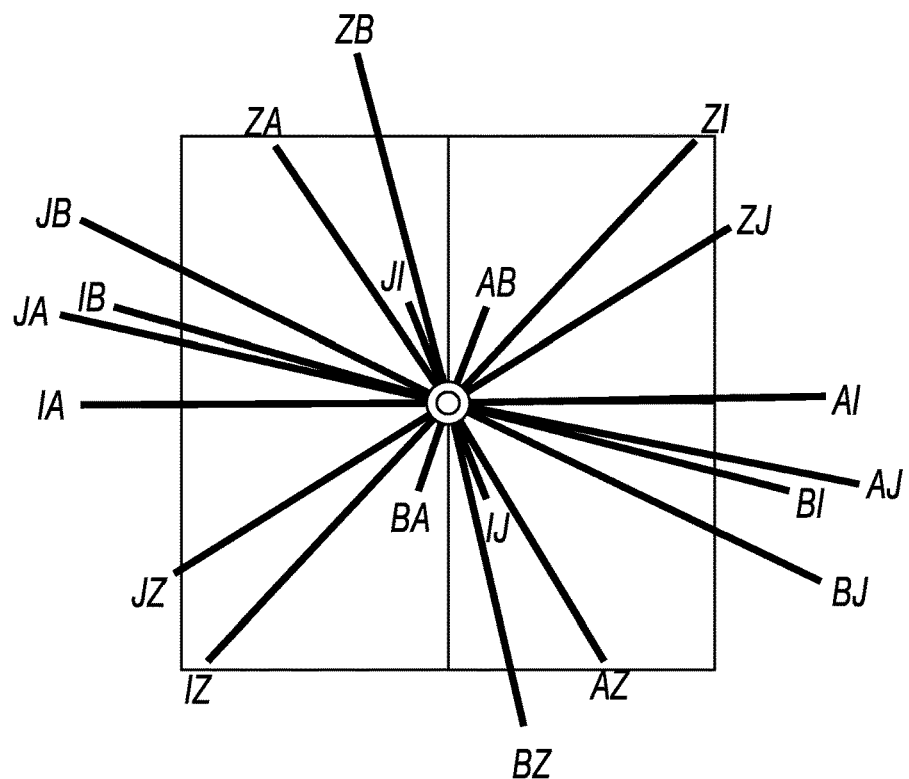
FIG. 2B is a plot of a modified overlay including vectors (or straight line segments) passing through the origin "O" produced by replicating (or "sliding") the various vectors $(\vec{M}_J - \vec{M}_I)$ from FIG. 2A.

To gain an initial insight into the x-constituent exchanges taking place, the resulting measurement difference such as "$\Delta_{ij}(\vec{M})$" may be cross-plotted against the modified overlay in FIG. 2B, which is also intended as an overlay in n-dimensional space. The modified overlay, including vectors (or straight line segment) labeled AB, BA, . . . , JZ, ZJ, . . . starting at the origin "O", may be produced by replicating (or "sliding") the various vectors $(\vec{M}_J-\vec{M}_I)$ from FIG. 2A onto the present cross-plot of FIG. 2B, and having them start at point "O". That is, the same line segments from FIG. 2A are displayed, but the line segments have been translated to start at the same point, i.e. the center of the cross-plot. The labeling and coding of the various line segments reflect the corresponding start and end points from corresponding FIG. 2A. Data point patterns resulting from x-constituent pair exchanges lay directly on each corresponding line segment.

Figure 2C:
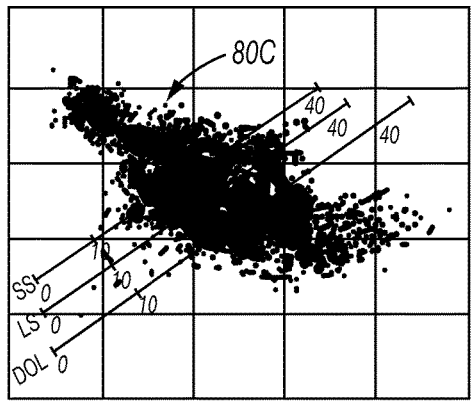
FIGS. 2C through 2F are graphs illustrating how the overlays apply, with patterns and "clusters" of data points aligning approximately along different line segments, indicating different x-constituent pair exchanges.
Figure 2D:
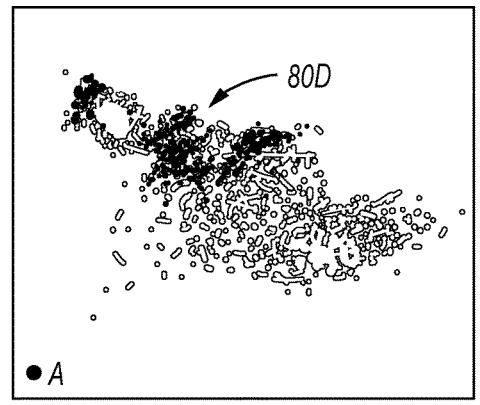
Figure 2E:
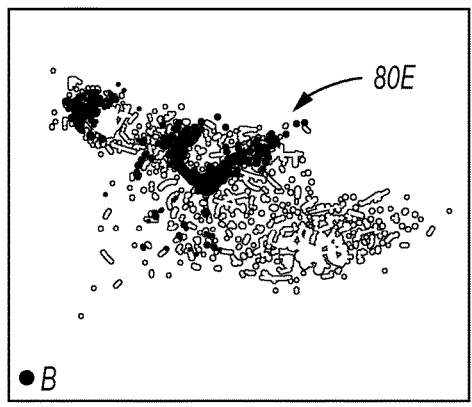
Figure 2F:
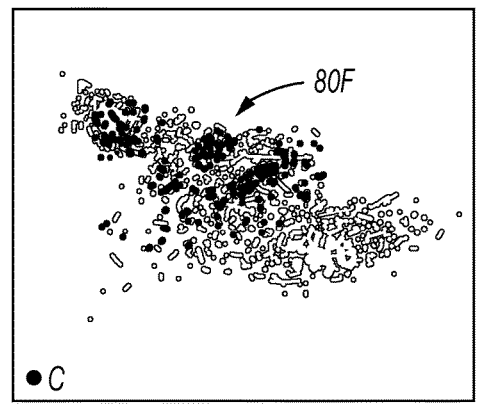

FIGS. 2C through 2F illustrate how the overlays apply, with patterns and respective "clusters" 80c-80f of data points aligning substantially along different line segments, indicating different x-constituent pair exchanges. FIGS. 2C through 2F illustrate how the technique described herein applies for changes (with depth) in between zones, where one same constituent is present and takes part in the foreseen x-constituent pair substitutions. They show that where the rock mineralogy can be positively discriminated, order emerges from a "cloud" of data points from individual well log measurements with no apparent structure. FIG. 2C shows example data points representing logging instruments measurement results, displayed on a conventional overlay where the "X axis" and "Y axis" correspond respectively to neutron porosity and bulk-density measurements in this case. The lines displayed, join reference constituents which may be encountered in underground formations (corresponding to such x-constituent substitution lines), but such reference constituents may not be actually present in the underground formation. The reference constituents concerned were sandstone (labeled SS), limestone (labeled LS), dolomite (labeled DOL), and water which would plot outside the boundaries of the plot shown (the water point would be located further up to the right of the plot shown), and hence the three lines shown would join at the water point. The fact that the example datapoints displayed do not fall on the reference lines, just means that we are in the presence of actual formation constituents different from the reference ones displayed. FIGS. 2D through 2F show the same data points from FIG. 2C, but highlighting separately those datapoints corresponding to different rock mineralogy "A", "B", and "C", where rock mineralogy may be positively discriminated. The data points are displayed, along with the hypothetical response of the rock formation by itself.

Figure 2G:
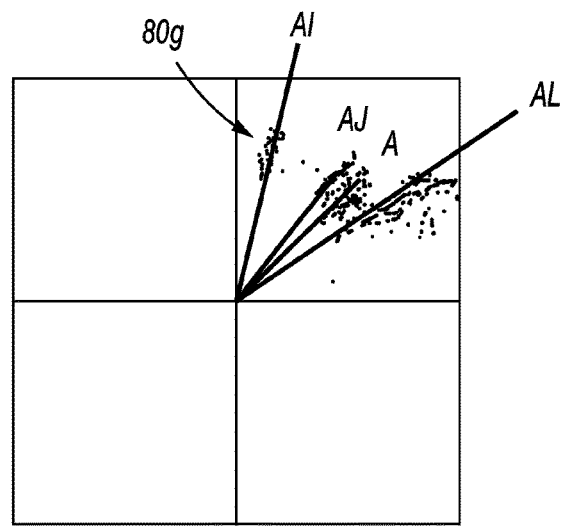
FIGS. 2G through 2I are graphs which follow from FIGS. 2C through 2F and illustrate how the overlays apply with patterns and "clusters" of datapoints aligning approximately along different line segments passing through the origin "O", indicating different x-constituent pair exchanges.
Figure 2H:
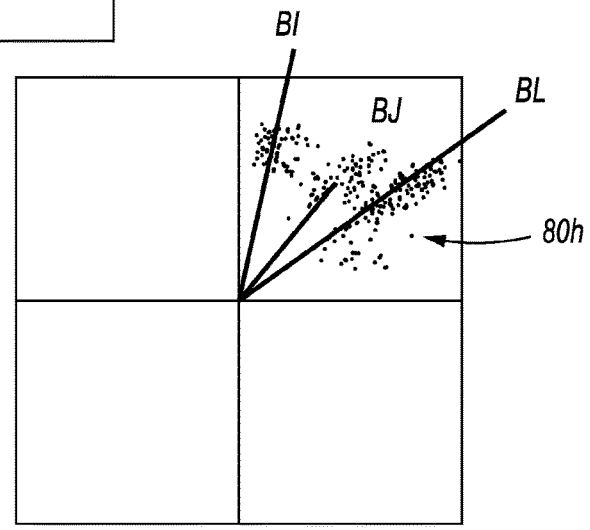
Figure 2I:
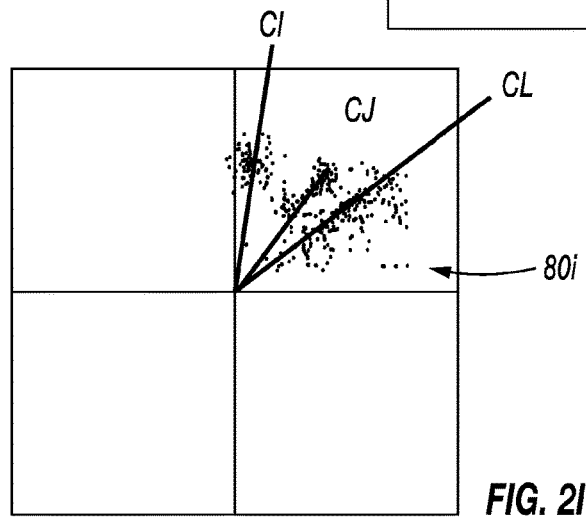

FIGS. 2G through 2I follow from FIGS. 2C through 2F and illustrate how the modified overlays apply with patterns and "clusters" of data points 80g-80i aligning reasonably well along different line segments indicating different x-constituent pair exchanges. These three figures show separately the line segments corresponding to the patterns resulting from x-constituent pair exchanges involving respectively the three rock mineralogy "A", "B", and "C". It may be observed in FIG. 2G, that rock mineralogy "A" represents one of the constituents, and there are four different fluid types identified. Similarly FIG. 2H shows the line segments corresponding to the patterns resulting from x-constituent pair exchanges in which rock mineralogy "B" is one of the participating constituents, and there are three different fluid types identified. Similarly FIG. 2I shows the line segments corresponding to the patterns resulting from x-constituent pair exchanges in which rock mineralogy "C" is one of the participating constituents, and again three different fluid types are identified.

Figure 2J:
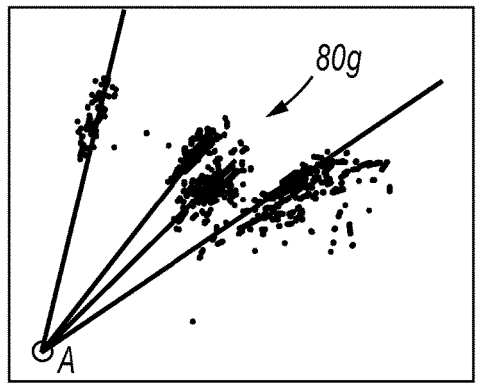
FIGS. 2J through 2M are graphs integrating information from FIGS. 2C through 2F and FIGS. 2G through 2I, displaying the x-constituent pair exchange patterns on the original conventional overlays.
Figure 2K:
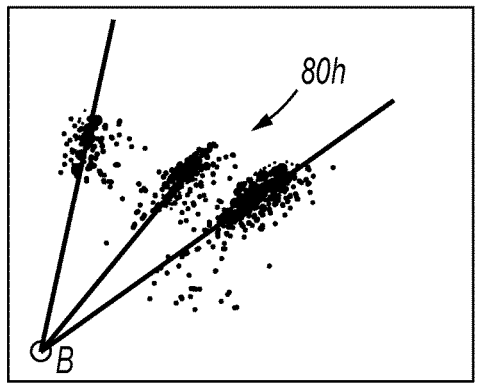
Figure 2L:
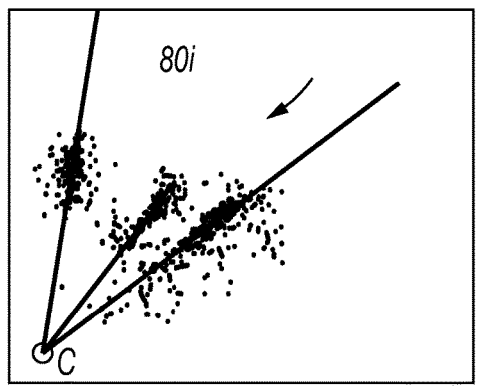
Figure 2M:
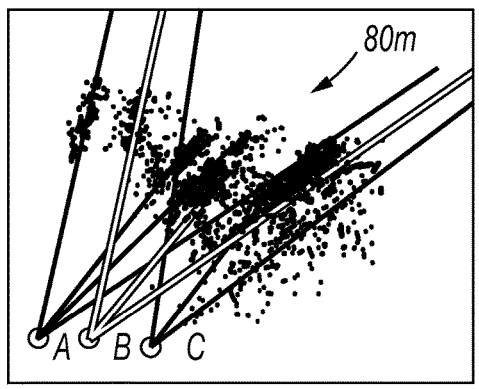
Figure 2N:
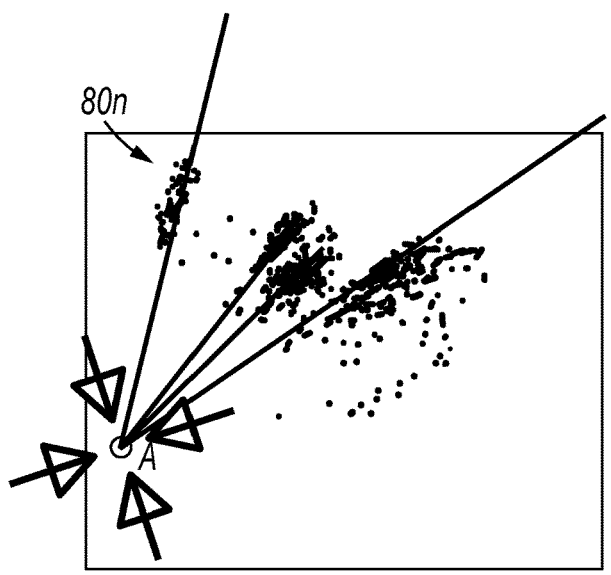
FIGS. 2N and 2P are graphs using the same example as FIGS. 2C through 2M, which illustrate how observable variation in porosity can be used to assign a unique log measurements response or "signature" to an "exact same" constituent participating simultaneously in the different x-constituent pair exchanges.
Figure 2P:
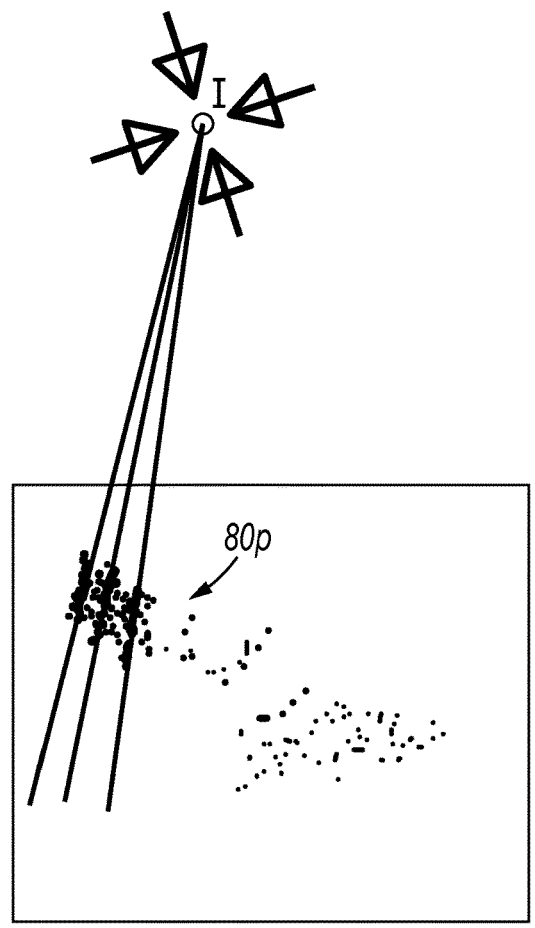

FIGS. 2J through 2M integrate information from FIGS. 2C through 2F and FIGS. 2G through 2I, displaying the x-constituent pair exchange patterns on the original conventional overlays. FIGS. 2J through 2L are similar to FIGS. 2G through 2I, using respectively conventional and modified overlays. They suggest how the line segments may converge towards a common point, as shown in FIG. 2M with a combined point cloud 80m, revealing more ordered patterns. FIGS. 2N and 2P illustratively includes point clouds 80n and 80p and follow the same example as FIGS. 2C through 2M and illustrate how notable variations in porosity can be used to calibrate the in-situ log measurements signature of a same constituent participating simultaneously in the different x-constituent pair exchanges foreseen.

As shown in FIG. 2N, where rock mineralogy can be positively discriminated, but the corresponding in-situ log measurements signature is not necessarily available to a substantial degree of confidence, and where changes in fluid type are also accompanied with notable variations in porosity, then different line segments "fitted" to the different segregated clusters of data points corresponding to different x-constituent pair exchanges, may be extrapolated to join at a single point indicating the log measurements signature of the corresponding mineralogy. Conversely, as shown in FIG. 2P, where fluid composition can be positively discriminated, but the corresponding in-situ log measurements signature is not necessarily available to a substantial degree of confidence, and where changes in rock mineralogy are also accompanied with notable variations in porosity, then different line segments "fitted" to the different segregated clusters of data points corresponding to different x-constituent pair exchanges, may be extrapolated to join at a single point indicating the log measurements signature of the corresponding fluid type.

Situations may also arise in which a same constituent taking part in the foreseen x-constituent pair substitutions may be established with a substantial degree of confidence, without necessarily having detailed knowledge of its unique signature with-respect-to the different log measurements considered. The method described herein may be used for those cases as well. From a mathematical standpoint, this involves the introduction of new techniques to simultaneously fit multiple segregated clusters of data points, with convergent two- or more lines joined at a common point in two- or more dimensional space. When working with NMR data, we may extend such terminology and speak of "convergent distributions (or other forms of multi-component NMR data)" joined at a "common distribution", based on the understanding that such NMR data may also be regarded as vectors or data points in multi-dimensional space.

Because data points from the resulting measurement differences such as "$\Delta_{ij}(\vec{M})$" (the difference in log measurements "$\vec{M}$" between the snapshots no. "j" and no. "i" i.e. between "$\vec{M}^j$" and "$\vec{M}^i$") are foreseen to assemble in clusters along the vectors from FIG. 2B (which identify which pair of formation constituents "I" and "J" have substituted each other between the time-lapse or MDOI snapshots no. "j" and no. "i" considered), it may be desirable to effectively distinguish these clusters from one another in practice, by proceeding to compute data point histograms per solid angle in n-dimension space, or by way of normalizing the data point vectors $\Delta_{ij}(\vec{M})$ to be of unit length (i.e. to project them against an n-dimensional unit sphere) according to the expression:

$$\frac{\Delta_{ij}(\vec{M})}{\|\Delta_{ij}(\vec{M})\|}.$$

Such normalization which may be referred to as "pseudo-normalization" in the following, may be limited to those data point vectors $\Delta_{ij}(\vec{M})$ above a predetermined noise threshold $\|\Delta_{ij}(\vec{M})\|\gg\eta$, and the norm $\|\Delta_{ij}(\vec{M})\|$ may be defined in a number of ways. That is, alternative pseudo-normalization or other projection techniques are also possible. A pseudo-normalization may expressly show some of the x-constituent substitution patterns present, where the substitution has resulted in noticeable differences $\Delta_{ij}(\vec{M})$ between the snapshots no. "j" and no. "i". Other statistical techniques, such as factor analysis or PCA for example, may also be used (factor analysis or PCA is particularly suited to NMR data, as discussed in U.S. patent application Ser. No. 13/658,502 entitled "Identifying Formation, Matrix and Fluid Related Characteristics from Subsurface Data Using Factor Analysis", by Jain et al., which was filed on Oct. 23, 2012 and is assigned to the present Assignee and is hereby incorporated herein in its entirety by reference). Factor analysis or PCA may be applied to identify the dimensionality of the corresponding vector space resulting from the measurements differences such as "$\Delta_{ij}(\vec{M})$" (i.e. the number of "principal factors" and "principal components" that may account for the vast majority of the dataset). This dimensionality may correspond to the number of constituents that have substituted each other between the snapshots no. "i" and no. "j" considered, minus one. It should be noted that the dimensionality may also be enforced by outside observations available beforehand, such as mud logging data, or educated assumptions, for example. "Oblique rotation" techniques may then be applied, to generate the various x-constituent substitution patterns present. Moreover, artificial Neural Network (NN) techniques may be used to automatically segregate the formation into zones, according to the patterns trained into the artificial NN. The above-mentioned statistical techniques may be applied to the entire depth interval considered, or zone-by-zone, or in a sliding depth interval fashion.

Figure 2Q:
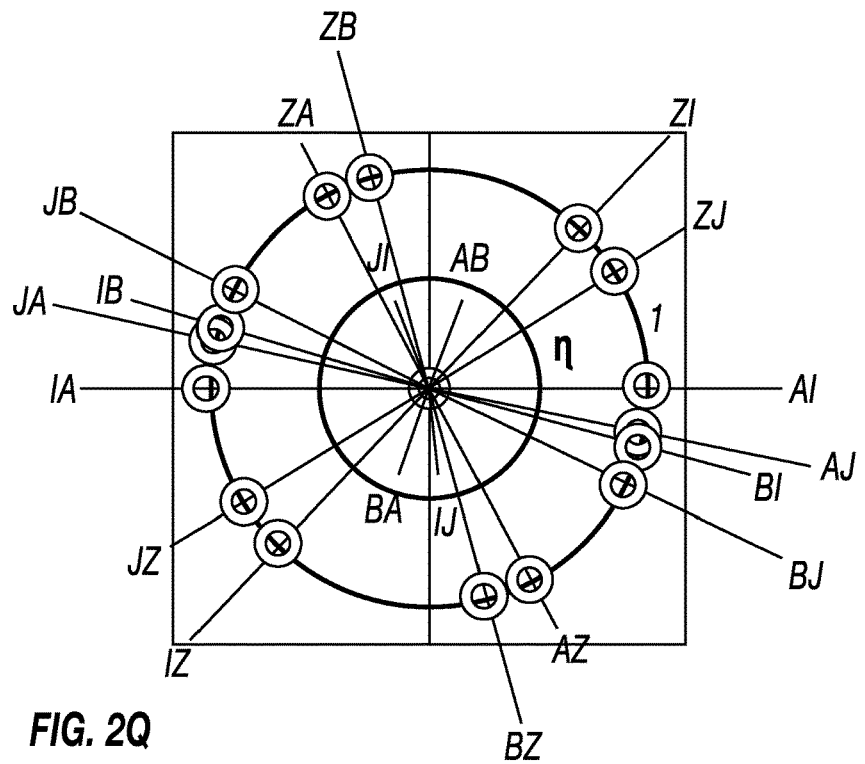
FIG. 2Q is a plot illustrating a pseudo-normalization, in which the "norm" is taken to be $\|\vec{u}\| = \sqrt{\Sigma_i u_i^2}$, and where those datapoints with norm above a preset noise threshold $\|\Delta_{ij}(\vec{M})\| \gg \eta$ are displayed.
Figure 2R:
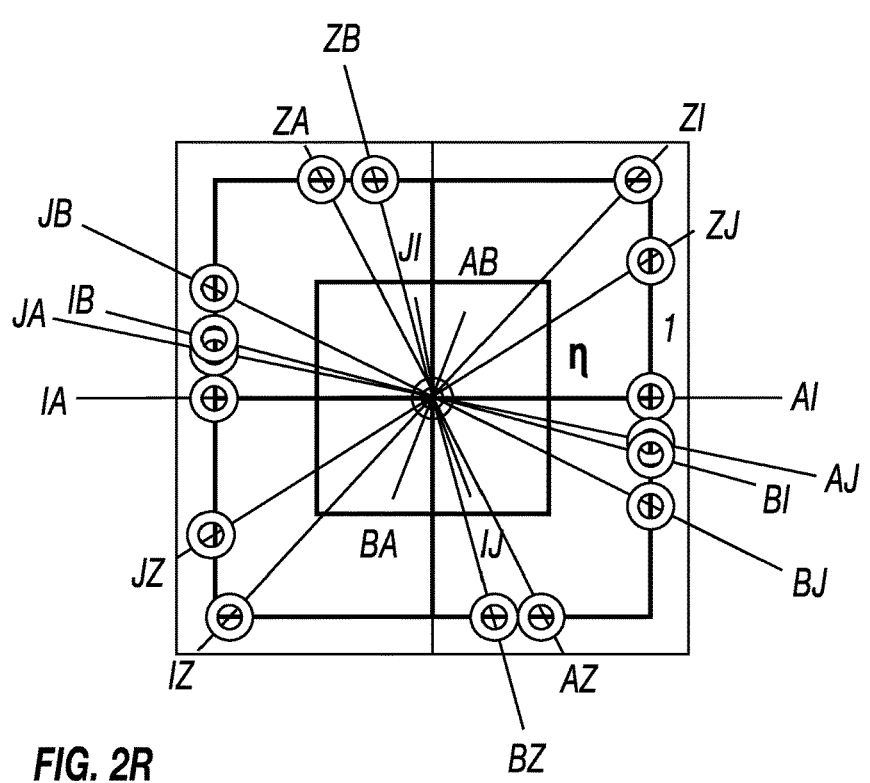
FIG. 2R is a plot illustrating a pseudo-normalization in which the norm is taken to be $\|\vec{u}\| = \max_i (|u_i|)$, and where those datapoints with norm above a preset noise threshold $\|\Delta_{ij}(\vec{M})\| \gg \eta$ are displayed.

FIG. 2Q illustrates how a pseudo-normalization works, in which the norm is taken to be $\|\vec{u}\|=\sqrt{\Sigma_i u_i^2}$, and where those data points with norm above a preset noise threshold $\|\Delta_{ij}(\vec{M})\|\gg\eta$, are displayed. Such a pseudo-normalization allows data points corresponding to the same x-constituent pair substitution to project onto one and the same point of a unit circle (or unit sphere). FIG. 2Q is intended in n-dimensional space, to accommodate the "n" log measurements considered. FIG. 2R illustrates a pseudo-normalization in which the norm is taken to be $\|\vec{u}\|=\max_{i=1\ldots n}(|u_i|)$, and where those data points with norm above a predetermined noise threshold $\|\Delta_{ij}(\vec{M})\|\gg\eta$ are displayed. FIG. 2R is also intended in n-dimensional space.

The NMR exception described earlier may result in the above equations being modified as follows:

$$\begin{cases} \tilde{M}^j = \sum_I v_I^j \cdot \tilde{M}_I^j \\ \tilde{M}^i = \sum_I v_I^i \cdot \tilde{M}_I^j \end{cases}$$

-continued $$\Delta_{ij}(M) = \tilde{M}^j - \tilde{M}^i$$

$$= \sum_{J \in \{non\text{-}wetting\ fluids\}} \Delta_{ij}(V_{J,nwf}) \cdot \tilde{M}_{J,nwf} +$$

$$\sum_{I \in \{wetting\ fluids\}} \left(V_{I,wf}^j \cdot \tilde{M}_I^j - V_{I,wf}^i \cdot \tilde{M}_I^i\right)$$

$$= \sum_{J \in \{non\text{-}wetting\ fluids\}} \Delta_{ij}(V_{J,nwf}) \cdot \tilde{M}_{J,nwf} +$$

$$\sum_{I \in \{bound\ wetting\ fluids\}} V_{I,bwf}^j \cdot \left(\tilde{M}_{I,wf}^j - \tilde{M}_{I,wf}^i\right) +$$

$$\sum_{I \in \{free\ wetting\ fluids\}} \Delta_{ij}(V_{I,fwf}) \cdot \left(\tilde{M}_{I,wf}^j - \tilde{M}_{I,wf}^i\right)$$

(in which "nwf" represents the non-wetting fluid and "wf" represents the wetting fluid) which in the case of one non-wetting fluid, and assuming the second time-lapse or MDOI "snapshot" includes the bound fluid constituent alone, with the exclusion of any free wetting fluid, further reduces to:

$$\Delta_{ij}(\tilde{M}) = \Delta_{ij}(V_{J,nwf}) \cdot (\tilde{M}_{J,nwf} - \tilde{M}_{I,wf}^i) + V_{I,bwf}^j (\tilde{M}_{I,wf}^j - \tilde{M}_{I,wf}^i)$$

(in which "bwf" represents the bound wetting fluid) or yet again as:

$$\Delta_{ij}(\tilde{M}) =$$

$$\Delta_{ij}(V_{J,nwf}) \cdot \left(\tilde{M}_{J,nwf} - \left\{\left(1 + \frac{V_{I,bwf}}{\Delta_{ij}(V_{J,nwf})}\right) \cdot \tilde{M}_{I,wf}^i - \left(\frac{V_{I,bwf}}{\Delta_{ij}(V_{J,nwf})}\right) \cdot \tilde{M}_{I,wf}^j\right\}\right)$$

Also, the term $$\frac{V_{I,bwf}}{\Delta_{ij}(V_{J,nwf})}$$

shown above, is generally related to $\tilde{M}_{I,wf}^i$ itself, according to the expression:

$$\frac{V_{I,bwf}}{\Delta_{ij}(V_{J,nwf})} \approx a \cdot \left(\frac{T_{2lm}(\tilde{M}_{I,wf}^j)}{T_{2lm}(\tilde{M}_{I,wf}^i)}\right)^2 \approx a \cdot \left(\frac{T_{2lm}(\tilde{M}_{I,wf}^j)}{T_{2bm}(\tilde{M}_{I,wf}^i)}\right)^2$$

(in which the subscript "lm" represents the "logarithmic mean") where "a" may be considered a relatively constant parameter (e.g. around 4.5), and the formulas are valid up to the respective bulk relaxation times of the considered wetting fluid. The formula when using $T_1$ log mean, presents the advantage of being immune to diffusion effects. The foregoing formulas were derived by equating $K_{SDR} \approx K_{TC}$ (respectively known in the industry, as the "SDR" NMR permeability transform, and the "Timur-Coates" permeability transform). Other closely related expressions for the term $$\frac{V_{I,bwf}}{\Delta_{ij}(V_{J,nwf})}$$

may also be used, as may be derived based on the physics of the NMR measurement.

The expressions above serve to demonstrate that the wetting fluid actually behaves like a constituent with an "effective" well-defined NMR log measurement signature, as follows:

$$\left\{\left(1 + \frac{V_{I,bwf}}{\Delta_{ij}(V_{J,nwf})}\right) \cdot \tilde{M}_{I,wf}^i - \left(\frac{V_{I,bwf}}{\Delta_{ij}(V_{J,nwf})}\right) \cdot \tilde{M}_{I,wf}^j\right\} =$$

$$\left\{\left(1 + a \cdot \left(\frac{T_{2lm}(\tilde{M}_{I,wf}^j)}{T_{2lm}(\tilde{M}_{I,wf}^i)}\right)^2\right) \cdot \tilde{M}_{I,wf}^i - a \cdot \left(\frac{T_{2lm}(\tilde{M}_{I,wf}^j)}{T_{2lm}(\tilde{M}_{I,wf}^i)}\right)^2 \cdot \tilde{M}_{I,wf}^j\right\}$$

which includes a counter-intuitive "two-peak" NMR log measurement response instead of just one "peak", and where one of the peaks is positive and the other peak is negative instead of solely positive peaks. Data point clustering techniques, pseudo-normalization techniques, or other statistical and classification techniques suggested earlier may then apply here also to NMR measurements.

Figure 3A:
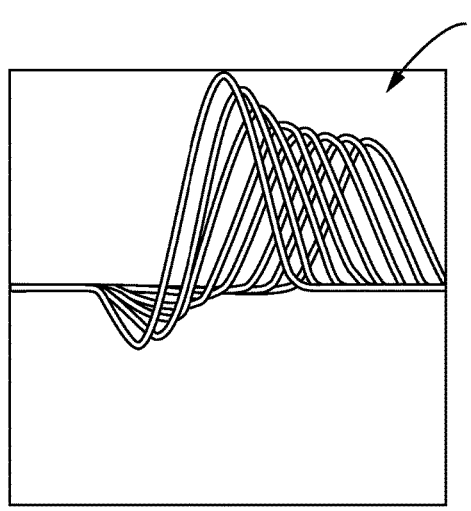
FIGS. 3A through 3D are plots illustrating simulated vs. derived "effective" water signatures (assuming water to be the wetting fluid).
Figure 3B:
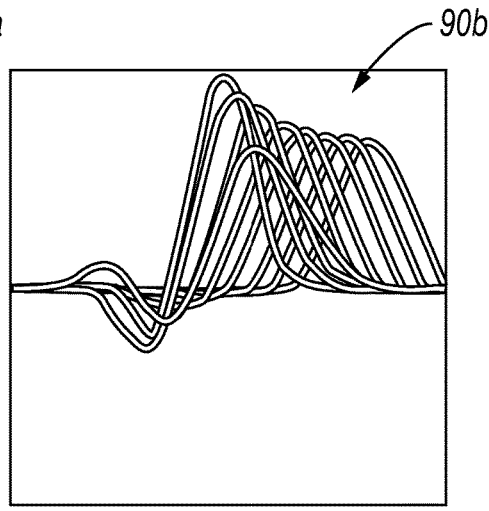

FIGS. 3A through 3D illustrate sets of simulated vs. derived "effective" water NMR T2 distribution signatures 90a-90d, and show they compare favorably. Depending upon actual bound fluid T2 thresholds or "cutoffs", the simulated signatures retain the same shape, but shift right or left, depending on longer or shorter bound fluid $T_2$ cutoffs, respectively. These unique dual-peak effective signatures (including one positive peak and one negative peak with correlated amplitudes) assist distinguishing water (i.e., the wetting fluid) from other non-wetting fluids present (e.g., oil or gas). FIG. 3A shows different simulated effective water signatures, excluding processing artifacts, shown to be similar within a horizontal shift. FIG. 3B shows simulated processing "regularization" artifacts, illustrating how additional peaks and/or troughs may result in practice. The smaller the pore spaces in the formations, the more pronounced the effects that will be exhibited in a plot such as in FIG. 3B.

Figure 3C:
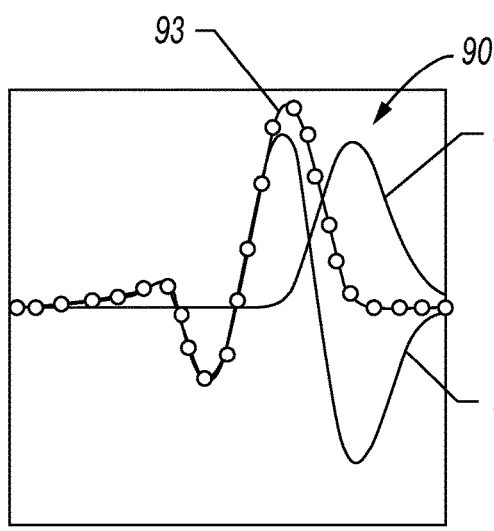
Figure 3D:
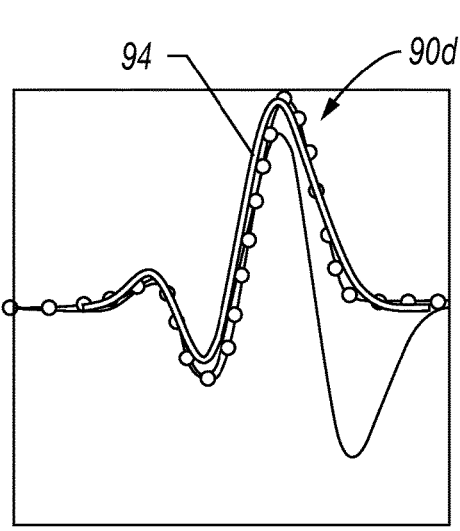

FIG. 3C includes plots showing a derived effective water signature using the well log example shown in FIG. 4 and derivation techniques described below. The curve 91 is identical to curve 213 that is shown in FIG. 21 and the curve 92 represents the derived drilling oil based mud (OBM) filtrate NMR log measurement signature at the same depth using derivation techniques described below. The curves 91, 92 were normalized using HI and polarization factor results from FIG. 22 and combined to reconstruct the curve 93 using reconstruction techniques described below. FIG. 3D shows the simulated effective water signature from FIG. 3C displayed against the actual signature from FIG. 3C, and shows a reasonable match represented by the curve 94.

Figure 4:
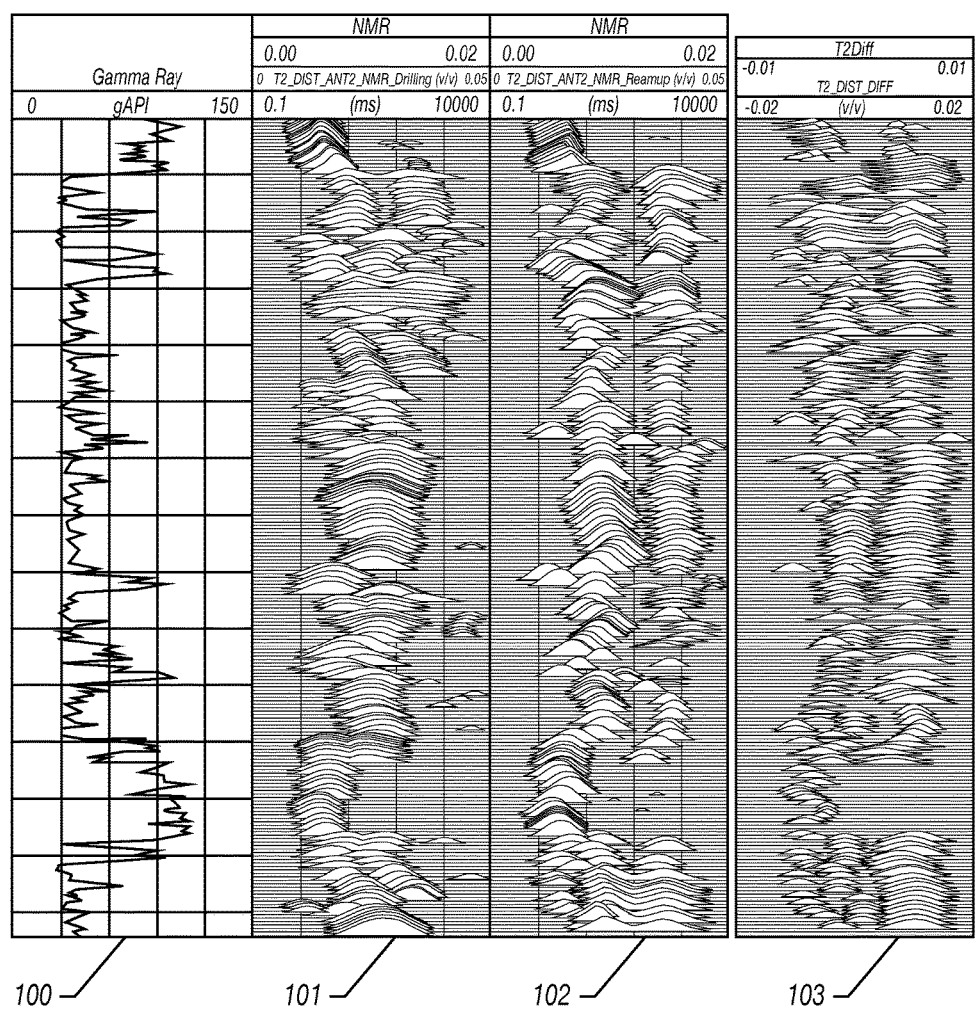
FIG. 4 are plots of a nuclear magnetic resonance ("NMR") dataset used as an example herein.

FIG. 4 shows the NMR data set used as an example herein. The tracks, from left to right, respectively, display a gamma-ray curve (track 100), NMR $T_2$ distributions from data acquired during drilling of the wellbore (i.e., the first measurement track 101), NMR $T_2$ distributions from a wipe pass (i.e., a second measurement—track 102), and the differential NMR $T_2$ distribution in-between both of the foregoing (i.e., resulting from subtracting the drilling measurements from the wipe pass measurement—track 103). Note the distinct non-wetting and wetting fluid modes on the wipe pass (non-wetting OBM filtrate and residual hydrocarbon mode(s) vs. wetting bound water mode(s)), separated by an NMR $T_2$ cutoff of approximately 90 msec.

Figure 5:
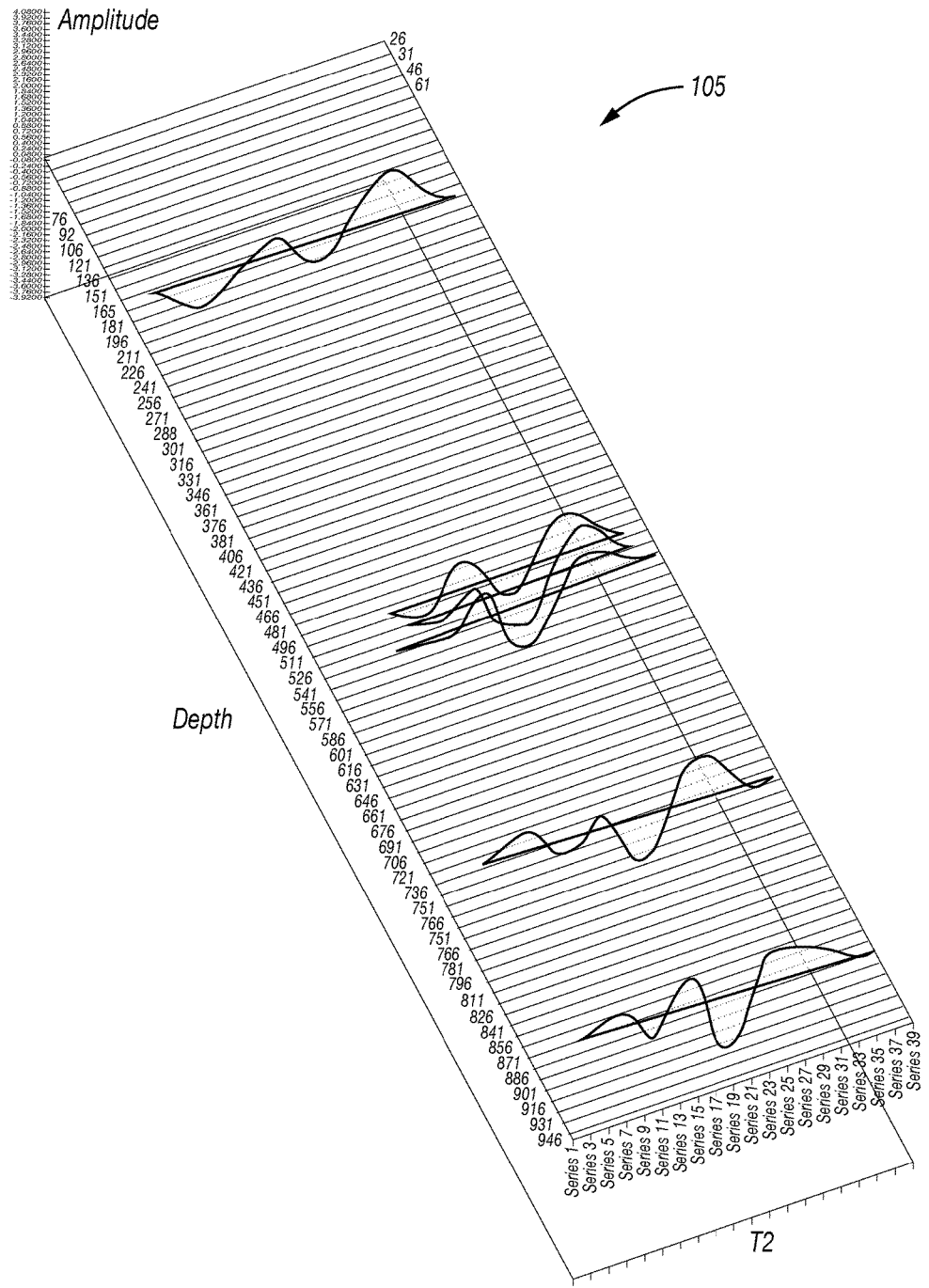
FIGS. 5 through 13 are plots illustrating the application of the pseudo-normalization techniques described above to the NMR dataset shown in FIG. 4, including clusters of pseudo-normalized patterns corresponding to different x-constituent pair exchanges, in accordance with this disclosure.

FIGS. 5 through 10 illustrate the application of the pseudo-normalization techniques described above. FIG. 5 is a series of depth plots 105 which illustrate a pseudo-normalization in which the norm is taken to be $\|\tilde{u}\|=\sqrt{\Sigma_i u_i^2}$, and where those data points with norm above a preset noise threshold $\|\Delta_{ij}(\tilde{M})\|>>70\% \|\Delta_{ij}(\tilde{M})\|_{Max}$ are displayed.

Figure 6:
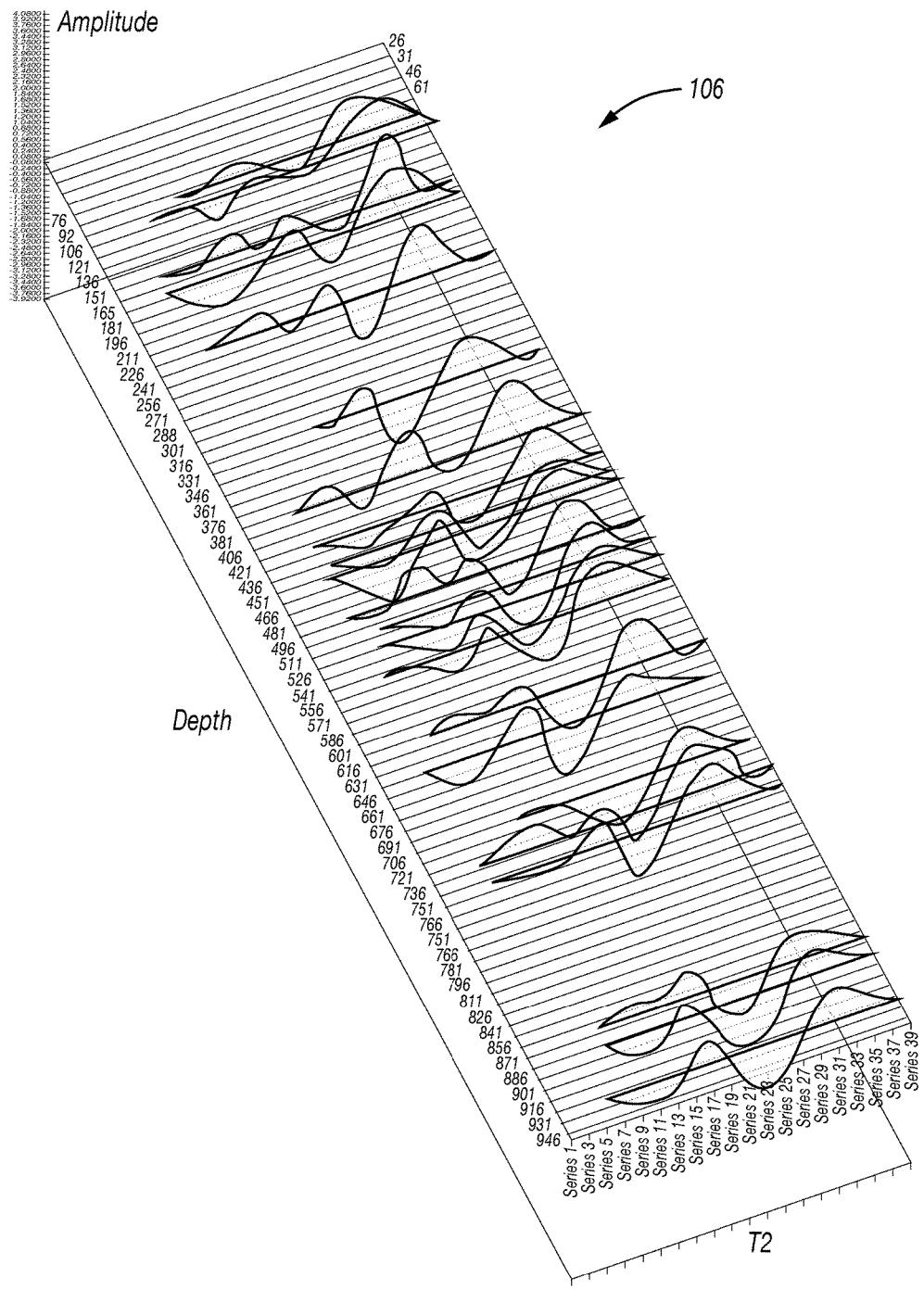

FIG. 6 is a series of depth plots 106 which illustrate a pseudo-normalization in which the norm is taken to be $\|\tilde{u}\|=\sqrt{\Sigma_i u_i^2}$, and where those data points with norm above a predetermined noise threshold $\|\Delta_{ij}(\tilde{M})\|>>50\% \|\Delta_{ij}(\tilde{M})\|_{Max}$ are displayed.

Figure 7:
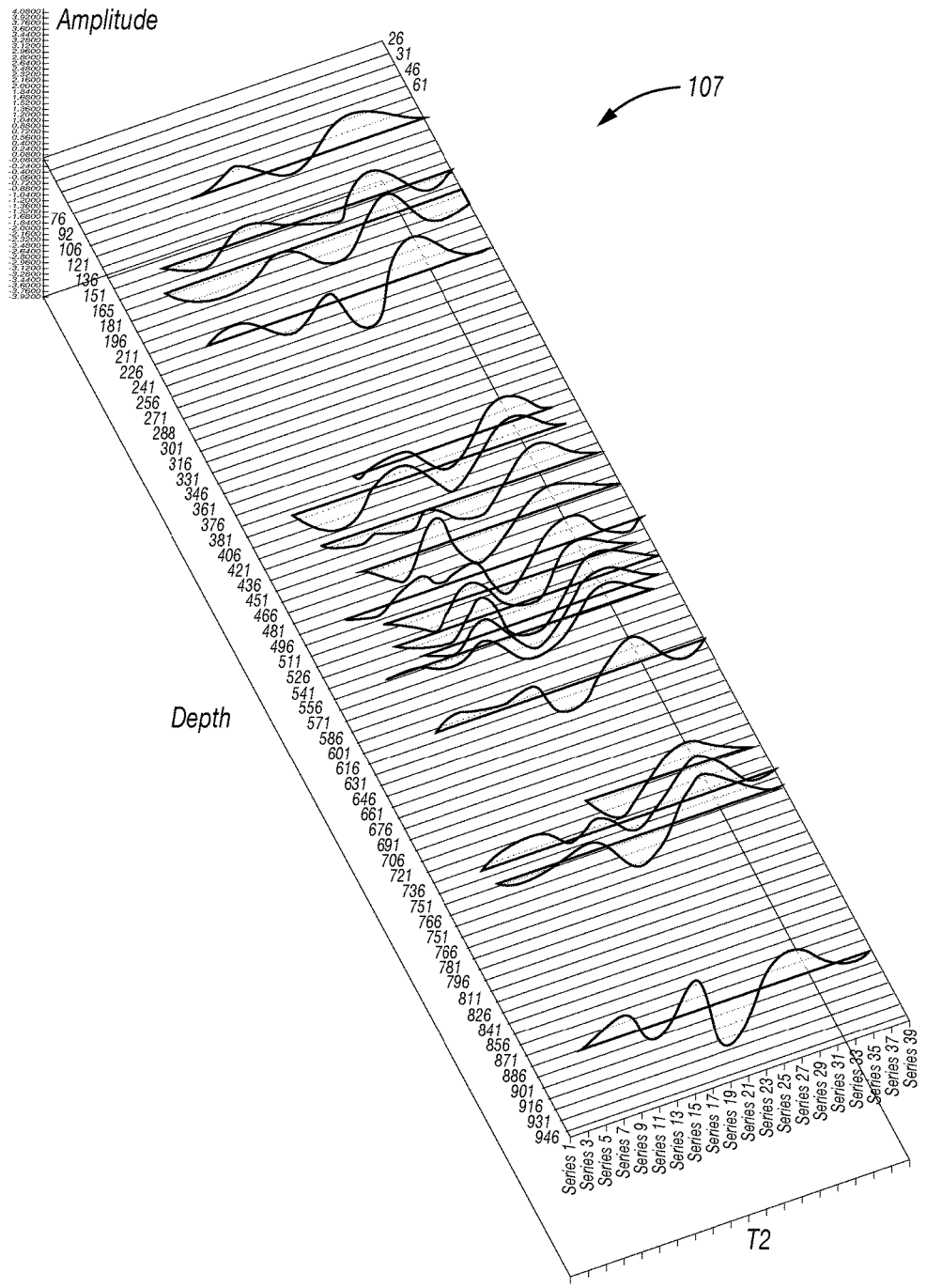

FIG. 7 is a series of depth plots 107 which illustrate a pseudo-normalization in which the norm is taken to be $\|\tilde{u}\|=\max_i (u_i)$, and where those data points with norm above a predetermined noise threshold $\|\Delta_{ij}(\tilde{M})\|>>50\% \|\Delta_{ij}(\tilde{M})\|_{Max}$ are displayed.

Figure 8:
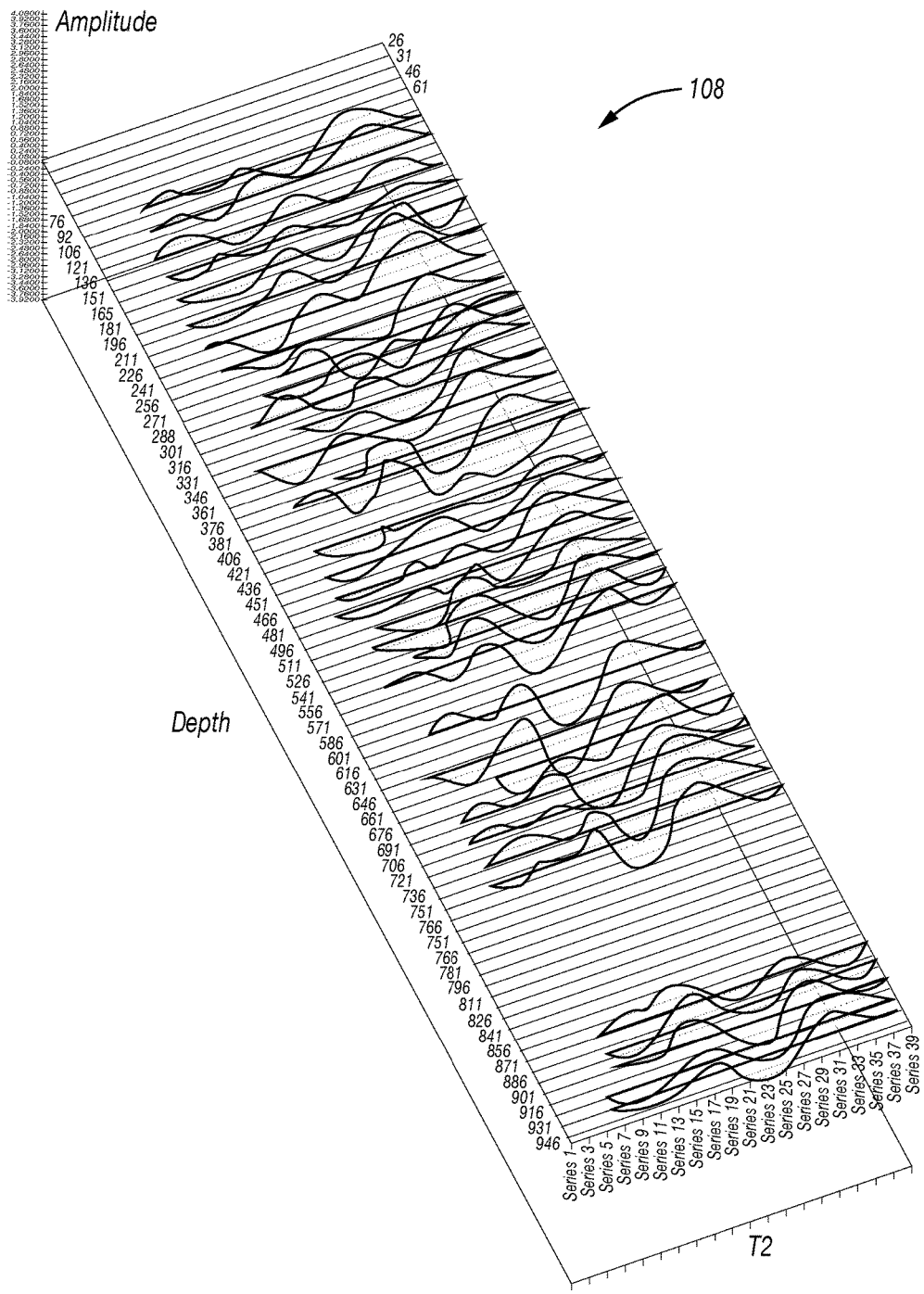

FIG. 8 is a series of depth plots 108 which illustrate a pseudo-normalization in which the norm is taken to be $\|\tilde{u}\|=\max_i (u_i)$, and where those data points with a norm above a predetermined noise threshold $\|\Delta_{ij}(\tilde{M})\|>>33\% \|\Delta_{ij}(\tilde{M})\|_{Max}$ are displayed.

Figure 9:
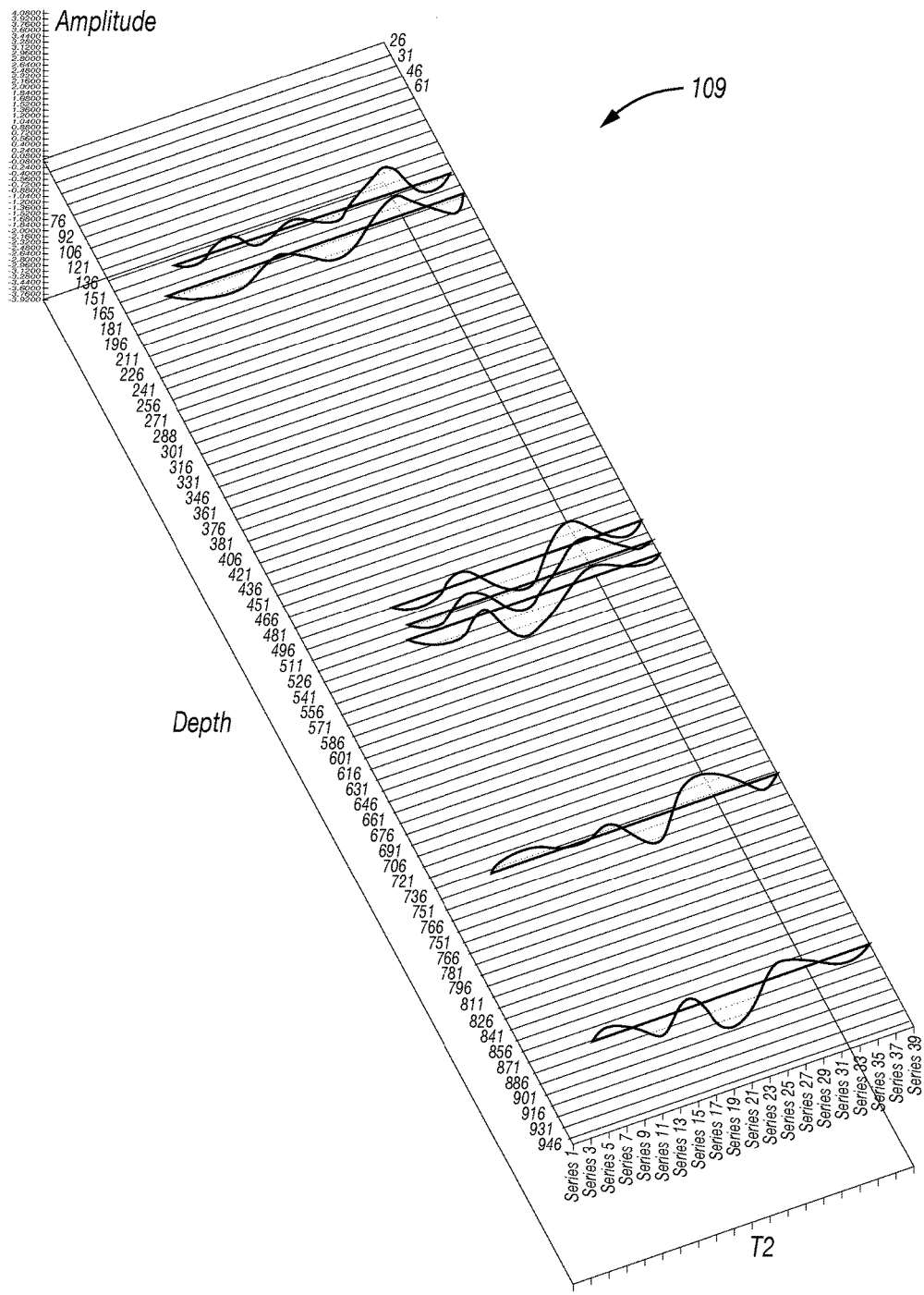

FIG. 9 is a series of depth plots 109 which illustrate a pseudo-normalization in which the norm is taken to be $\|\tilde{u}\|=\max_i (u_i)$, and where those data points with norm above a predetermined noise threshold $\|\Delta_{ij}(\tilde{M})\|>>66\% \|\Delta_{ij}(\tilde{M})\|_{Max}$ are displayed.

Figure 10:
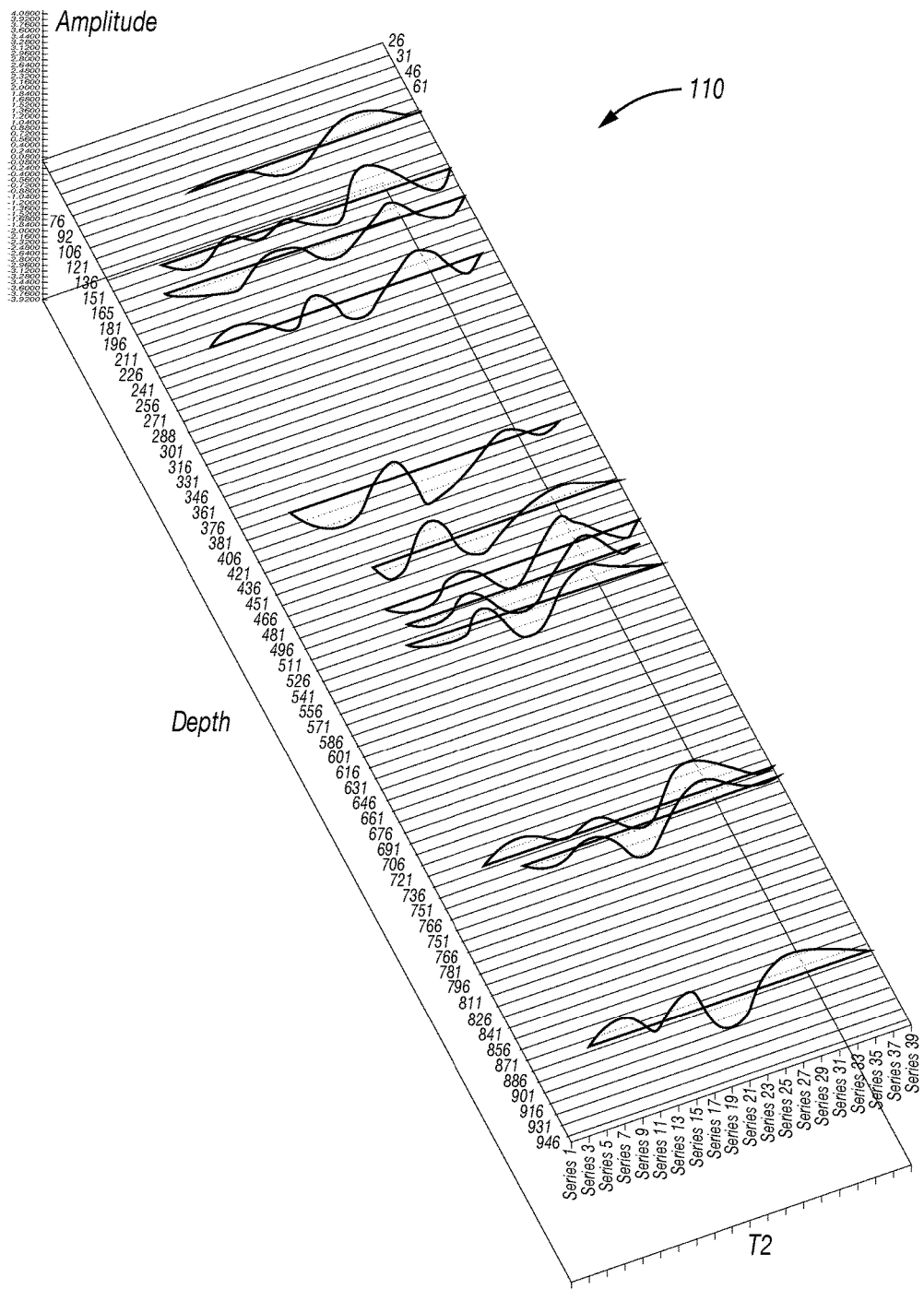

FIG. 10 is a series of depth plots 110 which illustrate a pseudo-normalization in which the norm is taken to be $\|\tilde{u}\|=\max_i (u_i)$, and where those data points with norm above a predetermined noise threshold $\|\Delta_{ij}(\tilde{M})\|>>55\% \|\Delta_{ij}(\tilde{M})\|_{Max}$ are displayed.

Figure 11:
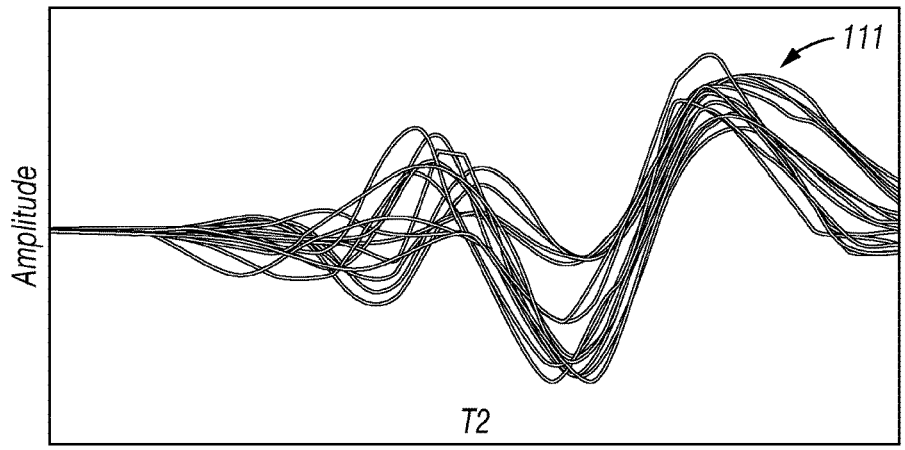
Figure 12:
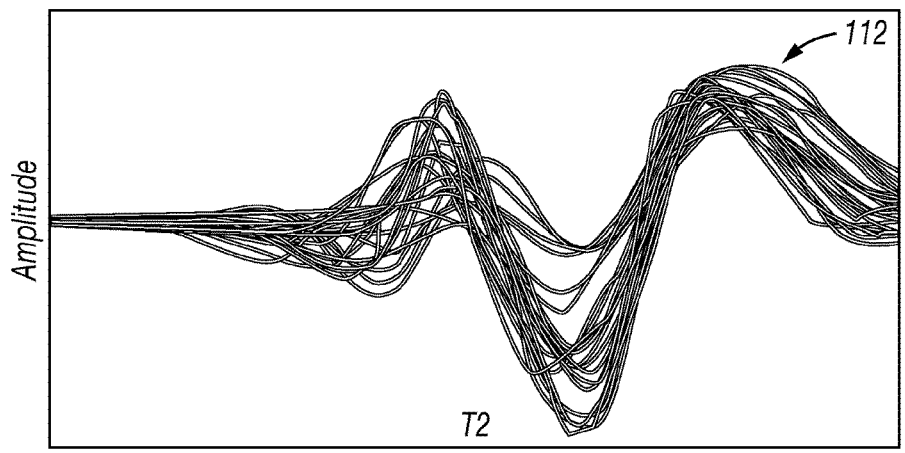
Figure 13:
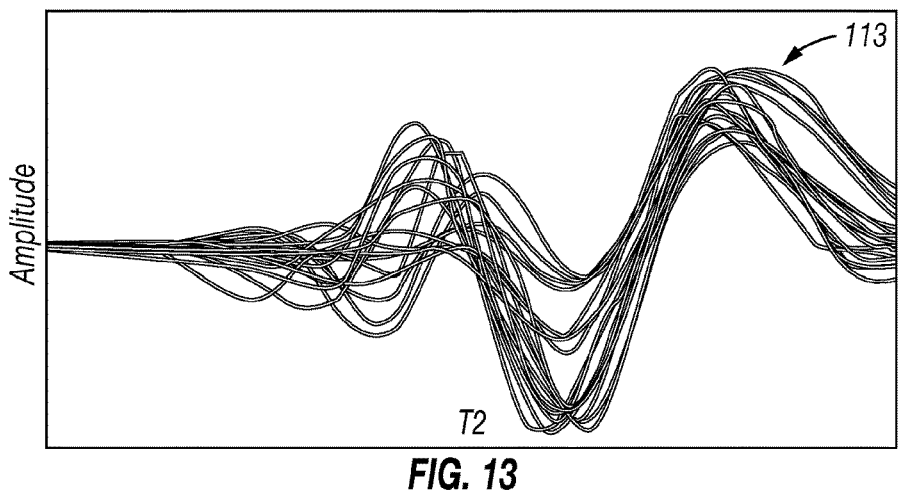

FIGS. 11 through 13 show pseudo-normalized patterns corresponding to different x-constituent pair exchanges. FIG. 11 shows selected patterns 111 resulting from x-constituent pair exchanges extracted using $\|\tilde{u}\|=\sqrt{\Sigma_i u_i^2}$. FIG. 12 shows selected patterns 112 resulting from x-constituent pair exchanges extracted using $\|\tilde{u}\|=\max_i (u_i)$. FIG. 13 shows selected patterns 113 resulting from x-constituent pair exchanges extracted using $\|\tilde{u}\|=\max_i (|u_i|)$.

Changes resulting from either log data acquisition or processing present different challenges. Data acquisition changes may be processed by making the explicit assumption that NMR measurements from the first log measurement can be converted into equivalent measurements from the second measurement, or vice versa. That way one is effectively comparing NMR datasets acquired with hypothetical likewise parameters. Processing-caused changes may generally be handled by considering the resulting low-amplitude peaks and troughs as just noise, requiring the corresponding noise threshold level to be raised.

One consequence of pseudo-normalization, is that clusters of x-constituent substitution data points corresponding to parallel vectors may not be distinguishable from each other. Furthermore, clusters of x-constituent substitution data points gathered around the origin "O" and corresponding to a pair of constituents with similar properties, such as native formation oil being displaced by drilling oil base mud (OBM) filtrate, or native formation water being displaced by drilling water base mud (WBM) filtrate, may not be distinguishable conclusively from other clusters of data points corresponding to other x-constituent pair exchanges. These considerations are addressed below.

In another example, it may be assumed that one can estimate the quantity of one of the constituents, for example constituent "J", that has participated in the x-constituent substitution. This may be realized in a number of ways, such as using, for example, NMR, resistivity, SIGMA, dielectric, gamma-ray, litho-density/neutron, or acoustic measurements, depending on the situation encountered. In this case, other constituents' properties can be reconstructed precisely, and hence the expression "true normalization" is introduced here, in contradistinction to pseudo-normalization, according to the expressions:

$$\Delta_{ij}(\vec{M}) = \Delta_{ij}(V_J)\cdot(\vec{M}_J - \vec{M}_I) = \Delta_{ij}(V_I)\cdot(\vec{M}_I - \vec{M}_J)$$

and $$\vec{M}_I = \vec{M}_J - \frac{\Delta_{ij}(\vec{M})}{\Delta_{ij}(V_J)},$$

where constituent "I" is the other constituent participating in the substitution, and can be further "propagated" to yet other constituents. This reconstruction addresses the considerations discussed earlier, namely where different x-constituent exchanges result in parallel vectors $\Delta_{ij}(\vec{M})$, or where limited contrast between constituents "I" and "J" resulted in vectors $\Delta_{ij}(\vec{M})\approx\vec{0}$.

FIG. 16A displays the vectors $$\frac{\Delta_{ij}(\vec{M})}{\Delta_{ij}(V_J)}$$

with true normalization. Data points resulting from true normalization, which prior to true normalization may be clustered along the different x-constituent substitution lines, now regroup further and coalesce around the large dots shown in the figure. FIG. 16B displays the relationship(s)

$$\vec{M}_I = \vec{M}_J - \frac{\Delta_{ij}(\vec{M})}{\Delta_{ij}(V_J)}$$

versus FIG. 2A, illustrating how the proper constituents' log measurements signatures are reconstructed. (FIG. 16A was rotated 180° to produce the term $$-\frac{\Delta_{ij}(\vec{M})}{\Delta_{ij}(V_J)}).$$

The situation may also arise, such as when working with NMR measurements, in which the quantity of one of the constituents that has participated in the x-constituent substitution is known to within a constant factor, and not in absolute value. For example, the volume of drilling mud filtrate indicated on NMR distributions, in the case of conventional overbalance drilling, is known to within its HI and the polarization factor, which additionally may not be known at downhole in-situ conditions. The volume of drilling mud filtrate indicated on NMR distributions may then be referred to as an "apparent" drilling mud filtrate volume, versus "true" mud filtrate volume after adjusting for HI and polarization factor, for the foregoing reason.

In this case, the equations above can be adapted as follows:

$$\Delta_{ij}(\tilde{M}) = \Delta_{ij}(V_J) \cdot (\tilde{M}_J - \tilde{M}_I) = \Delta_{ij}(V_I) \cdot (\tilde{M}_I - \tilde{M}_J)$$

$$\Delta_{ij}(\tilde{M}) = \frac{\Delta_{ij}(V_J)^{apparent}}{HI_J \cdot Pol_J} \cdot (HI_J \cdot Pol_J \times \tilde{M}_J^{norm.} - HI_I \cdot Pol_I \times \tilde{M}_I^{norm.}) =$$

$$\frac{\Delta_{ij}(V_I)^{apparent}}{HI_J \cdot Pol_J} \cdot (HI_I \cdot Pol_I \times \tilde{M}_I^{norm.} - HI_J \cdot Pol_J \times M_J^{norm.})$$

$$\Delta_{ij}(\tilde{M}) = \Delta_{ij}(V_J)^{apparent} \cdot \left( \tilde{M}_J^{norm.} - \frac{HI_I \cdot Pol_I}{HI_J \cdot Pol_J} \times \tilde{M}_I^{norm.} \right) =$$

$$\Delta_{ij}(V_I)^{apparent} \cdot \left( \frac{HI_I \cdot Pol_I}{HI_J \cdot Pol_J} \times \tilde{M}_I^{norm.} - \tilde{M}_J^{norm.} \right)$$

and $$\frac{HI_I \cdot Pol_I}{HI_J \cdot Pol_J} \times \tilde{M}_I^{norm.} = \tilde{M}_J^{norm.} - \frac{\Delta_{ij}(\tilde{M})}{\Delta_{ij}(V_J)^{apparent}}$$

or $$\tilde{M}_I = HI_J \cdot Pol_J \times \left\{ \tilde{M}_J^{norm.} - \frac{\Delta_{ij}(\tilde{M})}{\Delta_{ij}(V_J)^{apparent}} \right\}$$

where "HI" represents the hydrogen index and "Pol" represents the polarization factor, and $\tilde{M}_I^{norm.}$ and $\tilde{M}_J^{norm.}$ stand for constituents "I" and "J" normalized NMR log measurement signatures (which means here "normalized to 100 p.u. response", or in the specific case of NMR distributions, with "total area under the NMR distribution equal to 100 p.u."), that is excluding HI and polarization factor effects.

FIG. 16C displays the vectors $$\frac{\Delta_{ij}(\tilde{M})}{\Delta_{ij}(V_J)^{apparent}},$$

for the case of "apparent" normalization (in contrast to true normalization) using the apparent drilling mud filtrate volume. Data points resulting from such normalization now coalesce around the "zoomed-in" (or "zoomed-out", as the case may be) large dots shown on the figure, as compared to true normalization which involves using the proper drilling mud filtrate. FIG. 16D displays the relationship(s)

$$\tilde{M}_J^{norm.} - \frac{\Delta_{ij}(\tilde{M})}{\Delta_{ij}(V_J)^{apparent}}$$

versus FIG. 2A, illustrating how the apparent constituents' log measurements signatures are reconstructed. (FIG. 16C was rotated 180° to produce the term $$-\frac{\Delta_{ij}(\tilde{M})}{\Delta_{ij}(V_J)^{apparent}}.)$$

As can be seen, the reconstructed log responses still fall along the vectors displayed in the background, meaning and confirming that they differ from the true constituents' log measurements signatures by a constant or scaling factor— namely $HI_J \cdot Pol_J$. It is then enough that the NMR log response of one of the constituents participating in the x-constituent substitutions be known to determine the scaling factor used to reconstruct the other coupled constituents' true log measurements signatures.

Certain conclusions may be derived at this point. For instance, the statistical analysis and classification techniques described earlier (using histograms, artificial NN classification schemes, or factor analysis or PCA methodology) may also apply following "true" or "apparent" normalization (in contradistinction to pseudo-normalization), which are respectively expressed as $$\frac{\Delta_{ij}(\vec{M})}{\Delta_{ij}(V_J)} \text{ or } \frac{\Delta_{ij}(\tilde{M})}{\Delta_{ij}(V_J)^{apparent}},$$

in order to identify also those x-constituent substitution patterns which may be missed using pseudo-normalization alone (i.e. where different x-constituent exchanges result in parallel vectors $\Delta_{ij}(\vec{M})$, or where limited contrast between constituents "I" and "J" resulted in vectors $\Delta_{ij}(\vec{M}) \approx \vec{0}$).

It is in fact sufficient that the NMR measurement signature of one of the constituents (generally water) participating in the x-constituent substitutions be known, for other coupled constituents' NMR measurements signatures to be reconstructed, whereby the HI and polarization factor corrections or adjustments are determined first, and the actual responses determined second. This can be expressed as:

$$\tilde{M}_I = HI_J \times Pol_J \times \left\{ \tilde{M}_J^{norm.} - \frac{\Delta_{ij}(\tilde{M})}{\Delta_{ij}(V_J)^{apparent}} \right\}$$

$$HI_I \cdot Pol_I = HI_J \cdot Pol_J \times \left( 100 p.u. - \frac{\Delta_{ij}(Phi(\tilde{M}))}{\Delta_{ij}(V_J)^{apparent}} \right)$$

$$\begin{cases} HI_J \cdot Pol_J = \dfrac{HI_I \cdot Pol_I}{\left(1 - \dfrac{\Delta_{ij}(Phi(\tilde{M}))}{\Delta_{ij}(V_J)^{apparent}}\right)} = \dfrac{HI_I \cdot Pol_I}{(1 - Slope_{IJ\ pair\ exchange})} \\ HI_K \cdot Pol_K = HI_J \cdot Pol_J \times \left(1 - \dfrac{\Delta_{ij}(Phi(\tilde{M}))}{\Delta_{ij}(V_J)^{apparent}}\right) = HI_J \cdot \\ \qquad Pol_J \times (1 - Slope_{KJ\ pair\ exchange}) \end{cases}$$

where "J" is the constituent substituting constituents "I" or "K", and constituent "I" is the one with known a priori $HI_I$. $Pol_I$, in which case $HI_J \cdot Pol_J$ is determined first and other $HI_K \cdot Pol_K$ are determined second. The newly introduced term "Phi($\tilde{M}$)" represents the NMR measured porosity (i.e. the total "area under the distribution "$\tilde{M}$" in the specific case of NMR distributions), and the term "$\Delta_{ij}$ (Phi($\tilde{M}$))" represent the difference in NMR measured porosity between the snapshots no. "j" and no. "i". The newly introduced terms "$Slope_{IJ\ pair\ exchange}$" and "$Slope_{KJ\ pair\ exchange}$" are with reference to a new family of cross-plots, with $\Delta_{ij}(V_J)^{apparent}$ as the "X axis" and $\Delta_{ij}$ (Phi($\tilde{M}$)) as the "Y axis". The "Slopes" correspond to those of straight lines passing through the origin.

FIG. 17A illustrates the new family of cross-plots, with $\Delta_{ij}(V_J)^{apparent}$ as the x-axis and $\Delta_{ij}$ (Phi($\tilde{M}$)) as the y-axis. Data points resulting from different x-constituent substitution(s) cluster along lines with a different slope, according to the HI. Pol. of each constituent. The 2-D (two-dimensional) diagram of FIG. 17A may be extended to multiple dimensions. In the case of multi-dimensional displays, clusters of vectors ($\Delta_{ij}(\vec{M})$, $\Delta_{ij}(V_J)^{apparent}$) may be considered and histograms plotted per the solid angle. Another useful cross-plot technique is to plot with $\Delta_{ij}(V_I)^{apparent}$ as the (y-axis) and $\Delta_{ij}(V_J)^{apparent}$ as the x-axis, in which case the various slopes would read $$\frac{HI_I \cdot Pol_I}{HI_J \cdot Pol_J},$$

as shown in FIG. 17B. FIG. 17B illustrates data points resulting from different x-constituent substitution(s), clustering along lines with different slopes, according to the HI. Pol. of each constituent.

FIGS. 21, 22, and 3B sequentially show how this works, using a practical example. However, whereas the hydrogen index and polarization factor corrections derived as shown in FIG. 21 may be considered as reliable, the same may not necessarily be true of the derived NMR log measurement responses $\tilde{M}$ due to the adverse effects of processing in general, and regularization in particular, as mentioned earlier. The NMR exception may instead dictate that different fluid NMR log responses be derived using the constrained nonlinear least squares fitting techniques applied in the examples of FIGS. 26A through 26F and 27A through 27H to circumvent these adverse effects. The equivalent of FIG. 21 may also be performed in spin echo amplitude space. That is, instead of subtracting distributions from each other, one may subtract echo train amplitudes from each other first, and then invert the resulting echo train differences. Some constraints may be introduced to avoid inversion instability from both positive and negative amplitudes to be present simultaneously in such a differential echo train. Factor analysis or PCA may also apply here, including application in a constrained fashion.

FIG. 18 includes a series of depth plots 180 illustrating pseudo-normalization results in which the norm is taken to be $\|\tilde{u}\| = FF_{T2\ cutoff\ 90\ msec}^{wipe}$ (i.e the apparent free fluid volume using a T2 cutoff of 90 msec, and where those data points with norm above a predetermined noise threshold $\|\Delta_{ij}(\tilde{M})\| >> 75\% \|\Delta_{ij}(\tilde{M})\|_{Max}$ are displayed. FIG. 19 includes a series of depth plots 190 which illustrates pseudo-normalization results, where the norm is taken to be $\|\tilde{u}\| = FF_{T2\ cutoff\ 90\ msec}^{wipe}$, and where those data points with norm above a predetermined noise threshold $\|\Delta_{ij}(\tilde{M})\| >> 63\% \|\Delta_{ij}(\tilde{M})\|_{Max}$ are displayed. FIG. 20 includes a series of depth plots 199 which illustrates pseudo-normalization results, where the norm is taken to be $\|\tilde{u}\| = FF_{T2\ cutoff\ 90\ msec}^{wipe}$, and where those data points with norm above a predetermined noise threshold $\|\Delta_{ij}(\tilde{M})\| >> 50\% \|\Delta_{ij}(\tilde{M})\|_{Max}$ are displayed. FIG. 21 shows true normalized patterns 210 corresponding to different x-constituent pair exchanges, where the volume of drilling OBM filtrate participating in the x-constituent pair exchanges was made equal to $FF_{T2\ cutoff\ 90\ msec}^{wipe}$. Distributions that are "active" in the short $T_2$ distribution spectrum were excluded to guard against noise and depth mismatch artifacts. The patterns 211-213 correspond to the arithmetic average of the background (i.e. lighter shaded) curves. The patterns 210 shown hint at two different non-wetting hydrocarbon fluids and one wetting fluid (water).

FIG. 22 illustrates how the combined effects of HI and polarization factor are identified and then adjusted. Data points corresponding to fluids with the same HI. Pol. will cluster along lines with identical slopes, or they may result in distinctive peaks (or modes) on a histogram of the corresponding slopes. The "X axis" in this instance corresponds to the apparent volume of drilling OBM filtrate from the wipe pass, and the "Y axis" corresponds to the change in total NMR porosity in-between the drill and wipe pass. The water point is taken to indicate a combined HI and polarization factor of one (i.e. 100 p.u.), which then sets the value for drilling OBM filtrate HI. Pol. That value can in turn be propagated to the other two unknown hydrocarbon fluids identified. One relevant consideration when carrying out this procedure, is when estimating $\Delta_{ij}(V_j)^{apparent}$ (i.e. the volume of drilling OBM filtrate in this example) from $FF_{T2\ cutoff\ 90\ msec}^{wipe}$, the latter may be contaminated by residual free fluids from the drill pass.

While there is interest in identifying the patterns resulting from x-constituent substitution when the substitution occurs in pairs, there is at least one exception to the long-held belief that when the individual constituents' log measurements signatures have been assigned, can the actual well log measurements be converted into elemental volumetric fractions. A counter-intuitive example will now be explained whereby different constituents' log measurements signatures do not have to be calibrated individually, but rather "a group of constituents" may be implicitly characterized simultaneously and assigned a single novel explicit "group signature", and where the substitution does not have to occur in pairs. The specific example used to describe how this works refers to true porosity.

Figure 14A:
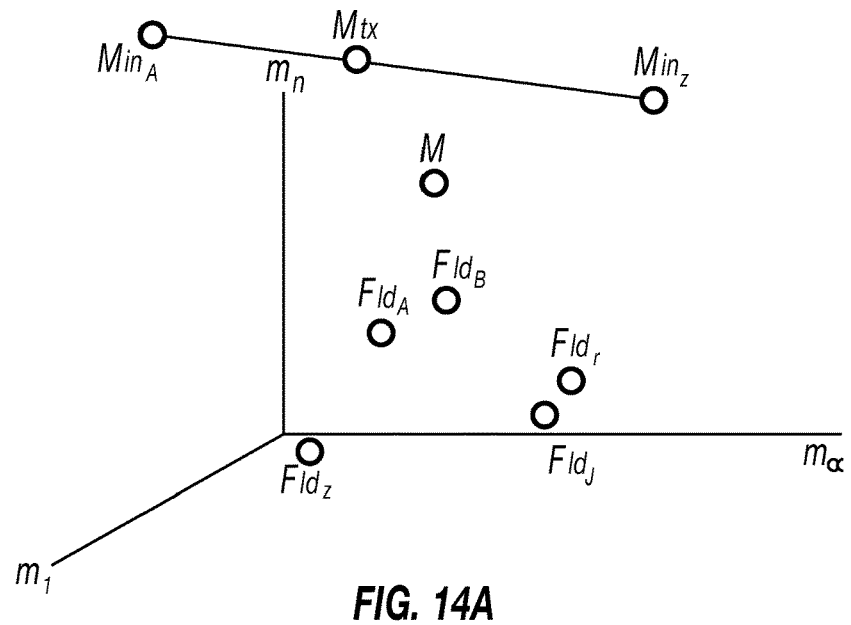
FIG. 14A-14G are graphs illustrating the concept of porosity hyper-space, defined as the multi-dimensional space containing the log measurement endpoints of those constituents present inside the pore space of the formation, and the application of such concept for determining porosity in accordance with an example embodiment.
Figure 14B:
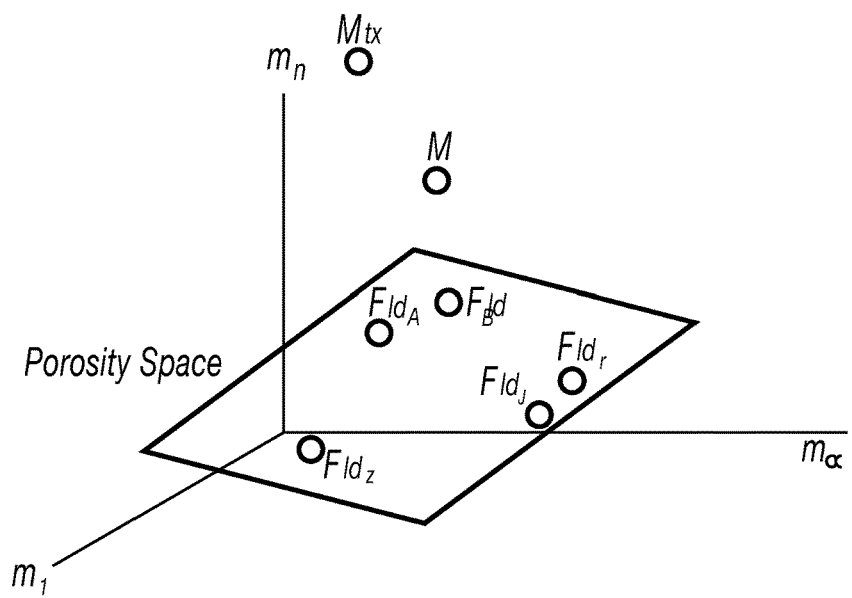
Figure 14C:
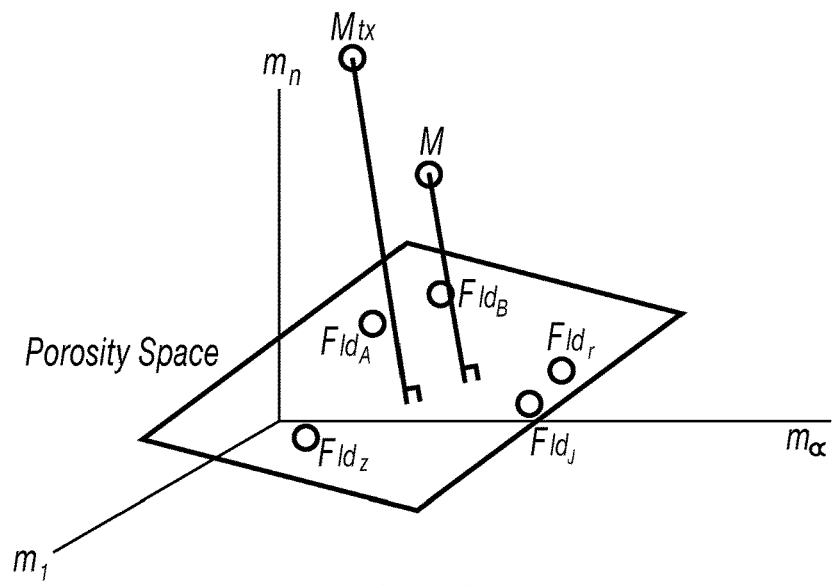
Figure 14D:
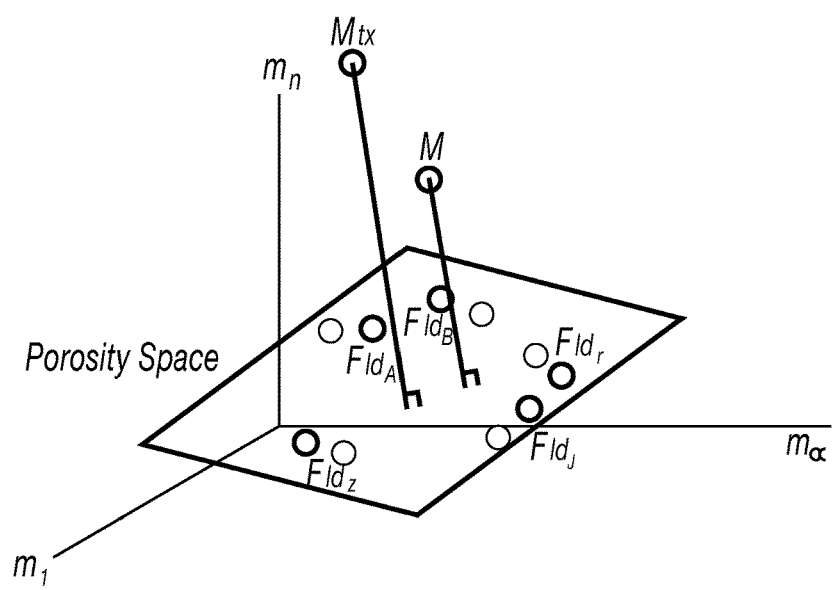
Figure 14E:
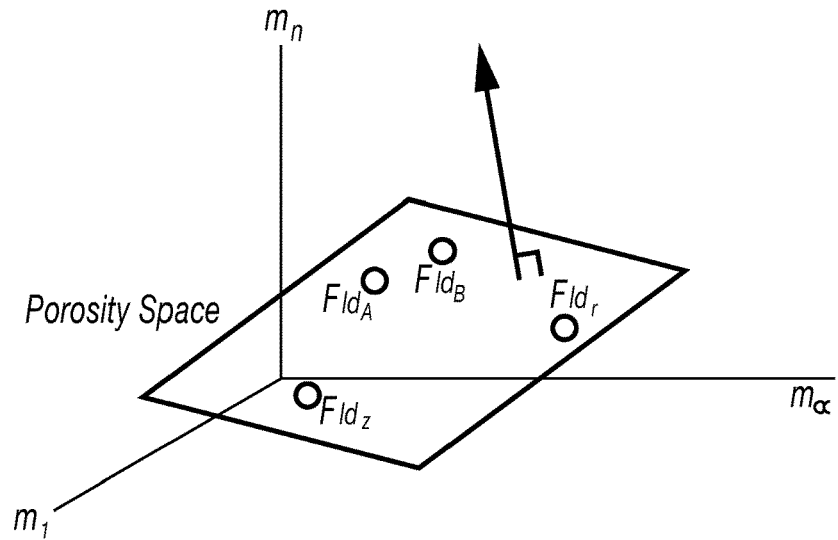
Figure 14F:
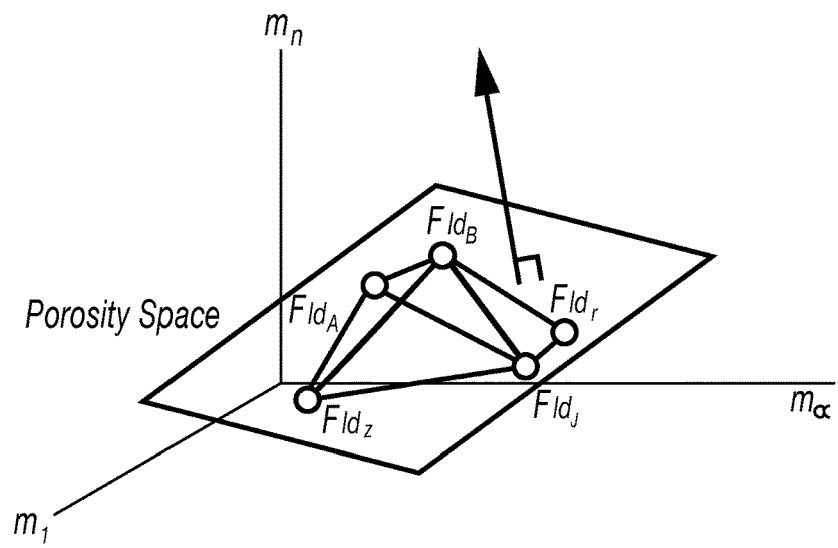
Figure 14G:
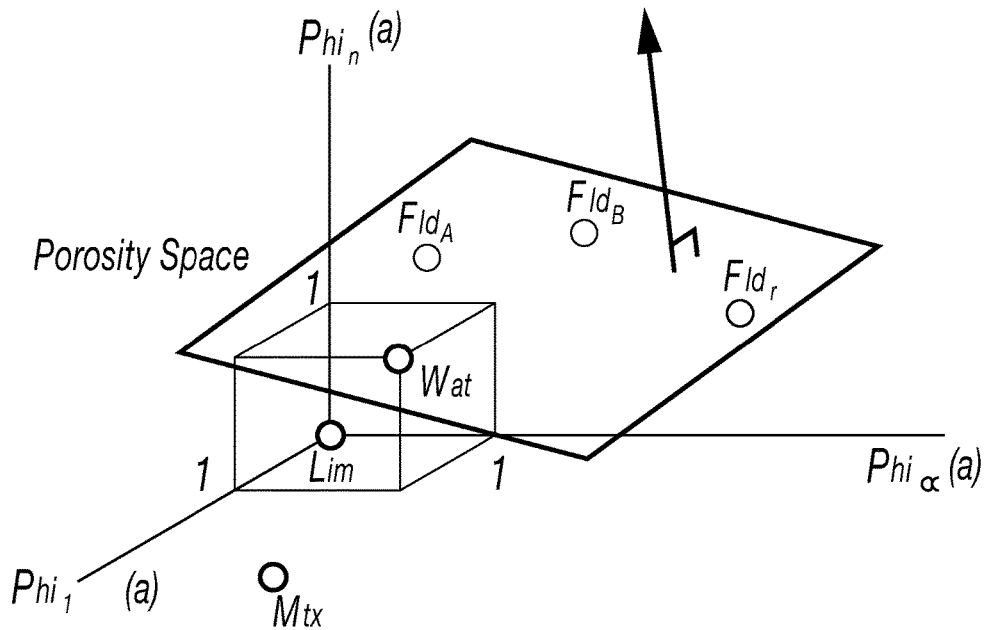
Figure 15:
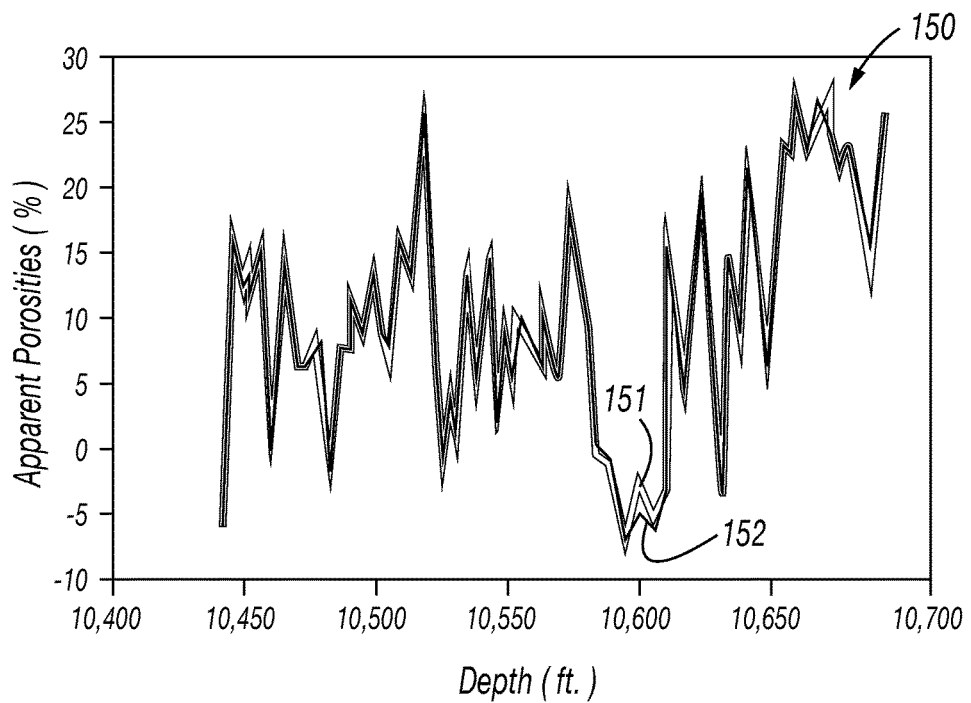
FIG. 15 is a graph illustrating an example minimization in accordance with an example embodiment where the fluids present were water, oil, and gas, and the measurements considered were bulk density, neutron porosity, and thermal neutron capture cross-section (SIGMA).

FIGS. 14A through 15 illustrate this situation, leading to the characterization of the "porosity space" (or "porosity hyper-plane" in case of a space with dimension "n−1"), which is a new concept defined below. FIG. 14A shows different fluid end-points "Fld$_A$, Fld$_B$, Fld$_I$, Fld$_J$, Fld$_Z$", and a single equivalent matrix end-point (i.e. a single point representing the rock mineralogy of the underground formation) "Mtx" instead of different individual mineral end-points ("Min$_A$, Min$_Z$", for example). A measurement point "M" is also shown. Where the different considered well log measurements "m$_1$, ... m$_\alpha$, ... m$_n$" mixing laws are linear (in the volumetric sense), the measurement point "M" corresponds to the "center of gravity" of the aforementioned fluid and matrix end-points, as weighted by the corresponding volumetric percentage fractions present inside the volume of formation being measured. FIG. 14B shows what has been termed herein the "porosity space" which is spanned by the fluid end-points "Fld$_A$, Fld$_B$, Fld$_I$, Fld$_Z$".

FIG. 14C shows a geometrical visualization of the true porosity measurement of the underground formation, computed as "1" minus the ratio of the distance of the measurement point "M" to the porosity space, to the distance of the matrix end-point "Mtx" to the porosity space. FIG. 14D shows that movements or displacements of the fluid end-points "Fld$_A$, Fld$_B$, Fld$_I$, Fld$_J$, Fld$_Z$" about the porosity space do not affect in any way the computed true porosity. True porosity, therefore, depends on the porosity space position and orientation as a whole, but not on the specific position of individual fluid end-points in that porosity space. In the case of working with NMR measurements, the same concept and techniques can apply. However, it is noted that in practice, the porosity space would be spanned by the corresponding non-wetting fluids NMR signatures and wetting fluids NMR "effective" signatures, which were introduced and which existence was demonstrated earlier in this description.

FIG. 14E indicates that a hyper-plane for example, can be well-defined by a vector orthogonal to it and a point belonging to it (point "Fld$_Z$" in this figure). While this definition is very convenient, it clearly is not unique. Strictly speaking, "n" parameters may be used to define a hyper-plane of dimension "n−1" inside "n" dimensions. In the general case, where "n" fluid constituents are present inside the porosity, the matrix is represented by a single equivalent matrix point, and "n" measurements are considered, the calculation of porosity may involve "n" parameters being known, in contradistinction to the "n²" parameters that would have been used to characterize the "n" fluid constituent end-points individually.

FIG. 14F shows how the porosity hyper-plane may be characterized in practice. When the pore space in the sample of the formation being measured is occupied by different fluids that may substitute each other and the measurement repeated, then the measurement point "M" will move about in a hyper-plane parallel to the porosity hyper-plane. The observation or combination of such measurements points' displacement vectors will uniquely define the orientation of the porosity hyper-plane (i.e. will uniquely define the direction of the vector orthogonal to such porosity hyper-plane). Furthermore, the fluid constituents do not have to be exchanged in pairs, but possibly in triplets, etc.

More specifically, the mathematical expression for the distance of any measurement point "M" to the porosity hyper-plane is simply a linear sum of the type:

$$d(M) = p_0 + p_1 \cdot m_1 + \ldots + p_\alpha \cdot m_\alpha + \ldots + p_n \cdot m_n$$

where "$p_0, p_1, \ldots p_\alpha, \ldots p_n$", are constant parameters describing the orientation and position of the porosity hyper-plane in space, (with $(p_1)^2 + \ldots (p_\alpha)^2 + \ldots (p_n)^2 = 1$).

The appropriate parameters "$p_0, p_1, \ldots p_\alpha, \ldots p_n$", to use may be determined using various methods. One such method would be to use the porosity from core data as a reference, and express true porosity as a linear combination of the measurements available, plus a constant. A match may then be made between the two sets of data.

For the present example, an entire wellbore section may be logged while drilling ("drill pass" snapshot). The same section may be re-logged after drilling ("wipe pass" or "ream-up pass" snapshot), where different fluids may occupy the same pore space at different times, assuming conventional overbalance drilling. The particular parameters "$p_0, p_1, \ldots p_\alpha, \ldots p_n$", may be searched which minimize the difference between "$d(M^{(drill)})$" and "$d(M^{(wipe)})$" over the entire section logged, while constraining "$d(M_{(FldZ)}) = 0$". This operation serves to uniquely define the porosity hyper-plane orientation and position in space.

An expression may be obtained, when the considered measurements "$m_1, \ldots m_\alpha, \ldots m_n$", are first converted into corresponding "apparent porosity" measurements "$Phi_1^{(a)}, \ldots Phi_\alpha^{(a)}, \ldots Phi_n^{(a)}$". The process of converting measurements into apparent porosities is based upon both an assumed a priori matrix composition, and an assumed a priori composition of the fluid occupying the pore space of the rock. For the sake of argument, it may be that the matrix is assumed to be limestone ("Lim"), and the fluid is assumed to be water of a particular salinity ("Wat"). This means, in practice, that when the matrix happens to be actually limestone and the fluid happens to be actually water, then the apparent porosity measurements "$Phi_1^{(a)}, \ldots Phi_\alpha^{(a)}, \ldots Phi_n^{(a)}$" will be equal to each other and equal to the true porosity of the formation.

In practice, the following considerations may be taken into account for the selection of the matrix and fluid types assumed a priori to convert measurements into apparent porosities. The fluid assumption used in the apparent porosities should be one of the fluids present. If free water is present, either as formation water or as WBM filtrate, then that water may be used for the apparent porosities. For the apparent matrix, the predominant lithology that will be encountered may be used.

FIG. 14G shows how the prior FIGS. (14A-14F) may be modified when working with apparent porosity measurements instead of the measurements themselves. Basically, the "Lim" end-point is now located at the origin and the "Wat" end-point has coordinates $(1, 1, \ldots, 1)$. This is very convenient because a new apparent porosity "$PHI^{(a)}_{P1, \ldots P\alpha, \ldots Pn}$" may be introduced, defined as a linear mixture of traditional apparent porosities:

$$PHI^{(a)}_{P1, \ldots P\alpha, \ldots Pn} = P_0 \cdot Phi_1^{(a)} + \ldots + P_\alpha \cdot Phi_\alpha^{(a)} + \ldots + P_n \cdot Phi_n^{(a)}$$

Moreover, the foregoing procedure to minimize the difference between "$d(M^{(drill)})$" and "$d(M^{(wipe)})$", may be replaced by searching for those particular parameters "$P_1, \ldots P_\alpha, \ldots P_n$" parameters, that minimize the difference between the apparent porosities "$(PHI^{(a)}_{P1, \ldots P\alpha, \ldots Pn})^{(drill)}$" and "$(PHI^{(a)}_{P1, \ldots P\alpha, \ldots Pn})^{(wipe)}$" over the entire section logged, while constraining "$PHI^{(a)}_{P1, \ldots P\alpha, \ldots Pn}(Wat) = P_0 + \ldots + P_\alpha + \ldots + P_n = 1$".

FIG. 15 shows a graph 150 of an actual example of such a minimization, where the fluids present were water, oil, and gas, and the measurements considered were bulk density, neutron porosity, and SIGMA. The figure displays the apparent porosities "$(PHI^{(a)}_{P1, P\alpha, Pn})^{(drill)}$" and "$(PHI^{(a)}_{P1, P\alpha, Pn})^{(wipe)}$" on the vertical axis versus depth on the horizontal axis following the optimization process described above. As will be observed, a substantial overlay results between the drill pass (curve 151) and the wipe pass (curve 152) computed apparent porosity measurements.

The resulting apparent porosity "$PHI^{(a)}_{P1, \ldots P\alpha, \ldots Pn}$", did not dictate that the oil and gas parameters be known (which in fact may be extremely difficult to model in practice), and may be readily applied to nearby offset wells without necessarily requiring a new wipe pass be acquired each time (i.e. once the "$P_1, \ldots P_\alpha, \ldots P_n$" parameters have been determined for a set of fluids over the entire length of a well, determining them again on nearby offset wells may be avoided where the same type of fluids are expected to be encountered as well.

Although the curves from the drill and wipe pass now overlay, there may remain some residual statistical noise. One may therefore take the average of the drill and wipe pass porosities as the "final" apparent porosity, and the statistical error between the drill and wipe pass porosities may be used to assess the precision of such computed final true porosity.

Using the foregoing procedure to minimize the difference between the apparent porosities from different snapshots, despite the x-constituent substitutions that have taken place, results in a final apparent porosity (i.e. the resulting identical drill and wipe pass apparent porosities), which has the new benefit of being independent of the actual fluid composition present in the pore space, and depends on the rock mineralogy. The apparent porosity "$PHI^{(a)}_{P1, \ldots P\alpha, \ldots Pn}$", may then be converted into "true" porosity in a last computational operation, as follows (as per FIG. 14C, whereby the porosity is computed as "1" minus the ratio of the distance of the measurement point "M" to the porosity hyper-plane, to the distance of the matrix end-point "Mtx" to the porosity hyper-plane):

$$\text{True Porosity } PHI = \frac{PHI^{(a)}_{P1, \ldots P\alpha, \ldots Pn}(M) - PHI^{(a)}_{P1, \ldots P\alpha, \ldots Pn}(Mtx)}{100 p.u. - PHI^{(a)}_{P1, \ldots P\alpha, \ldots Pn}(Mtx)}$$

Note that although the discussion herein refers to fluids occupying the pore space, the method described herein is well suited to the case in which salt mineral partially occludes the pore space and then goes into solution when drilling WBM filtrate invades the formation. In this case, although not a fluid, salt is considered among the constituents included in the porosity hyper-plane. Determining the true porosity is particularly suited for a tool sold under the trademark EcoScope™ (which is a trademark of Schlumberger Technology Corporation) since various measurements from such tool are consonant, and the tool provides up to four different apparent porosity measurements, which can be mixed to solve for true porosity with up to four different fluids occupying the pore space. In practice, these four porosities do not have to be used simultaneously, and the number of measurements to be used is at maximum the number of different fluids occupying the pore space of the formation.

An automatic way to select the number of measurements to be used would be to start, for example, with an apparent neutron porosity, and to observe if the while drilling and wipe pass measurements match. If not, then consider the apparent density porosity in addition, and determine if the foregoing measurements may be mixed to make the while drilling and wipe pass measurements match. If that still does not work, then further consider the apparent SIGMA porosity and determine if the three such measurement types may be mixed to make the drill and wipe pass measurements match. The foregoing process may be continued with other additional measurement parameters. Additional aids may be neutron spectroscopy (e.g. "thermal neutron capture spectroscopy"), or mud logging, which may provide the matrix information that allows us to compute "$PHI^{(a)}_{P1, \ldots P\alpha, \ldots Pn}(Mtx)$".

Again, where salt mineral, etc., partially occludes the pore space and then goes into solution with drilling WBM filtrate invading the formation, the resulting invasion profile becomes an unconventional two-step (i.e. involving two interfaces or boundaries) axisymmetric invasion profile with-respect-to the wellbore, with the formation volume situated between the borehole and the first interface closest to the wellbore including a salt-free zone and intact WBM filtrate, the next/deeper formation volume situated in-between the two interfaces including intact salt occluding the pore space and salt-saturated WBM filtrate, and the remaining outer formation volume situated beyond the second/deepest interface including undisturbed formation, which may be addressed and solved for, using the unique suite of consonant measurements from a tool such as the EcoScope™ tool, including time-lapse data acquisition (i.e. including acquiring data from both a drill and wipe pass).

Discussed below is the application of log measurements signature analysis techniques to standalone NMR data, using time-lapse or MDOI data acquisition (or any combination thereof). What will be described is a successful implementation of the methods and procedures described above, and additional related operations in the particular case of NMR well log measurements. Moreover, a totally unconstrained linear fluid volumetric interpretation (inversion) workflow is introduced, using a covariance-based volume redistribution technique.

The resulting answer from the successful implementation of the methods and procedures described above, may be expressed as:

$$\left\{\begin{array}{l}\text{Elemental}\\\text{Spectroscopy logs}\\\text{(for mineralogy)}\end{array}\right\} + \left\{\begin{array}{l}\text{Nuclear Magnetic}\\\text{Resonance logs}\\\text{(for fluid volumetrics)}\end{array}\right\} =$$

Provides for complete Formation Volumetrics

The foregoing would: (a) constitute a sourceless logging alternative (i.e. a well logging alternative that does not involve the usage of chemical radioactive sources to be deployed inside the well); (b) use two sets of measurements (neutron spectroscopy and NMR); (c) allow for solving for three-phase formation fluid volumetrics (gas, oil, and water); (d) and be substantially immune, to a large extent, to water salinity effects (e.g. variable salinity water or fresh water).

The immediate application of the techniques described to NMR well log measurements results from the following. NMR log measurements, in general, comprise many components which may be construed to constitute a plurality of individual and truly consonant separate measurements. Further, NMR log measurements, from gradient tools (those in which the sensitive measurement volume has a magnetic field gradient) in particular, probe a relatively small, focused, and well-defined geometrical volume that may be located a few inches from the wellbore wall (e.g. 2.75 inches for an 8.5 inch wellbore, in the case of the proVISION™ tool). Therefore, the measurement is insensitive to the first few inches of invasion. As such, LWD measurements, when combined with a fast drilling rate-of-penetration (ROP) and/or when the LWD tool is the bottommost tool in the BHA, may be considered to sample the un-invaded virgin zone (undisturbed zone), whereas the wipe pass may be substantially affected by invasion and provide the desired contrast.

NMR fluid signatures may be relatively simple to identify—to within a normalization factor—because different fluid signatures belong in different and rather well-defined regions of the NMR distribution spectra considered. NMR measurements mixing laws may be taken to be linear, which may not be the case for other log measurements such as resistivity, neutron porosity, or acoustic logs. NMR data may be displayed in a variety of ways, such as distributions, echo trains, or any linear transformation thereof to simulate uni- or multi-dimensional bins or window echo sums.

The example described corresponds to a "clastic" environment (i.e. shaly-sandstone formations) with native gas and fresh water (four parts per thousand salinity) present in the pore spaces, and drilled over-balance with OBM drilling fluid. The formation constituents present may include: clay mineral(s), wetting clay-bound water, siltstone (quartz mineral), wetting capillary bound water in the siltstone pores, sandstone (quartz mineral), non-wetting fluid native gas in the sandstone pores in the undisturbed virgin zone, wetting native water in the sandstone pores in the undisturbed virgin zone, non-wetting residual gas in the flushed zone (also called "invaded zone" spoiled by mud-filtrate invasion), wetting residual bound water film lining the sandstone grains in the flushed zone, and OBM drilling fluid filtrate.

Native formation hydrocarbon gas and water fluids have been assumed in the following, although earlier figures and classification techniques pointed to traces of an additional fluid type such as hydrocarbon oil. Although native formation water in the sandstone pores was treated as "one" and assigned "one" predominant signature, it also would have been possible to introduce multiple water signatures corresponding to different pore sizes to be more particular.

FIG. 23 summarizes one embodiment of the NMR interpretation workflow. The operations in the workflow are presented in the left hand side of the flow diagram, and corresponding figures for these operations are shown on the right.

FIGS. 24 and 25 show integration of $T_2$ distributions over depth (FIG. 24), followed by integration over cumulative $T_2$'s (FIG. 25). Data from the drill pass is represented by plots 240, 250, and data from the wipe pass is represented by plots 241, 251 in FIGS. 24 and 25, respectively. The location of the point where the drill and wipe pass curves depart from each other on FIG. 24 corresponds to the appropriate bound fluid T2 cut-off to use (in this instance 33 msec). Intervals with $T_2$ distributions below this cut-off may be interpreted as including clay mineral(s), siltstone (quartz mineral), clay-bound water, and capillary bound water in just the siltstone pores, for example.

FIGS. 26A through 26F show T2 distributions from the drill and wipe pass selected over zones of interest, for a cross-zone constrained mode extraction. FIGS. 27A through 27H and 28A, 28B show curve fit results from the zones and passes displayed together, including underlying extracted Gaussian modes. A non-linear least squares fit used the same Gaussian modes between different zones (on the same measurement pass), the same Gaussian center but possibly with different width between different measurement passes (in the same zone), and the same (or correlated) Gaussian area between different passes (in same zone) when the Gaussian modes pertained to bound fluids.

FIGS. 29 and 30 are a summary of different fluid constituents' NMR "concatenated" apparent signatures normalized to one (i.e. 100 p.u.). These responses were presented in "$T_2$ distribution format" or "spin echo amplitude format", but they may be presented in other possible "formats" depending on the former two through a linear transformation such as uni- or multi-dimensional "porosity bins" or "echo window sums". FIG. 29 shows a summary of different fluid constituents' NMR signatures in "$T_2$ format" (as derived from FIGS. 27A through 27H, and 28A, 28B). Note how changes in fluid signatures in-between different snapshots (i.e. in-between the drill and wipe pass) is accounted for by assigning a "concatenated drill ⊕ wipe pass" signature (including in this instance, of 80 merged components=40 drill ⊕ 40 wipe NMR T2 distribution components). The displayed signatures are normalized to one (i.e. 100 p.u.). In FIGS. 29 and 30, plot lines or points 290-297 respectively correspond to the following: clay bound water; capillary bound water in the siltstone pores; free water present in the sandstone pores, displaced in-between the drill and wipe pass; residual water present in the sandstones pores during the wipe pass; native gas displaced by the drilling OBM filtrate in-between the drill and wipe pass; residual native gas present in the sandstone pores during the wipe pass; drilling OBM filtrate present in the sandstone pores during the drill pass; and additional drilling OBM filtrate that has invaded the sandstone pores in-between the drill and wipe pass.

FIG. 30 shows a summary of different fluid constituents' NMR apparent signatures, converted from "$T_2$ format" above to "spin echo amplitude format" and reflecting the same NMR CPMG sequence used during the data acquisition operation. Because thermal noise present on raw spin echo amplitudes may be considered uncorrelated, the corresponding covariance matrix will be "diagonal", making echo trains more appropriate for the subsequent fluid elemental volumetric interpretation (inversion) operation. $T_2$ distributions, on the other hand, are the outcome of an ill-posed linear inversion requiring regularization techniques which affect the resulting covariance matrix of the corresponding $T_2$ components. Working in with $T_2$ distributions to identify and classify the different fluid constituents present is quite common, however echo trains are better suited for the fluid elemental volumetric analysis operation FIG. 31A shows a fluid elemental volumetric analysis, solving for "apparent" volumes (i.e., not adjusted for HI and polarization factors). Stacked from the bottom up are clay bound water (curve 310), capillary bound water in the siltstone pores (curve 311), water in the sandstone pores at the time of the drill pass (curve 312), drilling OBM filtrate already present at the time of the drill pass (curve 313), movable gas present at the time of the drill pass (curve 314), and residual gas observed at the time of the wipe pass (curve 315). A simple linear inversion, which inherently provides for speed, interactivity, and ease of implementation was performed. Furthermore, the various input measurement noise characteristics and cross-correlation (or absence thereof) are explicitly accounted for, while incorporating the corresponding covariance matrix in the inversion. However, whereas traditional Formation Volumetrics constrains formation constituents volumes to "$0 \leq V \leq 1$", a direct linear solution such as presented here, may instead produce negative values. This may result from noise in the input data, existing inaccuracies in the derived fluids NMR signatures, or minor depth mismatches between the different snapshots. These negative values translate into "reverse curve ordering", as can be observed in a few spots in the present figure (for example, the curve 314 sometimes goes below the curve 315, or the curve 312 sometimes goes below the curve 311). The technique proposed to remedy these negative values is to redistribute them among the other formation constituents present, according to the cross-correlations existing in-between the inverted formation constituents' volumes. This is promptly achieved by propagating the covariance matrix from the input NMR measurements to the output apparent volumes, as shown in FIG. 32. Volume redistribution is also a linear process and does not affect the presented technique's speed, interactivity, or ease of implementation.

FIG. 31B shows a fluid elemental volumetric analysis, solving for "adjusted" apparent volumes, after redistributing negative values, using the covariance matrix from FIG. 32. Note the absence of reverse curve ordering in this case. FIG. 32 is a visual display of the covariance matrix of the original apparent volumes (before adjustment), in which the plot lines 320-326 represent the following constituents, respectively: clay bound water; capillary bound water in the siltstone pores; water present in the sandstones pores; drilling OBM filtrate present in the sandstone pores during the drill pass; native gas displaced by the drilling OBM filtrate in-between the drill and wipe pass; OBM filtrate present in the sandstone pores during the wipe pass; and residual native gas present in the sandstone pores during the wipe pass.

FIG. 33 shows a final fluid elemental volumetric analysis, solving for "true" fluid volumes, after correcting the adjusted apparent fluid volumes for the corresponding combined effects of HI and polarization factor. Stacked from the bottom up are clay-bound-water (shading 330), capillary bound water in the siltstone pores (shading 331), water in the sandstone pores at the time of the drill pass (shading 332), OBM filtrate already present at the time of the drill pass (shading 333), movable gas present at the time of the drill pass (shading 334), and residual gas observed at the time of the wipe pass (shading 335). The porosity scale is 0-30 percent (or porosity units p.u.). FIG. 34 is a summary of the successful implementation of the petrophysical "equation" (or statement) "Elemental Spectroscopy logs (for mineralogy)" (track 340)+"Nuclear Magnetic Resonance logs (for fluid elemental volumetrics)" (track 341)="All you need for complete Formation Volumetrics" (track 342).

An example computing system 200 is shown in FIG. 35 in accordance. The computing system 200 may be an individual computer system 201A, or an arrangement of distributed computer systems. The computer system 201A may include one or more analysis modules 202 that are configured to perform various tasks according to some embodiments, such as the tasks depicted in FIG. 23. To perform these various tasks, the analysis module 202 may execute independently, or in coordination with, one or more processors 204, which may be connected to one or more storage media 206. The processor(s) 104 may also be connected to a network interface 208 to allow the computer system 201A to communicate over a data network 209 with one or more additional computer systems and/or computing systems, such as 201B, 201C, and/or 201D (note that computer systems 201B, 201C and/or 201D may or may not share the same architecture as computer system 201A, and may be located in different physical locations, e.g. computer systems 201A and 201B may be on a ship underway on the ocean, in a land based office building or at a well site while in communication with one or more computer systems such as 101C and/or 101D that are located in one or more data centers on shore, other ships, and/or located in varying countries on different continents).

A processor may include a microprocessor, microcontroller, processor module or subsystem, programmable integrated circuit, programmable gate array, or another control or computing device.

The storage media 206 can be implemented as one or more computer-readable or machine-readable storage media. Note that while in the example embodiment of FIG. 35 storage media 206 is depicted as within computer system 201A, in some embodiments, storage media 206 may be distributed within and/or across multiple internal and/or external enclosures of computing system 201A and/or additional computing systems. Storage media 206 may include one or more different forms of memory including semiconductor memory devices such as dynamic or static random access memories (DRAMs or SRAMs), erasable and programmable read-only memories (EPROMs), electrically erasable and programmable read-only memories (EEPROMs) and flash memories; magnetic disks such as fixed, floppy and removable disks; other magnetic media including tape; optical media such as compact disks (CDs) or digital video disks (DVDs); or other types of storage devices. Note that the instructions discussed above can be provided on one computer-readable or machine-readable storage medium, or may be provided on multiple computer-readable or machine-readable storage media distributed in a large system having possibly plural nodes. Such computer-readable or machine-readable storage medium or media is (are) considered to be part of an article (or article of manufacture). An article or article of manufacture can refer to any manufactured single component or multiple components. The storage medium or media may be located either in the machine running the machine-readable instructions, or located at a remote site from which machine-readable instructions can be downloaded over a network for execution.

It should be appreciated that computing system 200 is an example of a computing system, and that computing system 200 may have more or fewer components than shown, may combine additional components not depicted in the example embodiment of FIG. 35, and/or computing system 200 may have a different configuration or arrangement of the components depicted in FIG. 35. The various components shown in FIG. 35 may be implemented in hardware, software, or a combination of both hardware and software, including one or more signal processing and/or application specific integrated circuits.

Further, the operations in the processing methods described above may be implemented by running one or more functional modules in information processing apparatus such as general purpose processors or application specific chips, such as ASICs, FPGAs, PLDs, or other appropriate devices. These modules, combinations of these modules, and/or their combination with general hardware are included within the scope of protection of the invention.

An example well-logging method which may be performed by the processor 34 of FIG. 1 is now described with reference to the flow diagram 360 of FIG. 6. Beginning at Block 360, the method illustratively includes collecting NMR snapshots (e.g., time-lapse or MDOI NMR data) indicative of changes in the geological formation, as discussed above (Block 362). The method further illustratively includes identifying a plurality of fluids within the geological formation based upon the NMR data, at Block 363, and determining respective NMR signatures for the identified fluids based upon the NMR data, at Block 364, as also described above. In addition, apparent adjusted volumes may be determined for the identified fluids based upon the NMR signatures, at Block 365, and true volumes for the identified fluids may be determined based upon the apparent volumes, at Block 366, as described further above. The method illustratively concludes at Block 367.

Many modifications and other embodiments will come to the mind of one skilled in the art having the benefit of the teachings presented in the foregoing descriptions and the associated drawings. Therefore, it is understood that various modifications and embodiments are intended to be included within the scope of the appended claims.

That which is claimed is:

1. A well-logging method for a geological formation having a borehole therein, the method comprising:
   collecting a plurality of nuclear magnetic resonance (NMR) snapshots from the borehole indicative of changes in the geological formation and defining NMR data;
   identifying a plurality of fluids within the geological formation based upon the NMR data;
   determining respective NMR signatures for the identified fluids based upon the NMR data;
   determining apparent volumes for the identified fluids based upon the NMR signatures; and
   adjusting said determined apparent volumes for a hydrogen index and a polarization factor to determine adjusted volumes for the identified fluids.

2. The method of claim 1 wherein the NMR snapshots comprise time-lapse NMR snapshots.

3. The method of claim 1 wherein the NMR snapshots comprise multi-depth-of-investigation (MDOI) nuclear magnetic resonance (NMR) snapshots.

4. The method of claim 1 further comprising:
   determining true volumes for the identified fluids based upon the adjusted volumes.

5. The method of claim 1 wherein determining the adjusted volumes comprises determining the adjusted volumes by redistributing the apparent volumes using a volume covariance matrix.

6. The method of claim 1 wherein the geological formation along the length of the borehole has at least one matrix composition associated therewith; and wherein determining the adjusted volumes comprises determining the adjusted volumes further based upon the at least one matrix composition.

7. The method of claim 6 wherein the length of the borehole traverses a plurality of zones in the geological formation each having a respective matrix composition associated therewith; and wherein determining the adjusted volumes comprises determining the adjusted volumes further based upon the respective matrix compositions for each zone.

8. The method of claim 1 wherein determining the respective NMR signatures for the identified fluids comprises determining respective NMR signatures for the identified fluids further based upon a Gaussian function.

9. The method of claim 1 further comprising converting the NMR signatures into an echo domain prior to determining the apparent volumes for the fluids.

10. The method of claim 1 wherein identifying the plurality of fluids within the geological formation comprises identifying the plurality of fluids based upon NMR cutoffs.

11. A well-logging system comprising;
a well-logging tool to collect a plurality of nuclear magnetic resonance (NMR) snapshots from a borehole in the geological formation indicative of changes in the geological formation and defining NMR data; and
a processor to
identify a plurality of fluids within the geological formation based upon the NMR data,
determine respective NMR signatures for the identified fluids based upon the NMR data,
determine apparent volumes for the identified fluids based upon the NMR signatures, and
adjust said determined apparent volumes for a hydrogen index and a polarization factor to determine adjusted volumes for the identified fluids based upon the apparent volumes.

12. The well-logging system of claim 11 wherein the NMR snapshots comprise time-lapse NMR snapshots.

13. The well-logging system of claim 11 wherein the NMR snapshots comprise multi-depth-of-investigation (MDOI) nuclear magnetic resonance (NMR) snapshots.

14. The well-logging system of claim 11 wherein said processor further determines true volumes for the identified fluids based upon the adjusted volumes.

15. The well-logging system of claim 11 wherein said processor determines the adjusted volumes by redistributing the apparent volumes using a volume covariance matrix.

16. The well-logging system of claim 11 wherein the geological formation along the length of the borehole has at least one matrix composition associated therewith; and wherein said processor determines the adjusted volumes further based upon the at least one matrix composition.

17. A non-transitory computer-readable medium having computer-executable instructions for causing a computer to:
identify a plurality of fluids within a geological formation based upon a plurality of nuclear magnetic resonance (NMR) snapshots from a borehole within the geological formation indicative of changes in the geological formation and defining NMR data;
determine respective NMR signatures for the identified fluids based upon the NMR data;
determine apparent volumes for the identified fluids based upon the NMR signatures; and
adjust said determined apparent volumes for a hydrogen index and a polarization factor to determine adjusted volumes for the identified fluids based upon the apparent volumes.

18. The non-transitory computer-readable medium of claim 17 wherein the NMR snapshots comprise time-lapse NMR snapshots.

19. The non-transitory computer-readable medium of claim 17 wherein the NMR snapshots comprise multi-depth-of-investigation (MDOI) nuclear magnetic resonance (NMR) snapshots.

20. The non-transitory computer-readable medium of claim 17 further including computer-executable instructions for causing a computer to determine true volumes for the identified fluids based upon the adjusted volumes.

21. The non-transitory computer-readable medium of claim 17 wherein the adjusted volumes are determined by redistributing the apparent volumes using a volume covariance matrix.

22. The non-transitory computer-readable medium of claim 17 wherein the geological formation along the length of the borehole has at least one matrix composition associated therewith; and wherein the adjusted volumes are determined further based upon the at least one matrix composition.

23. A well-logging method for a geological formation having a borehole therein, the method comprising:
collecting a plurality of nuclear magnetic resonance (NMR) snapshots from the borehole indicative of changes in the geological formation and defining NMR data;
identifying a group NMR signature of the fluids present within the geological formation based upon the NMR data;
determining snapshot-independent apparent NMR porosity based upon the group NMR signature and the NMR data;
collecting well data indicative of the geological formation mineralogy; and
determining snapshot-independent true NMR porosity based upon the snapshot-independent NMR apparent porosity and the formation mineralogy.

* * * * *